US012807637B2

(12) United States Patent
Goldberg et al.

(10) Patent No.: US 12,807,637 B2
(45) Date of Patent: Nov. 24, 2026

(54) COMPOSITIONS AND METHODS FOR TRANSIENT GENE THERAPY WITH ENHANCED STABILITY

(71) Applicant: Dana-Farber Cancer Institute, Inc., Boston, MA (US)

(72) Inventors: Michael Solomon Goldberg, Brookline, MA (US); Ellese Carmona, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 606 days.

(21) Appl. No.: 18/225,476

(22) Filed: Jul. 24, 2023

(65) Prior Publication Data

US 2024/0076309 A1 Mar. 7, 2024

Related U.S. Application Data

(62) Division of application No. 16/604,609, filed as application No. PCT/US2018/027665 on Apr. 13, 2018, now Pat. No. 11,753,434.

(60) Provisional application No. 62/485,619, filed on Apr. 14, 2017.

(51) Int. Cl.

| | |
|---|---|
| ***C07H 21/00*** | (2006.01) |
| ***A61K 35/17*** | (2025.01) |
| ***A61K 48/00*** | (2006.01) |
| ***C07K 14/505*** | (2006.01) |
| ***C12P 19/30*** | (2006.01) |

(52) U.S. Cl.

CPC ............ *C07H 21/00* (2013.01); *A61K 35/17* (2013.01); *C07K 14/505* (2013.01); *C12P 19/30* (2013.01); *A61K 48/00* (2013.01)

(58) Field of Classification Search

None

See application file for complete search history.

(56) References Cited

U.S. PATENT DOCUMENTS

| | | | |
|---|---|---|---|
| 5,773,244 | A | 6/1998 | Ares, Jr. et al. |
| 5,948,902 | A | 9/1999 | Honkanen et al. |
| 7,303,901 | B2 | 12/2007 | Hjorleifsdottir et al. |
| 8,911,993 | B2 | 12/2014 | June et al. |
| 2008/0131899 | A1 | 6/2008 | Landegren et al. |
| 2016/0083747 | A1 | 3/2016 | Kruse |
| 2017/0204422 | A1 | 7/2017 | Nelson et al. |
| 2018/0169146 | A1 | 6/2018 | Goldberg et al. |

FOREIGN PATENT DOCUMENTS

| | | | |
|---|---|---|---|
| EP | 0992583 | A1 | 4/2000 |
| WO | WO-0015779 | A2 | 3/2000 |
| WO | WO-2010084371 | A1 | 7/2010 |
| WO | WO-2012170930 | A1 | 12/2012 |
| WO | WO-2013143698 | A1 | 10/2013 |
| WO | WO-2014186334 | A1 | 11/2014 |
| WO | WO-2016011222 | A2 | 1/2016 |
| WO | WO-2016197121 | A1 | 12/2016 |

OTHER PUBLICATIONS

Bahrulolum, et al. (2025) “CircRNA: Unlocking new frontiers in therapeutic and vaccine development”, Molecular Therapy, 34(2):748-70. (Year: 2025).*

Abe N., et al., “Rolling Circle Translation of Circular RNA in Living Human Cells,” Scientific Reports, Nov. 10, 2015, vol. 5, No. 1, XP055511341.

Beaudry D., et al., “An Efficient Strategy for the Synthesis of Circular RNA Molecules,” Nucleic Acids Research, Aug. 11, 1995, vol. 23, No. 15, pp. 3064-3066.

Breslauer K.J., et al., “Predicting DNA Duplex Stability from the Base Sequence”, Proceedings of the National Academy of Sciences of the United States of America, Jun. 1, 1986, vol. 83, No. 11, pp. 3746-3750.

Chen C-Y., et al., “Initiation of Protein Synthesis by the Eukaryotic Translational Apparatus on Circular RNAs,” Science, Jan. 1, 1995, vol. 268, pp. 415-417, XP055302939, Sep. 15, 2016, Retrieved from URL: http://science.sciencemag.org/content/sci/268/5209/415.full.pdf.

Chen, et al., “Internal Ribosome Entry Sites Tests with Circular mRNAs,” Methods in Molecular Biology, 1998, vol. 77, pp. 355-363.

Dumousseau M., et al., “Melting, A Flexible Platform to Predict the Melting Temperatures of Nucleic Acids”, BMC Bioinformatics, Dec. 2012, vol. 13, No. 101, 12 Pages.

Extended European Search Report for European Application No. 18784503.7 and PCT/US2018027665, mailed May 10, 2021, 20 Pages.

Freier S.M., et al., “Improved Free-Energy Parameters for Predictions of RNA Duplex Stability”, Proceedings of the National Academy of Sciences of the United States of America, Dec. 1, 1986, vol. 83, No. 24, pp. 9373-9377.

Ho C.K., et al., “Bacteriophage T4 RNA Ligase 2 (gp24.1) Exemplifies a Family of RNA Ligases Found in all Phylogenetic Domains,” Proceedings of the National Academy of Sciences of the United States of America, Oct. 1, 2002, vol. 99, No. 20, pp. 12709-12714, DOI:10.1073/pnas.192184699.

International Preliminary Report on Patentability for International Application No. PCT/US2016/036045, mailed Dec. 14, 2017, 9 Pages.

International Preliminary Report on Patentability for International Application No. PCT/US2018/027665, mailed Oct. 24, 2019, 10 Pages.

International Search Report and Written Opinion for International Application No. PCT/US2016/036045, mailed Sep. 27, 2016, 12 Pages.

International Search Report and Written Opinion for International Application No. PCT/US2018/027665, mailed Sep. 4, 2018, 19 Pages.

(Continued)

*Primary Examiner* — Robert M Kelly

(74) *Attorney, Agent, or Firm* — Mueting Raasch Group

(57) ABSTRACT

The present invention provides circularized RNA and methods of making, purifying, and using same.

24 Claims, 45 Drawing Sheets

Specification includes a Sequence Listing.

(56) References Cited

OTHER PUBLICATIONS

Jeck W.R., et al., "Circular RNAs are Abundant, Conserved, and Associated with ALU Repeats," RNA, Feb. 1, 2013, vol. 19, No. 2, pp. 141-157, DOI:10.1261/rna.035667.112, ISSN: 1355-8382, XP055200830.
Kariko K., et al: "Generating the 1 Optimal mRNA for Therapy: HPLC Purification Eliminates Immune Activation and Improves Translation of Nucleoside-Modified, Protein-Encoding mRNA", Nucleic Acids Research, Oxford University Press, GB, vol. 39, No. 21, Nov. 1, 2011, pp. e142-e141, DOI: 10.1093/NAR/GKR695, ISSN: 1362-4962, XP002696190, [Retrieved on Sep. 2, 2011].
Kibbe W.A., "OligoCalc: An Online Oligonucleotide Properties Calculator," Nucleic Acids Research, Jul. 2007, vol. 35, (Web Server Issue), pp. W43-W46.
Mhaidly, et al., "The Future: In Vivo CAR T Cell Gene Therapy," Molecular Therapy, 2019, vol. 27, No. 4, pp. 707-709.
Müller S., et al., "In Vitro Circularization of RNA," RNA Biology, Sep. 26, 2016, vol. 14, No. 8, pp. 1018-1027, XP055488935.
Moore, et al., "Site-Specific Modification of Pre-mRNA: The 2'-Hydroxyl Groups at the Splice Sites," Science. May 15, 1992, vol. 256, No. 5059, pp. 992-997.
Partial Supplementary European Search Report for European Application No. 18784503.7, mailed Dec. 18, 2020, 14 Pages.
Puttaraju, et al., "Group I Permuted Intron-Exon (PIE) Sequences Self-Splice to Produce Circular Exons," Nucleic Acids Research, Oct. 25, 1992, vol. 20, No. 20, pp. 5357-5364.
Ramishetti, et al., "Systemic Gene Silencing in Primary T Lymphocytes Using Targeted Lipid Nanoparticles," ACS Nano, Jul. 28, 2015, vol. 9, No. 7, pp. 6706-6716, DOI: 10.1021/acsnano.5b02796, Epublished Jun. 10, 2015.
Rychlik, et al., "Optimization of the Annealing Temperature for DNA Amplification in Vitro," Nucleic Acids Research, Nov. 11, 1990, vol. 18, No. 21, pp. 6409-6412, Erratum in Nucleic Acids Research, Feb. 11, 1991, vol. 19, No. 3, p. 698.
Sahin U., et al., "mRNA-Based Therapeutics—Developing a New Class of Drugs," Nature Reviews Drug Discovery, 2014, vol. 13, pp. 759-780, Retrieved from URL: https://doi.org/10.1038/nrd4278.
Shi et al., "Biodistribution of Small Interfering RNA at the Organ and Cellular Levels after Lipid Nanoparticle-Mediated Delivery," ournal of Histochemistry and Cytochemistry, Aug. 2011, vol. 59, No. 8, pp. 727-740, PMID: 21804077, PMCID: PMC3261601, DOI: 10.1369/0022155411410885.
Valdmanis P.N., et al., "The Expanding Repertoire of Circular RNAs, " Molecular Therapy, GB, Jun. 1, 2013, vol. 21, No. 6, pp. 1112-1114, DOI:10.1038/mt.2013.101, ISSN 1525-0016, XP055295216.
Wang, et al., "Oligoribonucleotide Circularization by 'Template-Mediated' Ligation with T4 RNA Ligase: Synthesis of Circular Hammerhead Ribozymes," Nucleic Acids Research, May 15, 1998, vol. 26, No. 10, pp. 2502-2504.
Zecherle, et al., "Purines are Required at the 5' Ends of Newly Initiated RNAs for Optional RNA Polymerase III Gene Expression," Molecular and Cellular Biology, Oct. 1996, vol. 16, No. 10, pp. 5801-5810.
Zhao et al., "Multiple Injections of Electroporated Autologous T Cells Expressing a Chimeric Antigen Receptor Mediate Regression of Human Disseminated Tumor," Cancer Research, Nov. 15, 2010, vol. 70, No. 22, pp. 9053-9061, PMID: 20926399, PMCID: PMC2982929, DOI: 10.1158/0008-5472.CAN-10-2880, Epublished Oct. 5, 2010.

* cited by examiner

| Linear mRNA | | |
|---|---|---|
| cT Value | NLuc | Actin |
| 6 h | 11.04 | 19.79 |
| 24 h | 14.35 | 20.50 |
| 72 h | 15.65 | 21.08 |

| Circular mRNA | | |
|---|---|---|
| cT Value | NLuc | Actin |
| 6 h | 13.10 | 21.18 |
| 24 h | 10.34 | 19.06 |
| 72 h | 11.37 | 21.07 |

| Construct | 5' CRC | SEQ ID NO | 3'CRC | SEQ ID NO | CRC Length | # Mutation | Melting Temp (°C) | Temp Range (°C) |
|---|---|---|---|---|---|---|---|---|
| 1 | GCACGAATTGCACAATCGGTACGTTCGAGT | 1 | ACTCGAACGTACCGATTGTGCAATTCGTGC | 88 | 30 | 0 | 74 | |
| 2 | GCACGAATTGCACAATCGGT | 3 | ACCGATTGTGCAATTCGTGC | 89 | 20 | 0 | 67 | Tm > 37° |
| 3 | GCACGAATTGCACAA | 6 | TTGTGCAATTCGTGC | 90 | 15 | 0 | 54 | |
| 4 | GCACGAATTGCACAATCGGT | 3 | ACCGATTGTCCAATCCGTGC | 27 | 20 | 2 | 35.35 | |
| 5 | GCACGAATTGCACAATCGGT | 3 | ACCGGTTGTACAATCCGTGC | 36 | 20 | 3 | 29.33 | 25° <Tm< 37° |
| 6 | GCACGAATTGCACAA | 6 | TTGTCCAATTCGTGC | 42 | 15 | 1 | 26.15 | |
| 7 | GCACGAATTGCACAA | 6 | TTGTGAAATTGGTGC | 91 | 15 | 2 | 17.1 | |
| 8 | GCACGAATTGCACAA | 6 | TTGTCCAATTAGTGC | 92 | 15 | 2 | 9.45 | Tm < 25° |
| 9 | GCACGAATTG | 87 | CAATTTGTGC | 93 | 10 | 1 | 2.04 | |

FIG. 4A (C)

| *Predicted Status of CRC During Ligation Reaction (16 °C)* | *Predicted Status of CRC at Physiological Temperature (37 °C)* |
| --- | --- |
| Intact | Intact |
| Intact | Dissociated |
| Disassociated | Dissociated |

* This IVT product was treated with RppH to obtain monophosphate 5′ end prior to ligation

HPLC Sequence Method

Quat. Pump

| | |
|---|---|
| Flow : | 0.500 mL/min |
| Low Pressure Limit : | 0.00 bar |
| High Pressure Limit : | 200.00 bar |
| Maximum Flow Gradient : | 100.000 mL/min² |
| Primary Channel : | Automatic |

Solvent Composition

| Channel | Name 1 | Used | Percent (%) |
|---|---|---|---|
| A | H2O 0.1% TEAA | Yes | 80.0 |
| B | ACN 25% TEAA | Yes | 20.0 |
| C | H2O | No | |
| D | MeOH 0.1% TFA | No | |

Timetable

| Time (min) | A (%) | B (%) | C (%) | D (%) | Flow (mL/min) | Pressure (bar) |
|---|---|---|---|---|---|---|
| 4.00 | 75.0 | 25.0 | 0.0 | 0.0 | 0.500 | 200.00 |
| 6.00 | 70.0 | 30.0 | 0.0 | 0.0 | 0.500 | 200.00 |
| 8.00 | 65.0 | 35.0 | 0.0 | 0.0 | 0.500 | 200.00 |
| 10.00 | 60.0 | 40.0 | 0.0 | 0.0 | 0.500 | 200.00 |
| 30.00 | 50.0 | 50.0 | 0.0 | 0.0 | 0.500 | 200.00 |
| 32.00 | 30.0 | 70.0 | 0.0 | 0.0 | 0.500 | 200.00 |
| 34.00 | 0.0 | 100.0 | 0.0 | 0.0 | 0.500 | 200.00 |
| 35.00 | 80.0 | 20.0 | 0.0 | 0.0 | 0.500 | 200.00 |

or NLuc

COMPOSITIONS AND METHODS FOR TRANSIENT GENE THERAPY WITH ENHANCED STABILITY

RELATED APPLICATIONS

This application is a divisional application of U.S. application Ser. No. 16/604,609, which was filed on Oct. 11, 2019, which is a national stage filing under 35 U.S.C. § 371 of International Application No. PCT/US2018/027665, filed Apr. 13, 2018, which claims the benefit under 35 U.S.C. § 119(e) of U.S. provisional application No. 62/485,619, filed Apr. 14, 2017, the entire contents of each of which are incorporated herein by reference in their entireties.

REFERENCE TO A SEQUENCE LISTING XML

This application contains a Sequence Listing which has been submitted electronically in XML format. The Sequence Listing XML is incorporated herein by reference. Said XML file, created on Aug. 19, 2023, is named 5031461-000106-US3_SL.xml and is 84,713 bytes in size.

FIELD OF THE INVENTION

The present invention relates generally to compositions of circularized RNA, method of producing, purifying, and using same.

BACKGROUND OF THE INVENTION

Circular RNA is useful in the design and production of stable forms of RNA. Circular RNA can also be particularly interesting and useful for in vivo applications, especially in the research area of RNA-based control of gene expression and therapeutics, including protein replacement therapy and vaccination.

Prior to this invention, there were three main techniques for making circularized RNA in vitro: splint-mediated method, permuted intron-exon method, and RNA ligase-mediated method.

However, the existing methodologies are limited by quantities of circularized RNA that can be produced and by the size of RNA that can be circularized, thus limiting their therapeutic application.

It is therefore a primary object of the current invention to provide a general method for preparation and purification of a desired RNA in circularized form that is not limited by quantity or size constraints of conventional techniques.

SUMMARY OF THE INVENTION

The invention features a nucleic acid including a 5' imperfect complement-reverse complement (iCRC) sequence; a 5' untranslated region (UTR) sequence; an RNA sequence; a 3' UTR sequence; and a 3' iCRC sequence. The 5' iCRC sequence and the 3' iCRC sequence have the following characteristics: one or more nucleotide mismatches such that the 5' iCRC sequence and the 3' iCRC are not 100% complementary; an annealing temperature ($T_a$) less than 16° C.; and a melting temperature ($T_m$) greater than 37° C.

The RNA sequence may be capable of being translated into a polypeptide, may comprise a RNA that is a reverse complement of an endogenous RNA, e.g., an mRNA, a miRNA, a tRNA, an rRNA, or a lncRNA, or may be capable of binding to an RNA-binding protein (RBP).

The nucleic acid may further include at least one random nucleotide sequence comprising between 5 and 25 nucleotides, e.g., 10 to 50 nucleotides, (e.g., 10, 15, or 20 nucleotides). The random nucleotide sequence is located at the nucleic acid's 5' end and/or the nucleic acid's 3' end.

A 5' random nucleotide sequence may be located at the nucleic acid's 5' end and/or the 3' random nucleotide sequence is located at the nucleic acid's 3' end; the 5' random nucleotide sequence may be located upstream of the 5' iCRC sequence and/or the 3' random nucleotide sequence is located downstream of the 3' iCRC sequence.

The nucleic acid may further include at least one 5' and/or 3' polyA sequence comprising between 5 and 25 nucleotides, e.g., 10 to 50 nucleotides (e.g., 10, 20, or 30 nucleotides), and located towards the nucleic acid's 5' end and/or towards the nucleic acid's 3' end. The 5' polyA sequence may be located 5' to the 5' iCRC sequence and/or the 3' polyA sequence is located 3' to the 3' iCRC sequence. The 5' and/or the 3' iCRC sequence may comprise 10 to 50 nucleotides, e.g., 10, 20, 30, or 40 nucleotides. Preferably, the 5' and/or the 3' iCRC sequences comprise 20 nucleotides.

The 5' UTR may be polyAx30, polyAx120, PPT19, PPT19x4, GAAAx7, or polyAx30-EMCV. The 3' UTR may be HbB1-PolyAx10, HbB1, HbB1x2, or a motif from the Elastin 3' UTR, e.g., a 3' UTR comprising the Elastin 3' UTR or a motif thereof, e.g., which is repeated twice or three times.

In embodiments, the RNA sequence may comprise at least 30 nucleotides, e.g., at least 300 nucleotides (e.g., at least 500 nucleotides). The RNA encodes a polypeptide. For example, the polypeptide is a tumor-associated antigen, a chimeric antigen receptor, a bacterial or viral antigen, a transposase or a nuclease, a transcription factor, a hormone, an scFv, a Fab, a single-domain antibody (sdAb), or a therapeutic protein. The therapeutic protein may be prepro-insulin, hypocretin, human growth hormone, leptin, oxytocin, vasopressin, factor VII, factor VIII, factor IX, erythropoietin, G-CSF, alpha-galactosidase A, iduronidase, N-acetylgalactosamine-4-sulfatase, FSH, DNase, tissue plasminogen activator, glucocerebrosidase, interferon, or IGF-1. The polypeptide may comprise an epitope for presentation by an antigen presenting cell. The polypeptide may lead to improved T-cell priming, as determined by increased production of IFN-γ, including by proliferating cells.

The 5' UTR may include an internal ribosome entry site (IRES); preferably, an encephalomyocarditis virus (EMCV) IRES or a PPT19 IRES.

The nucleic acid may include a modified nucleotide, e.g., 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, 7-deaza-adenosine, 6-azouridine, 6-azocytidine, 6-azothymidine, 5-methyl-2-thiouridine, 2-thiouridine, 4-thiouridine, 2-thiocytidine, dihydrouridine, pseudouridine, queuosine, archaeosine, naphthyl substituted naphthyl groups, an O- and N-alkylated purines and pyrimidines, N6-methyladenosine, 5-methylcarbonylmethyluridine, uridine 5-oxyacetic acid, pyridine-4-one, pyridine-2-one, aminophenol, 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, or alkylcarbonylalkylated nucleotides. Preferably, the modified base is 5-methylcytidine (5mC).

In some embodiments, the nucleic acid comprises A nucleotides, U nucleotides, G nucleotides, and C nucleotides, and wherein one or more of the following conditions apply: (i) one or more of the A nucleotides are modified adenosine analogs; (ii) one or more of the U nucleotides are modified uridine analogs; (iii) one or more of the G nucleotides are modified guanosine analogs; or (iv) one or more of the C nucleotides are modified cytidine analogs.

In some embodiments, one or more of the following conditions apply: (i) all of the A nucleotides are modified; (ii) all of the U nucleotides are modified; (iii) all of the G nucleotides are modified; or (iv) all of the C nucleotides are modified. In some embodiments, one or more of the following conditions apply: (i) approximately half of the A nucleotides are modified; (ii) approximately half of the U nucleotides are modified; (iii) approximately half of the G nucleotides are modified; or (iv) approximately half of the C nucleotides are modified.

In some embodiments, approximately half of two or more types of nucleotides are modified. For example, in some embodiments, the nucleic acid comprises C nucleotides and U nucleotides, wherein 50% of the C nucleotides are modified and 50% of the U nucleotides are modified. In some embodiments, the nucleic acid comprises C nucleotides and U nucleotides, wherein 50% of the C nucleotides are 5-methylcytidine and 50% of the U nucleotides are pseudouridine. In some embodiments, the nucleic acid comprises C nucleotides and U nucleotides, wherein 50% of the C nucleotides are 5-methylcytidine and 50% of the U nucleotides are N1-methylpseudouridine.

In some embodiments, modified nucleotide analogs are selected from the group consisting of N6-methyladenosine, 5-methylcytidine, pseudouridine, 2-thiouridine, N1-methylpseudouridine, and thienoguanosine.

In embodiments, the nucleic acid's 5' and 3' termini are not ligated, such that the nucleic acid is non-circularized.

In embodiments, the nucleic acid's 5' and 3' termini are ligated such that the nucleic acid is circularized. Such a circularized nucleic acid has greater stability (in vitro or in vivo) relative to a non-circularized nucleic acid; such a circularized nucleic acid provides greater and/or sustained polypeptide translation (in vitro or in vivo) relative to a circularized nucleic acid having CRC sequence having 100% homology. In some embodiments, the circularized nucleic acid provides greater and/or sustained polypeptide translation (in vitro or in vivo) relative to a non-circularized nucleic acid having CRC sequence and 100% homology.

The nucleic acid does not invoke an appreciable immune response in vivo.

Another aspect of the present invention is a cell comprising any above-described nucleic acid, e.g., a circularized nucleic acid. A cell comprising an above-described circularized nucleic acid may further comprise a non-circularized nucleic acid having any above-described feature. The cell may be in vitro (e.g., the cell may be of a cell culture or isolated from a biological source).

Another aspect of the present invention is a method for circularizing a nucleic acid comprising: (a) obtaining any above-described nucleic acid and in which the nucleic acid is non-circularized; and (b) ligating the 5' terminus of the nucleic acid to its 3' terminus, thereby producing a circularized nucleic acid. The method may further include converting the 5' triphosphate of the nucleic acid into a 5' monophosphate, e.g., by contacting the 5' triphosphate with RNA 5' pyrophosphohydrolase (RppH) or an ATP diphosphohydrolase (apyrase).

Alternately, converting the 5' triphosphate of the nucleic acid into a 5' monophosphate may occur by a two-step reaction comprising: (a) contacting the 5' nucleotide of the non-circularized nucleic acid with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate.

The method may further include polyadenylating the non-circularized nucleic acid molecules and separating the polyadenylated non-circularized nucleic acid molecules from the circularized nucleic acid molecules.

The ligating may occur by contacting the 5' terminus of the nucleic acid and the 3' terminus of the nucleic acid with a ligase, e.g., T4 RNA ligase. The ligating may be repeated at least one additional time, e.g., at least two additional times and at least three additional times. In embodiments, non-circularized nucleic acid molecules may be digested with an RNase, e.g., RNase R, Exonuclease T, λ Exonuclease, Exonuclease I, Exonuclease VII, T7 Exonuclease, or XRN-1; preferably, the RNase is RNase R and/or XRN-1. Non-circularized nucleic acid molecules may be digested with an RNase after the initial ligation or after the ligation is repeated at least one additional time. In embodiments, the obtained nucleic acid is synthesized by in vitro transcription (IVT).

Yet another aspect of the present invention is a circularized nucleic acid produced by an above-described method.

An aspect of the present invention is a composition comprising any above-described circularized nucleic acid. The compositions are useful in vaccinating a subject, in producing a chimeric antigen receptor or T-cell receptor, in treating cancer, or for in vivo protein replacement therapy.

The composition may further comprise a non-circularized nucleic acid having any above-described feature.

In some aspects, the application provides techniques for increasing therapeutic effectiveness of a circular nucleic acid. The inventors have discovered that contamination of circularized RNA with unwanted linear RNA can lead to unwanted biological response—e.g., e.g. through induction of innate immunity caused by linear RNA reacting with the immune system. Therefore, it becomes essential to prepare circular RNA for human therapeutic applications in the purest form possible. To these ends, the application provides methods for generating and isolating the circular form for therapeutic applications.

In yet other aspects, the application provides techniques for selectively enriching, isolating, and/or purifying a circularized RNA form relative to a linear RNA form. The inventors have discovered that such selective modifications can be made to enhance purity of a desired circularized product. For example, such selective modifications include selectively modifying the size of one form relative to another to enhance separation by size purification means, selectively modifying the charge of one form over another to enhance separation by ion chromatography and electrophoretic means, selectively tagging a linear form for degradation, and selectively modifying one form to comprise a capture moiety that permits the capture of that form.

Any of the above-described aspects or embodiments can be combined with any other aspect or embodiment as described herein.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1A illustrates a general methodology for preparing a circular RNA. FIG. 1B illustrates a methodology that involves a one-step 5'-phosphate modification. FIG. 1C illustrates a methodology that includes a 3' polyadenylation.

FIG. 2A depicts a construct showing sequence motifs that make up the mRNA used for HPLC isolation and peak characterization. As shown, a PEST sequence downstream of the NLuc coding sequence acts as a destabilizing element, which confers a protein half-life of approximately 2 hours. The PEST sequence can be used to demonstrate that protein detected at later time points must have been translated at later time points, providing a surrogate for persistent mRNA. FIG. 2B is a TapeStation analysis (Agilent) of the 4 different forms of mRNA used in the example (L: Linear mRNA (−polyadenylation); L+A: Linear mRNA (+polyadenylation); C: Impure Circular mRNA (−polyadenylation); C+A: Impure Circular mRNA (+polyadenylation). FIG. 2C depicts chromatograms of the 4 mRNAs run on HPLC. As shown, a complete peak shift in the L+A sample and an incomplete shift (2 peaks) in the C+A sample was observed. The "linear" and "circular" peaks shown in the chromatograms were collected and assayed for protein expression via NLuc activity (FIG. 2D) and mRNA expression kinetics via qPCR (FIG. 2E) at 6, 24, and 72 hours post-transfection. Treatment of the pre-HPLC mixture of linear and circular mRNA with polyA polymerase can thus enable separation of the linear and circular fractions, which would otherwise have the same length and therefore co-elute. The polymerase extends the length of the linear mRNA but cannot modify the circular mRNA, which has no 3' end.

As shown in FIG. 3D, EMCV consistently produced the highest level of protein across multiple cell lines. To confirm that the protein produced from these constructs was IRES-derived, cap-dependent translation was inhibited in in vitro reticulocyte translation reactions through the addition of excess cap analog. A cartoon depiction of this assay is shown in FIG. 3E. Purified circular mRNA from the constructs described in FIG. 3C were used as templates in rabbit reticulocyte ("retic") lysate translation reactions, which were or were not spiked with excess cap analog (1 mM). The excess cap enhanced protein expression for the EMCV-NLuc mRNA but reduced protein expression for the cap-dependent PPT19 and insulin 5' UTR constructs (FIG. 3F). Similar tests in the retic system were performed using mRNA constructs with a GFP coding sequence (FIG. 3G). Commercially available eGFP mRNA (TriLink Biotechnologies) was used as a control. In this experiment, mRNA containing the EMCV IRES maintained its translation capacity, whereas mRNA purchased from TriLink or transcribed from a template containing the insulin 5' UTR exhibited significant drops in protein expression. As shown, commercial and linear forms of RNA showed significant reduction in protein production upon addition of cap analog, while circular RNA maintained its level of protein production.

FIGS. 4A-4C depict examples of CRCs that are duplexed at ligation temperatures but not at body temperature. FIG. 4A is a table containing a Complement-Reverse Complement ("CRC") construct list. FIG. 4B depicts cartoon representations showing each CRC's predicted secondary structure. FIG. 4C is a table showing the predicted conformations at 16° C. and 37° C. for the corresponding structures in FIG. 4B.

FIG. 5A is a gel showing linear and circular RNA at different stages of the circularization procedure and under different conditions. FIG. 5B is a polyacrylamide gel analysis following 5'-monophosphate end preparation (AP: Antarctic phosphatase, rSAP: recombinant shrimp alkaline phosphatase, CIP: calf intestinal phosphatase, PNK: polynucleotide kinase, RppH: RNA pyrophosphohydrolase, GMP: guanosine-5'-monophosphate, GTP: guanosine-5'-triphosphate)

FIG. 6A depicts a set of conditions for HPLC purification (top, boxed area) and an optimized solvent gradient for separating RNAs (bottom) (Solvent A: 0.1 M TEAA, Solvent B: 0.1 M TEAA+25% Acetonitrile). FIG. 6B is an RNA Century ladder (Life Technologies) showing accurate separation. FIG. 6C is an overlay of chromatograms of RNase R-treated RNA upon initial runs on the HPLC column, and FIG. 6D shows the results following a re-run on the HPLC column. FIG. 6E depicts results from flow cytometry experiments measuring translation of pre- and post-HPLC purified circular mRNA in HEK293T cells. The mRNA-induced immune response was evaluated by measuring induction of IFN-β (FIG. 6F) and RIG-I (FIG. 6G) by qPCR FIG. 7A is a plot that illustrates degradation of linear RNA following RNase R treatment. FIG. 7B depicts a gel analysis confirming the presence and purity of circular RNA product. FIG. 7C shows RT-PCR results confirming ligation. FIG. 7D is an illustration of an example circular RNA construct, which demonstrates that divergent primers can be used to sequence across the 5'-3' junction for purposes of confirming ligated product.

FIG. 8A depicts the amount of remaining linear RNA following exposure to RNase R under varied conditions. FIG. 8B depicts the amount of remaining linear RNA following RNase R exposure using constructs having varied 3' UTRs. FIG. 8C depicts the amount of remaining linear RNA following RNase R exposure using linear RNA (+/−poly(A) tail and/or +/−CRC).

FIG. 9A is a diagram of the predicted secondary structure and sequence of the 5' and 3' ends of an example RNA construct (SEQ ID NOS 94 and 95) when the optimized CRC is included. FIG. 9B illustrates constructs designed for use in the experiments. FIG. 9C is an image of a gel confirming that the desired circular RNA was produced. FIG. 9D depicts an evaluation of circularization efficiency of a panel of constructs. FIG. 9E depicts an evaluation of translation efficiency in HEK293T cells. FIG. 9F depicts an evaluation of cytokine induction using different constructs.

FIG. 11A is diagram of a target mRNA and its corresponding amplicons when using inward- and outward-oriented primers. FIG. 11B depicts results from RT-PCR with HepG2 cells were transfected with commercial eGFP or circular mRNA. FIG. 11C illustrates the general protocol for in vivo experiments measuring linear (FIG. 11D) and circular (FIG. 11E) mRNA levels.

FIG. 12A is a plot showing protein expression kinetics from circular mRNA versus linear mRNA. FIG. 12B is a timeline followed for protein expression assays. FIG. 12C depicts protein levels of circular mRNA over an 8-day period.

FIG. 14A is a diagram of a codon-optimized mouse erythropoietin mRNA having an EMCV 5' UTR and a poly(A)x50 3' UTR. FIG. 14B is an image of a gel confirming size and purity of the RNA. FIG. 14C depicts results from RT-PCR confirming successful ligation. FIG. 14D depicts confirmation of RNA translation in HEK293T cells. FIG. 14E depicts optimization of Epo mRNA injected intravenously into BALB/c mice.

FIG. 15A depicts protein expression levels measured in HepG2 cells. FIG. 15B depicts protein expression levels measured in PMBCs. FIG. 15C depicts mRNA levels measured in HepG2 cells. FIG. 15D depicts mRNA levels measured in PMBCs. FIG. 15E depicts a functional readout (relative reticulocyte %) for mEpo protein production following injection of mRNA into mice.

DETAILED DESCRIPTION OF THE INVENTION

Figure 1A:
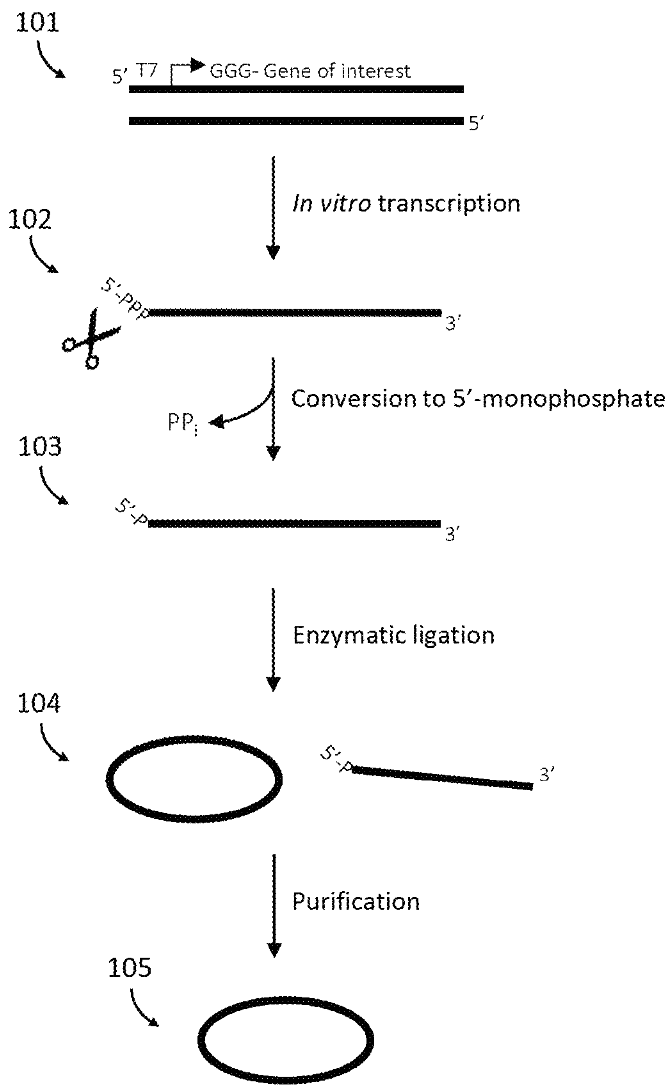
FIGS. 1A-1C depict example workflows for preparing circular nucleic acids.

The invention provides circularized nucleic acids (e.g. RNA), compositions comprising circularized nucleic acids, methods of circularizing nucleic acids, and methods of using circularized nucleic acids. The nucleic acids, compositions, and methods are based upon the previous observation that circularization is more dependent on the proximity and availability of the free ends of the RNA than the size of the RNA construct. Specifically, the present invention is an improvement of the inventions described in WO 2016/197121, the contents of which is incorporated by reference in its entirety.

RNA-based therapy affords benefits of gene therapy while remaining transient. Because RNA may be used as a transient, cytoplasmic expression system, RNA-based therapies can be applied in quiescent and/or slowly proliferating cells (i.e., muscle cells and hepatocytes). However, the instability of RNA, which is largely attributable to exonuclease-mediated degradation, has limited the clinical translation of RNA. In particular, the majority of RNA is degraded by exonucleases acting at both ends or at one end of the molecule after deadenylation and/or decapping. The sub-optimal stability of linear RNA remains an unresolved issue hindering the feasibility of RNA-based therapies. The majority of efforts to stabilize RNA have focused on linear RNA and modification thereof.

Linear RNA is prone to exonuclease degradation from the 5' to 3' end and from the 3' to 5' end, whereas circularized RNA transcripts have increased serum stability and/or intracellular stability, at least in part because there are no ends available to serve as substrates for exonucleases. However, there are currently no effective methods for producing or purifying large-scale circularized RNA suitable for therapeutic purposes, particularly for sequences that are longer than 0.5 kb.

In contrast, the invention described in WO 2016/197121 possessed several new and advantageous features overcoming prior disadvantages encountered with other methods of creating circularized RNA. Specifically, the invention described in WO 2016/197121 had the following advantages: 1) an optimized method for generating circularized RNA in higher yields than previously obtained; 2) circularized RNA encoding therapeutic proteins; 3) circularized RNA having improved stability (in solution, in cells, and in vivo); 4) longer circularized RNA molecules than previously obtained; 5) use of circularized RNA for therapeutic gene transfer into cells; 6) use of circularized RNA for improved vaccination; and 7) use of circularized non-coding RNA for binding to endogenous target RNAs and/or RNA-binding proteins.

The invention described in WO 2016/197121 was based upon the identification of motifs in the 5' and 3' untranslated regions of the transcript that enhance circularization efficiency and/or enable and enhance cap-independent translation. Specifically, it was described that complement-reverse complement (CRC) sequence motifs together with random nucleotides (e.g., nucleotides of a tail sequence) at the 5' and 3' ends of a desired RNA facilitates enzymatic circularization of RNA. While CRC sequence motifs greatly enhanced circularization efficiency, an unexpected problem is that the double stranded regions caused by the CRC sequence motifs can be recognized by the pattern recognition receptors of the immune system that consequently lead to decreased translation. To solve this problem, it was discovered that the addition of one or more point mutations into the CRC sequence motif can reduce the melting temperature such that the double stranded motif is intact during ligation temperatures to facilitate the circularization of the RNA but disassociates at body temperature. This provides the benefit of bringing the two ends of the mRNA molecule together (with a retarded off-rate) during ligation while bypassing the immune recognition and translation inhibition the CRC sequence motif can induce once the circular mRNA is introduced into cells.

Circularized RNA

The present invention is based upon 5' and 3' motifs that allow highly efficient enzymatic circularization of RNA. Specifically, complement-reverse complement (CRC) sequence motifs with one or more point mutations (i.e., nucleotide mismatches). These modified CRC motifs are referred to herein as imperfect CRCs or iCRCs.

Accordingly, the invention provides a nucleic acid (DNA or RNA) comprising a 5' imperfect complement-reverse complement (iCRC) sequence; a 5' untranslated region (UTR) sequence; an RNA sequence (e.g., an open reading frame); a 3' untranslated region (UTR) sequence; and a 3' imperfect CRC sequence along with random nucleotides on the distal ends of the imperfect CRC motifs (e.g., 5' and 3' tail sequences). For example, in some embodiments, the invention provides a nucleic acid (DNA or RNA) comprising in 5' to 3' order: a 5' iCRC sequence (e.g., a 5' tail sequence and a 5' sequence that hybridizes to the 3' iCRC motif under ligation reaction conditions); a 5' UTR sequence; an RNA sequence (e.g., an open reading frame); a 3' UTR sequence; and a 3' iCRC sequence (e.g., a 3' sequence that hybridizes to the 5' iCRC motif under ligation reaction conditions and a 3' tail sequence). The RNA sequence may be an RNA sequence capable of being translated into a polypeptide; the RNA sequence may comprise an open reading frame; the RNA sequence may be a non-coding RNA, e.g., an RNA that is a reverse complement of an endogenous RNA, i.e., an mRNA, a miRNA, a tRNA, an rRNA, or a lncRNA; or the RNA sequence may be capable of binding to an RNA-binding protein (RBP). When the RNA sequence binds an RBP, the nucleic acid of the present invention prevents the RBP from binding to its canonical linear RNA binding partner.

In a nucleic acid, the 5' iCRC sequence and/or the 3' iCRC sequence has one, two, three, four, five, six, seven, eight, nine, ten, or more nucleotide mismatches. In some embodiments, the number of mismatches in the base-pairing of the 5' iCRC sequence and the 3' iCRC sequence are such that the sequences are at least 70% and less than 100% complementary. For example, in some embodiments, the 5' and 3' iCRC sequences are between 70% and 95%, between 70% and 90%, between 70% and 80%, between 75% and 95%, between 75% and 90%, between 80% and 95%, or between 80% and 90% complementary.

The one or more nucleotide mismatches are such that the 5' iCRC sequence and the 3' iCRC are not 100% complementary. The mismatches result in the 5' iCRC and the 3' iCRC having an annealing temperature ($T_a$) less than 25° C. and/or a melting temperature ($T_m$) greater than 25° C. Preferably, the $T_a$ is above the ligation temperature of about 16° C. and the $T_m$ is below body temperature (about 37° C.). To ensure adequate conditions—that is, that the 5' iCRC and 3' iCRC are predominantly annealed at a temperature at which ligation can occur and that the 5' iCRC and 3' iCRC are melted when introduced into the body—one preferably operates comfortably within a temperature range of between 16° C. and 37° C. For example, as mentioned above, selecting a $T_m$ of 25° C. will ensure that the 5' iCRC and 3' iCRC will be preferentially melted when introduced into the body and exposed to a temperature above 25° C., and that the 5' iCRC and 3' iCRC will be preferentially annealed during a ligation reaction performed at 20° C. Accordingly, in some embodiments, ideal melting temperatures for iCRC constructs are between 20° C. and 34° C., more preferably between 23° C. and 30° C., or between 25° C. and 28° C.

Algorithms and methods for calculating $T_m$ are well known in the art and include, without limitation, methods of experimentally determining $T_m$ (e.g., by measuring the absorbance change of the oligonucleotide sequence with its complement as a function of temperature, and determining the halfway point on a plot of absorbance versus time) and methods of theoretically determining $T_m$ (e.g., the nearest neighbors method, as described in: Freier S M, Kierzek R, Jaeger J A, Sugimoto N, Caruthers M H, Neilson T, & Turner D H (1986). Improved free-energy parameters for predictions of RNA duplex stability. Proc Natl Acad Sci, 83, 9373-9377; and Breslauer K J, Frank R, Blocker H, & Marky L A (1986). Predicting DNA duplex stability from the base sequence. Proc Natl Acad Sci, 83, 3746-3750). Additional methods of determining $T_m$ are known in the art, e.g., as described in: Dumousseau M., Rodriguez N., Juty N., Le Novère N. (2012) MELTING, a flexible platform to predict the melting temperatures of nucleic acids. BMC Bioinformatics, 13: 101; on-line at: https://www.ebi.ac.uk/biomodels/tools/melting/; Kibbe W A. 'OligoCalc: an online oligonucleotide properties calculator'. (2007) Nucleic Acids Res. 35(webserver issue): May 25; and on-line at: http://biotools.nubic.northwestern.edu/OligoCalc.html.

The 5' or 3' iCRC sequence comprises 10 to 50 nucleotides, e.g., 10, 20, 30, 40, or 50 nucleotides. In some embodiments, the 5' and/or 3' iCRC sequence is selected from Table 1:

TABLE 1

Imperfect CRC sequence list with predicted Tm's falling between 25-37° C.

| # | 5' CRC (5' → 3' Orientation) | SEQ ID NO | 3'CRC (5' → 3' Orientation) | SEQ ID NO | CRC Length | # Mutation | Melting Temp (C.) |
|---|---|---|---|---|---|---|---|
| 1 | GCACGAATTGCACAA TCGGTACGTTCGAGT | 1 | ACTCGAAAGAACAGA ATGTACAAATCGTGC | 8 | 30 | 6 | 37 |
| 2 | GTTACGTACCAACAC GTTATTGCCGTCGGT | 2 | ACCGAAGGCATTAAA GTGATGGAACATAAC | 9 | 30 | 6 | 36.31 |
| 3 | GTTACGTACCAACAC GTTATTGCCGTCGGT | 2 | ACCGTCGGAAATGAC GTATTGATTCGTAAC | 10 | 30 | 7 | 35.45 |
| 4 | GTTACGTACCAACAC GTTATTGCCGTCGGT | 2 | ACCGTCGGAAATCAC GTATTGATAGGTAAC | 11 | 30 | 6 | 34.97 |

TABLE 1-continued

Imperfect CRC sequence list with predicted Tm's falling between 25-37° C.

| # | 5' CRC (5' → 3' Orientation) | SEQ ID NO | 3'CRC (5' → 3' Orientation) | SEQ ID NO | CRC Length | # Mutation | Melting Temp (C.) |
|---|---|---|---|---|---|---|---|
| 5 | GCACGAATTGCACAA TCGGTACGTTCGAGT | 1 | ACTCAAAAGTAACGA ATGTGAAATTAGTGC | 12 | 30 | 6 | 34.4 |
| 6 | GTTACGTACCAACAC GTTATTGCCGTCGGT | 2 | ACCGACAGCAACAAC CTGCTGGTACATAAC | 13 | 30 | 5 | 33.71 |
| 7 | GCACGAATTGCACAA TCGGTACGTTCGAGT | 1 | ACTCAAGCGTACTGA GTGTGGAACTAGTGC | 14 | 30 | 7 | 33.48 |
| 8 | GTTACGTACCAACAC GTTATTGCCGTCGGT | 2 | ACCGCCGGAAATGAC GTATTGATAGGTAAC | 15 | 30 | 6 | 32.98 |
| 9 | GTTACGTACCAACAC GTTATTGCCGTCGGT | 2 | ACCGTCGGAAATTAA GTATTGATACGTAAC | 16 | 30 | 6 | 32.42 |
| 10 | GCACGAATTGCACAA TCGGTACGTTCGAGT | 1 | ACTCAAACATAACGA TAGTGCAAATAGTGC | 17 | 30 | 6 | 32.4 |
| 11 | GCACGAATTGCACAA TCGGTACGTTCGAGT | 1 | ACTCAAGCGTACGGA ATGTGGAAATGGTGC | 18 | 30 | 7 | 30.8 |
| 12 | GCACGAATTGCACAA TCGGTACGTTCGAGT | 1 | ACTCCAACATACAGA TAGTGCAAATAGTGC | 19 | 30 | 6 | 30.45 |
| 13 | GTTACGTACCAACAC GTTATTGCCGTCGGT | 2 | ACCGCCGGAAATCAC GTATTGATAGGTAAC | 20 | 30 | 6 | 30.37 |
| 14 | GCACGAATTGCACAA TCGGTACGTTCGAGT | 1 | ACTCAAACATACAGA TAGTGCAAATAGTGC | 21 | 30 | 6 | 29.49 |
| 15 | GTTACGTACCAACAC GTTATTGCCGTCGGT | 2 | ACCGACAGCAACAAC TTGCTGCTATGTAAC | 22 | 30 | 6 | 27.9 |
| 16 | GCACGAATTGCACAA TCGGTACGTTCGAGT | 1 | ACTCAAAAGTAACGA ATGTGAAAATAGTGC | 23 | 30 | 7 | 26.94 |
| 17 | GTTACGTACCAACAC GTTATTGCCGTCGGT | 2 | ACCGACAGCAACAAC CTGCTGCTATGTAAC | 24 | 30 | 5 | 25.53 |
| 18 | GCACGAATTGCACAA TCGGT | 3 | ACCGATTGAGCTATA CGTGC | 25 | 20 | 3 | 36.04 |
| 19 | TGGCTGCACGAATTG CACAA | 4 | TTGTACAATTCATGCA GCCA | 26 | 20 | 2 | 36.2 |
| 20 | GCACGAATTGCACAA TCGGT | 3 | ACCGATTGTCCAATCC GTGC | 27 | 20 | 2 | 35.35 |
| 21 | TGGCTGCACGAATTG CACAA | 4 | TTGTGGAATCCGTGG AGCCA | 28 | 20 | 3 | 35.25 |
| 22 | GTACGTGGCTGCACG AATTG | 5 | CAATACGTGCCGCCA GGTAC | 29 | 20 | 3 | 35.06 |
| 23 | GCACGAATTGCACAA TCGGT | 3 | ACCGGTTGTGAAATT GGTGC | 30 | 20 | 3 | 34.54 |
| 24 | TGGCTGCACGAATTG CACAA | 4 | TTGTCCAATTCCTGCA GCCA | 31 | 20 | 2 | 33.31 |
| 25 | GCACGAATTGCACAA TCGGT | 3 | ACCGCTTATGCACTTC GTGC | 32 | 20 | 3 | 32.87 |
| 26 | GTACGTGGCTGCACG AATTG | 5 | CAATTAGTGAAGCCT CGTAC | 33 | 20 | 3 | 31.99 |
| 27 | GCACGAATTGCACAA TCGGT | 3 | ACCGACTGTGCCATTG GTGC | 34 | 20 | 3 | 31.8 |
| 28 | GCACGAATTGCACAA TCGGT | 3 | ACCGTTTGTTCAATTT GTGC | 35 | 20 | 3 | 30.61 |

TABLE 1-continued

Imperfect CRC sequence list with predicted Tm's falling between 25-37° C.

| # | 5' CRC (5' → 3' Orientation) | SEQ ID NO | 3'CRC (5' → 3' Orientation) | SEQ ID NO | CRC Length | # Mutation | Melting Temp (C.) |
|---|---|---|---|---|---|---|---|
| 29 | GCACGAATTGCACAA TCGGT | 3 | ACCGGTTGTACAATCC GTGC | 36 | 20 | 3 | 29.33 |
| 30 | GCACGAATTGCACAA TCGGT | 3 | ACCGGTTGTCCAATCC GTGC | 37 | 20 | 3 | 27.42 |
| 31 | GCACGAATTGCACAA TCGGT | 3 | ACCGAATGAGCTATA CGTGC | 38 | 20 | 4 | 26.57 |
| 32 | GTACGTGGCTGCACG AATTG | 5 | CAATTCATGCATCCAG GTAC | 39 | 20 | 3 | 26.36 |
| 33 | TGGCTGCACGAATTG CACAA | 4 | TTGTACACTTCATGCA GCCA | 40 | 20 | 3 | 26.28 |
| 34 | GTACGTGGCTGCACG AATTG | 5 | CAATACGTGGAGACA AGTAC | 41 | 20 | 4 | 25.69 |
| 35 | GCACGAATTGCACAA | 6 | TTGTCCAATTCGTGC | 42 | 15 | 1 | 26.15 |
| 36 | TGGCTGCACGAATTG | 7 | CAATACGTGCAGCCA | 43 | 15 | 1 | 36.17 |
| 37 | GCACGAATTGCACAA | 6 | TTGTGCAATGCGTGC | 44 | 15 | 1 | 35.47 |
| 38 | TGGCTGCACGAATTG | 7 | CAATTCGAGCAGCCA | 45 | 15 | 1 | 35.19 |
| 39 | GCACGAATTGCACAA | 6 | TTGTGSAATTCGTGC | 46 | 15 | 1 | 34.39 |
| 40 | GCACGAATTGCACAA | 6 | TTGTGCAATACGTGC | 47 | 15 | 1 | 34.13 |
| 41 | GCACGAATTGCACAA | 6 | TTGTGCAAATCGTGC | 48 | 15 | 1 | 33.93 |
| 42 | TGGCTGCACGAATTG | 7 | CAATTAGTGCAGCCA | 49 | 15 | 1 | 33.39 |
| 43 | TGGCTGCACGAATTG | 7 | CAATTCGTGAAGCCA | 50 | 15 | 1 | 33.21 |
| 44 | TGGCTGCACGAATTG | 7 | CANTCCGTGCAGCCA | 51 | 15 | 1 | 31.93 |
| 45 | GCACGAATTGCACAA | 6 | TTGTGCAATTAGTGC | 52 | 15 | 1 | 31.44 |
| 46 | GCACGAATTGCACAA | 6 | TTGTGCGAGTCGTGC | 53 | 15 | 2 | 30.22 |
| 47 | TGGCTGCACGAATTG | 7 | CAATTCGTACAGCCA | 54 | 15 | 1 | 30.08 |
| 48 | GCACGAATTGCACAA | 6 | TTGTGCCASTCGTGC | 55 | 15 | 2 | 27.94 |
| 49 | TGGCTGCACGAATTG | 7 | CAATTCGAGCTGCCA | 56 | 15 | 2 | 27.34 |
| 50 | TGGCTGCACGAATTG | 7 | CAATTCGCGCTGCCA | 57 | 15 | 2 | 25 |

The nucleic acid further includes a random nucleotide sequence (e.g., a tail sequence) at the 5' end and the 3' end. The 5' random nucleotide sequence (e.g., the 5' tail sequence) is upstream of the 5' iCRC sequence, and the 3' random nucleotide sequence (e.g., the 3' tail sequence) is downstream of the 3' iCRC sequence.

The 5' tail sequence and the 3' tail sequence are present in the constructs provided herein to facilitate ligation. As would be understood by a person of ordinary skill in the art, ligation (e.g., 5' to 3' end ligation) will proceed more rapidly if the ends are within a ligatable distance relative to one another provided that they are not hybridized. As iCRC sequences are hybridized, ligation between a nucleotide of each sequence is not favored. Therefore, flexible ends are provided as tails to permit joining of so-called “free” ends to one another.

In practice, it has been found that these free ends are approximately the same length and substantially non-complementary. In some embodiments, each tail sequence can comprise between 10 and 20 nucleotides if both are of approximately the same length. One can of course achieve the same outcome using tails of differing lengths in a single construct, e.g., by having one short tail and a longer tail having a degree of flexibility sufficient to place the ends in a ligatable proximity relative to one another. The arrangements are too numerous to list individually, but the following lists examples of 5' and 3' tail sequences.

In some embodiments, it is preferred that the 5' tail sequence and the 3' tail sequence do not hybridize under ligation reaction conditions. Accordingly, in some embodiments, appropriate tail sequences and iCRC sequences should be such that, at the desired ligation temperature, the 5' and 3' tail sequences will be preferentially melted while the 5' and 3' iCRC sequences will be preferentially annealed. It should be appreciated, however, that ligation temperature considerations may be inconsequential where the 5' and 3' tail sequences are substantially non-complementary.

In some embodiments, a DNA template used for in vitro transcription of the constructs described herein includes the 5' and 3' tail sequences. Many in vitro transcription methodologies known in the art utilize one of several RNA polymerase enzymes (e.g., T7 RNA polymerase, T3 RNA polymerase, and SP6 RNA polymerase) that require at least one G nucleotide at the 5'-most base position to function as a priming nucleotide to initiate transcription. As such, in some embodiments, the 5' tail sequence comprises a G nucleotide at the 5'-most base position. With certain of these polymerases, it has been observed that efficiency of transcription is increased greatly when two or three G nucleotides are present at the 5'-most base positions. Accordingly, in some embodiments, the 5' tail sequence comprises between one and three G nucleotides at the 5'-most base positions.

In some embodiments, the 5' tail sequence is a sequence of Formula (I):

$$5'\text{—}G_{X1}\text{-}N_{X2}\text{—}$$

(I), wherein:

each G is independently an unmodified or chemically modified G nucleotide;

each N is independently an unmodified or chemically modified nucleotide;

X1 is an integer from 1 to 3, inclusive; and

X2 is an integer from 1 to 25, inclusive.

In some embodiments, X2 is at least 3; and each N at base positions 1-3 is independently an unmodified or chemically modified A or T/U nucleotide.

In some embodiments, X2 is at least 6; and each N at base positions 4-6 is independently an unmodified or chemically modified C, G, or A nucleotide.

In some embodiments, each N is an unmodified or chemically modified A nucleotide.

In some embodiments, each N is an unmodified or chemically modified C nucleotide.

In some embodiments, the 5' tail sequence is a sequence of Formula (II):

$$\text{—}[N]_{X3}\text{—}3'$$

(II), wherein:

each [N] is independently an unmodified or chemically modified nucleotide; and

X3 is an integer from 1 to 30, inclusive.

In some embodiments, X3 is at least 3; and each [N] at base positions 1-3 is independently an unmodified or chemically modified C or G nucleotide.

In some embodiments, X3 is at least 6; and each [N] at base positions 4-6 is independently an unmodified or chemically modified A or T/U nucleotide.

In some embodiments, X3 is at least 9; and each [N] at base positions 4-9 is independently an unmodified or chemically modified A or T/U nucleotide.

In some embodiments, each [N] is an unmodified or chemically modified A nucleotide.

In some embodiments, each [N] is an unmodified or chemically modified C nucleotide.

In some embodiments, a 5' and 3' tail sequence is selected from Table 2:

TABLE 2

Tail Sequence List (Regions that flanks CRC motif)

| # | 5' Tail | SEQ ID NO | 3' Tail | SEQ ID NO | Length |
|---|---|---|---|---|---|
| 1 | GGGAATCGAC | 58 | CGGAATATAG | 70 | 10 |
| 2 | GGGAAAAAAA | 59 | AAAAAAAAAA | 71 | 10 |
| 3 | GGAAAAAAAA | 60 | AAAAAAAAAA | 71 | 10 |
| 4 | GAAAAAAAAA | 61 | AAAAAAAAAA | 71 | 10 |
| 5 | GCCCCCCCCC | 62 | CCCCCCCCCC | 72 | 10 |
| 6 | GCCCCCCCCC | 62 | AAAAAAAAAA | 71 | 10 |
| 7 | GGGAATCGACTACAG | 63 | CGGAATATAGAAGCA | 73 | 15 |
| 8 | GGGAAAAAAAAAAAA | 64 | AAAAAAAAAAAAAAA | 74 | 15 |
| 9 | GGAAAAAAAAAAAAA | 65 | AAAAAAAAAAAAAAA | 74 | 15 |
| 10 | GAAAAAAAAAAAAAA | 66 | AAAAAAAAAAAAAAA | 74 | 15 |
| 11 | GCCCCCCCCCCCCCC | 67 | CCCCCCCCCCCCCCC | 75 | 15 |
| 12 | GCCCCCCCCCCCCCC | 67 | AAAAAAAAAAAAAAA | 74 | 15 |
| 13 | GGGAATCGACTACAG GAGGA | 68 | CGGAATATAGAAGCA TAAGA | 76 | 20 |
| 14 | GGGAAAAAAAAAAAA AAAAA | 69 | AAAAAAAAAAAAAAA AAAAA | 77 | 20 |
| 15 | GGAAAAAAAA AAA | 60 | AAAAAAAAAAAAAAA AA | 77 | 20 |
| 16 | GAAAAAAAAA | 61 | AAAAAAAAAAAAAAA AAAAA | 77 | 20 |
| 17 | GCCCCCCCCC | 62 | CCCCCCCCCCCCCCC CCCCC | 78 | 20 |
| 18 | GCCCCCCCCC | 62 | AAAAAAAAAAAAAAA AAAAA | 77 | 20 |

Each random nucleotide sequence (e.g., a tail sequence) is between about 5 and 50 nucleotides, e.g., 10, 15, 20, or 25 nucleotides.

Rather than having random nucleotide sequences, a nucleic acid may have one or two polyA sequences, with the polyA sequences being upstream of a 5' CRC and/or downstream of a 3' CRC and at the nucleic acid's end(s).

Each polyA sequence is between about 5 and 50 nucleotides, e.g., 10, 15, 20, 25, or 30 nucleotides.

Figures 4B, 4C:
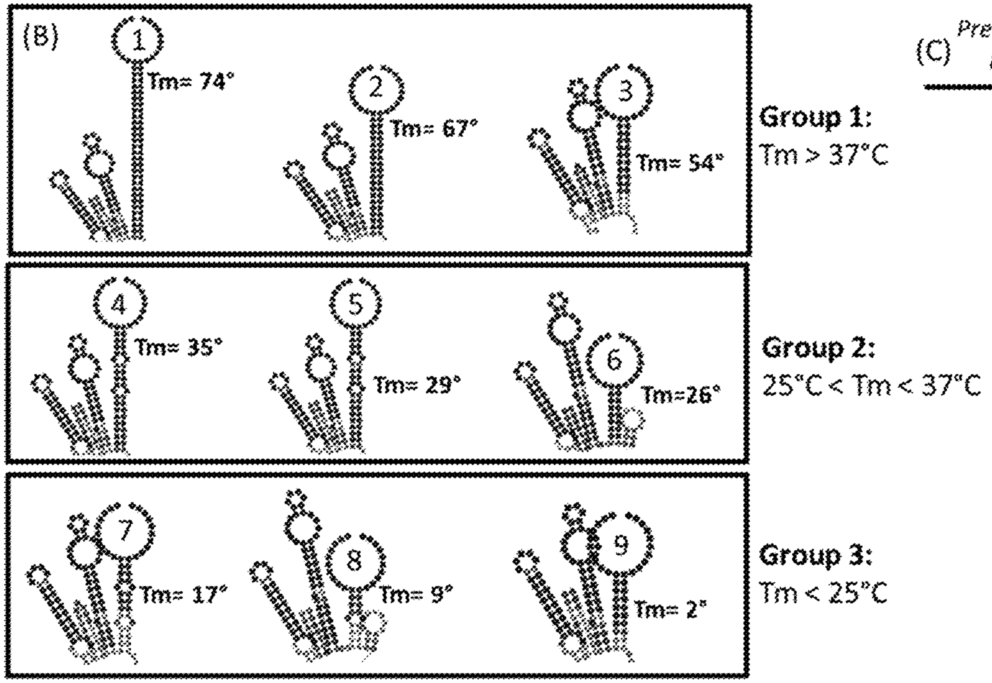

Preferred 5' or 3' iCRC sequences are exemplified in FIG. 4A.

The 5' UTR is any UTR known in the art. For example, the 5' UTR is polyAx30, polyAx120, HCV, CrPV, EMCV, or polyAx30-EMCV. Preferably, the 5' UTR is EMCV. Any known 3' UTR may be used in the present invention; examples include HbB1-PolyAx10, HbB1, HbB1x2, or an Elastin-derived 3' UTR (e.g., a motif from the Elastin 3' UTR). Preferably, the 3' UTR is an Elastin-derived 3' UTR. Multiple tandem copies (e.g., 2, 3, 4, or more) of a UTR may be included in a nucleic acid (e.g., more than one copy of a motif from the Elastin 3' UTR and more than one copy of the EMCV 5' UTR). As used herein, the number after an "x" in a UTR's name refers to the number of copies of the UTR (or motif thereof). As an example, an Elastin 3' UTR (or a motif thereof) that is repeated twice is referred to as Elastinx2 and an Elastin 3' UTR (or a motif thereof) that is repeated three times is referred to as Elastinx3.

In accordance with the invention, very large target RNA sequences are able to be circularized. In a typical circularized RNA, an open reading frame would encode a single therapeutic protein. In other circularized RNA, however, the open reading frame can encode two or more therapeutic proteins. For example, therapeutically active peptides are intended to be encoded by an open reading frame of an RNA sequence provided herein. Additionally, very large polypeptides are intended to be encoded, for example, those requiring the encoding RNA sequence to be between 15 and 10000 or more nucleotides in length. More typically, the RNA sequence is between 15 and 6000 nucleotides in length, e.g., between 30 and 5000, between 50 and 4000, between 100 and 3000, between 200 and 3000, between 400 and 3000, between 600 and 3000, between 800 and 2000, between 900 and 2000, or between 1000 and 2000.

In some instances, the RNA sequence encodes a much longer molecule, such as a chimeric protein, which would require a much longer open reading frame. In some embodiments, chimeric proteins can include two or more (e.g., 2, 3, 4, 5, or more) therapeutic proteins which can be encoded in a single RNA sequence. However, in some instances, the RNA sequence can encode a relatively small molecule, such as a polypeptide or a therapeutic RNA molecule that does not require translation to provide a therapeutic benefit. As such, the 5' and 3' motifs identified by the inventors allow any size target RNA to be circularized. The RNA sequence is at least 15, 30, 50, 100, 200, 300, 400, 500, 600, 700, 800, 900, 1000, 2000, 3000, 4000, 5000, 6000, 7000, 8000, 9000, 10000, or more nucleotides in length.

The RNA (e.g., mRNA) sequence may encode any protein of interest, for example the target RNA encodes for a hormone, an antibody such as scFv, single-domain antibody (also known as a nanobody), cytokine, intracellular protein, extracellular protein, tumor-associated antigen, chimeric antigen receptor, bacterial antigen, viral antigen, transposase, nuclease, or transcription factor. The RNA may encode a therapeutic polypeptide, e.g., preproinsulin, hypocretin, human growth hormone, leptin, oxytocin, vasopressin, factor VII, factor VIII, factor IX, erythropoietin, G-CSF, alpha-galactosidase A, iduronidase, N-acetylgalactosamine-4-sulfatase, FSH, DNase, tissue plasminogen activator, glucocerebrosidase, interferon alpha, interferon beta, interferon gamma, or IGF-1. The translated protein would have endogenous post-translational modifications and could be retained intracellularly or secreted. The RNA sequence may encode a polypeptide that comprises an epitope for presentation by an antigen presenting cell. The polypeptide may lead to improved (e.g., more efficient and greater quantity) T cell priming, as determined by increased production of IFN-γ, including by proliferating cells.

The RNA sequence may be an RNA that is a reverse complement of an endogenous RNA, i.e., an mRNA, a miRNA, a tRNA, an rRNA, or a lncRNA; by "endogenous" is meant an RNA that is naturally transcribed by a cell. An RNA sequence that is a reverse complement may be referred to as a "non-coding RNA" since it does not encode a polypeptide. When an RNA sequence of the present invention binds an endogenous RNA, the endogenous RNA's function may be blocked or reduced; for example, when the endogenous RNA is an miRNA, the RNA sequence of the present invention prevents the miRNA from binding to its target mRNAs.

The RNA sequence may be capable of binding to an RNA-binding protein (RBP). When the RNA sequence binds an RBP, the nucleic acid of the present invention prevents the RBP from binding to its canonical linear RNA binding partner. Non-limiting examples of RBPs are found at the World Wide Web (www) at rbpdb.ccbr.utoronto.ca.

A circularized nucleic acid will have greater stability (i.e., more resistant to degradation or enzymatic digestion) than a nucleic acid that has a similar sequence (e.g., identical or non-identical) but is non-circularized. The circularized nucleic acid will have greater stability in solution. A circularized nucleic acid will have greater stability in a cell, whether in vitro or in vivo (i.e., in an animal). By "greater stability" is meant a stability increase of 0.01%, 1%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 6000%, 7000%, 8000%, 9000%, 10000%, or more or any percentage therebetween. For example, a greater (as defined above) fraction of the starting amount of circularized nucleic acid will remain in a solution or a cell after a certain amount of time when under identical conditions (e.g., temperature and presence/absence of digestive enzymes) than a corresponding non-circularized nucleic acid.

A circularized nucleic acid may provide greater polypeptide translation (e.g., more polypeptide product and more efficient synthesis) relative to a nucleic acid that has a similar sequence (e.g., identical or non-identical) but is non-circularized. Specifically, the circularized nucleic acid according to the present invention provides greater polypeptide translation (e.g., more polypeptide product and more efficient synthesis) relative to a non-circularized nucleic acid having a similar sequence (e.g., identical or non-identical) but has CRC sequence motifs that are 100% complementary (i.e., no nucleotide mismatches). By "greater polypeptide translation" is meant an increase of 0.01%, 1%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 6000%, 7000%, 8000%, 9000%, 10000%, or more or any percentage therebetween in the amount of polypeptide produced. For example, a greater (as defined above) number of polypeptides will be synthesized from a molecule of circularized nucleic acid than from a corresponding non-circularized nucleic acid or a nucleic acid circularized using CRC sequence motifs that are 100% complementary.

A nucleic acid may comprise an internal ribosome entry site (IRES). Exemplary IRES sequences are listed at the World Wide Web at iresite.org. Preferably, the IRES is an encephalomyocarditis virus (EMCV) IRES.

A nucleic acid of the present invention may be in a cell (e.g., in vitro or in vitro in a non-human mammal). Non-limiting examples of cells include T cells, B cells, Natural Killer cells (NK), Natural Killer T (NKT) cells, mast cells, eosinophils, basophils, macrophages, neutrophils, dendritic cells, mesenchymal cells, endothelial cells, and epithelial cells.

A circularized nucleic acid of the present invention may be included in a composition, e.g., a pharmaceutical composition suitable for administration to a subject, e.g., a mammal, including a human. The composition may include both a circularized nucleic acid of the present invention and a nucleic acid having a similar sequence (e.g., identical or non-identical) but is non-circularized or a nucleic acid having a dissimilar sequence.

Methods for Circularizing RNA

In some embodiments, the present application provides methods for preparing a circular nucleic acid (e.g., a circular mRNA). For example, FIG. 1A illustrates a method of preparing a circular RNA. As shown, DNA template 101 containing a gene of interest (e.g., an open reading frame) is used in an in vitro transcription reaction to generate RNA product 102. While it is appreciated that DNA template 101 is shown generically configured for transcription using a T7 RNA polymerase, any enzyme that catalyzes the formation of an RNA molecule from a DNA template can be used in the methods described herein. Examples of suitable RNA polymerases are known in the art and include, without limitation, T3 RNA polymerase and SP6 RNA polymerase.

Following in vitro transcription, RNA product 102 comprises a 5'-triphosphate. In some embodiments, it can be desirable to convert the 5'-triphosphate to a 5'-monophosphate. For example, 5'-monophosphate groups are generally preferable to 5'-triphosphates for efficient 5' to 3' ligation reactions. Accordingly, as shown, the 5'-triphosphate of RNA product 102 is converted to 5'-monophosphate RNA 103. In some embodiments, the conversion to 5'-monophosphate is accomplished chemically. In some embodiments, the conversion to 5'-monophosphate is accomplished enzymatically.

In some embodiments, the conversion to 5'-monophosphate is accomplished in a two-step process comprising: (A) dephosphorylation; and (B) phosphorylation. In some embodiments, this two-step process can be accomplished enzymatically, e.g., through the activity of a phosphatase in (A) to remove the triphosphate and a kinase in (B) to add a 5'-monophosphate. Suitable phosphatase and kinase enzymes are known in the art and described elsewhere herein.

In some embodiments, the conversion to 5'-monophosphate is accomplished in a single-step process using a single enzyme that catalyzes the conversion of a 5'-polyphosphate to a 5'-monophosphate. For example, in some embodiments, the single enzyme is an enzyme whose activity cleaves a pyrophosphate group from a 5'-triphosphate, such as RppH or apyrase. Following 5'-phosphate modification, 5'-monophosphate RNA is enzymatically ligated (e.g., using a T4 RNA ligase) to produce mixed population 104 that comprises circular RNA and remnant linear RNA.

It is often desirable to obtain sufficiently pure circular RNA that minimizes or eliminates remnant linear RNA of mixed population 104. For example, remnant linear RNA and any other by-products and impurities can detrimentally affect use of the circular RNA as a therapeutic—e.g., through induction of innate immune response. Additionally, RNA molecules having longer sequences and/or extensive secondary structure can diminish ligation efficiency such that the amount of remnant linear RNA exceeds that of the circular RNA. Accordingly, aspects of the present application relate to methods of preparing purified circular RNA 105 by purifying mixed population 104 comprising linear and circular nucleic acids.

In some embodiments, mixed population 104 is purified by gel chromatography. In some embodiments, mixed population 104 is purified by column chromatography. In some embodiments, mixed population 104 is purified by HPLC. In some embodiments, mixed population 104 is purified by ion-pair reversed-phase HPLC. In some embodiments, mixed population 104 is purified by (i) contacting mixed population 104 to a purification column; (ii) eluting purified circular nucleic acid 105 by passing a liquid through the purification column; and (iii) collecting an eluate comprising purified circular nucleic acid 105. In some embodiments, the purification column comprises a stationary phase having a plurality of microspheres. In some embodiments, the plurality of microspheres comprise a polystyrene-divinylbenzene copolymer.

Circular RNA purified in accordance with the techniques described herein, in some embodiments, is in a preparation that is substantially free of linear RNA. For example, the circular RNA may have trace amounts of linear RNA, which would not be expected to illicit a detrimental immune response in a therapeutic application. In some embodiments, a circular RNA that has been purified by a method described herein is in a composition comprising trace amounts of its linear form up to about 15% of its linear form (or fragments thereof. In some embodiments, the circular RNA composition comprises between about 0.1% and 10%, between about 0.5% and 5%, between about 0.5% and 1%, between about 1% and 5%, between about 0.1% and 1%, between about 0.1% and 0.5%, between about 0.01% and 0.1%, or between about 0.05% and 0.1% of its linear form (or fragments thereof).

Figure 1B:
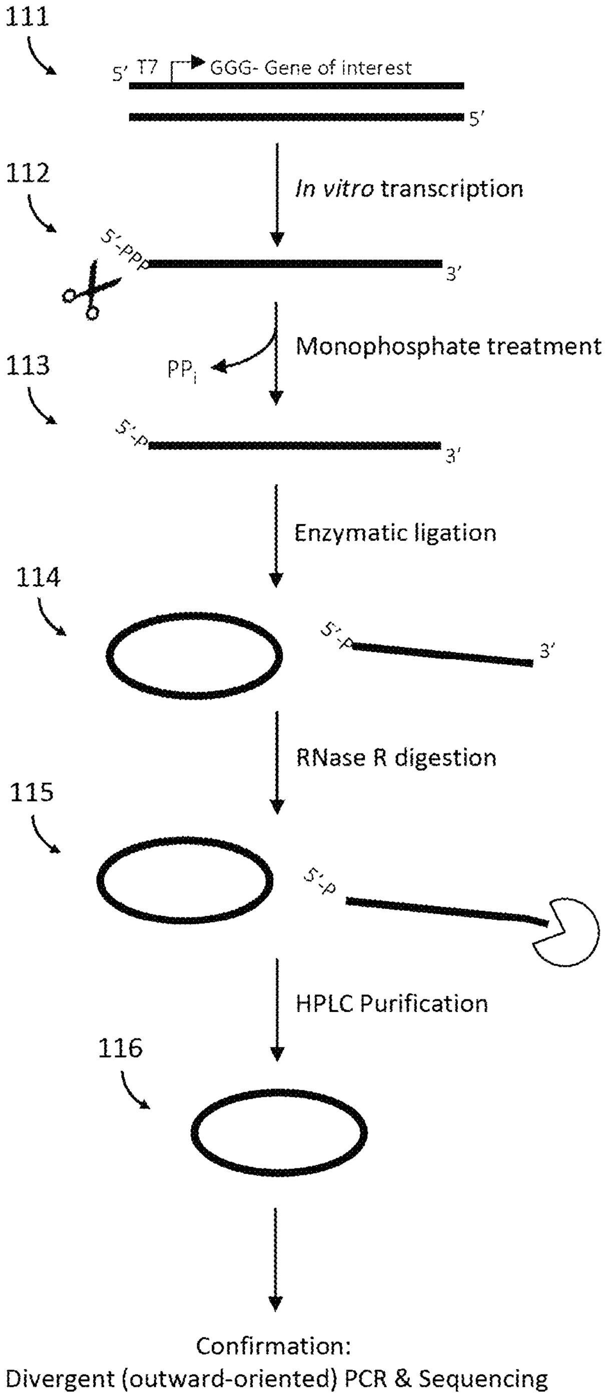

FIG. 1B illustrates a further example of a method of preparing a circular RNA. As shown, DNA template 111 containing a gene of interest (e.g., an open reading frame) is used in an in vitro transcription reaction to generate RNA product 112. Using a single-step enzymatic process (e.g., via the activity of RppH or apyrase), the 5'-triphosphate of RNA product 112 is converted to 5'-monophosphate RNA 113. Following an enzymatic ligation reaction, 5'-monophosphate RNA 113 is ligated to produce mixed population 114 comprising circular RNA and remnant linear RNA.

As shown, mixed population 114 is subjected to an enzymatic digestion using an exonuclease that selectively degrades remnant linear RNA of mixed population 114 to produce digested mixed population 115 comprising circular RNA and impurities (e.g., degradation products, exonuclease, remnant linear RNA). While it is appreciated that RNase R is used in this example, many exonucleases suitable for degrading remnant linear RNA are known in the art and described elsewhere herein. Digested mixed population 115 is subjected to HPLC purification to obtain purified circular RNA 116.

Figure 1C:
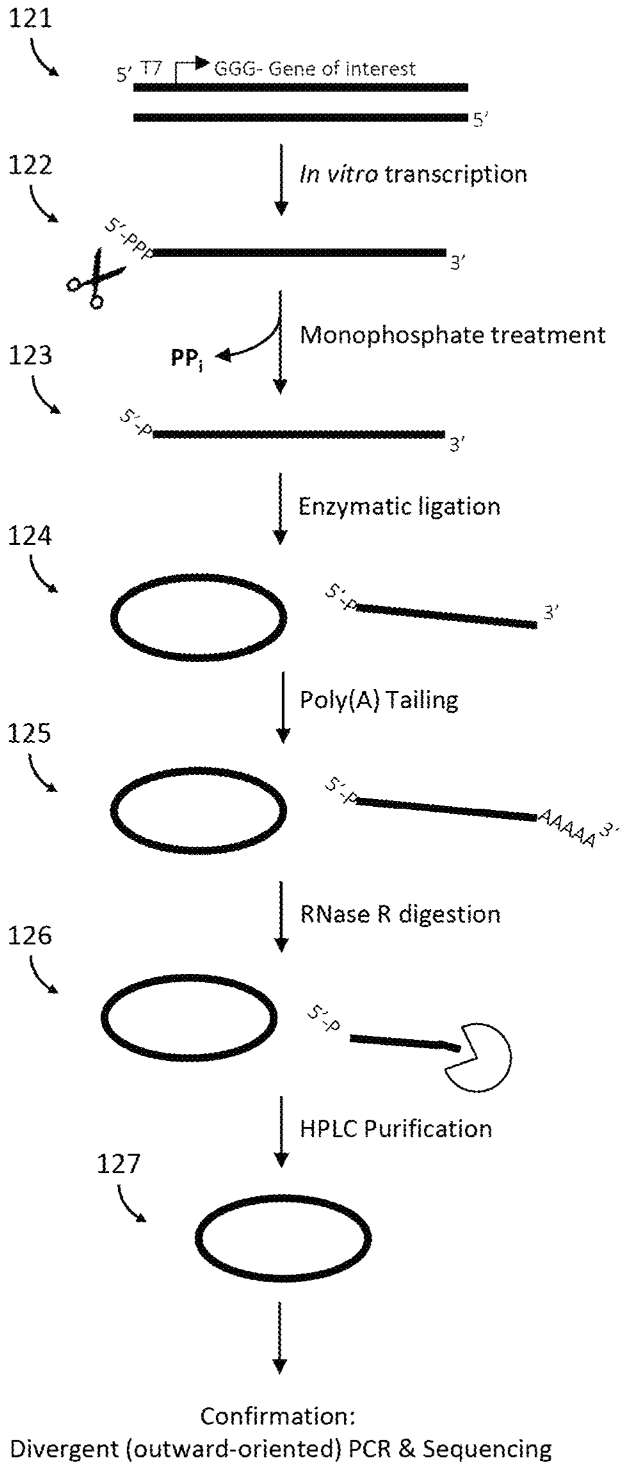
Figure 2A:
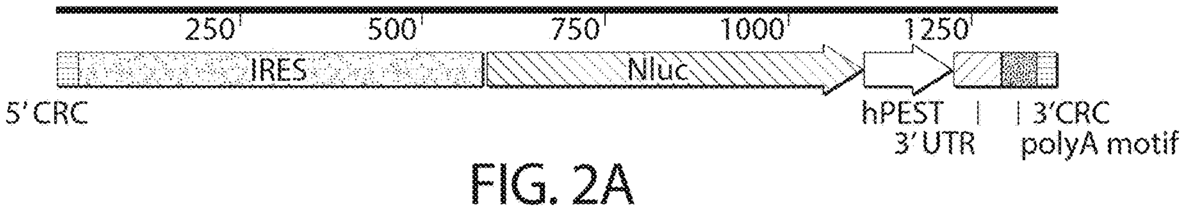
FIGS. 2A-2E illustrate an example set of experiments which demonstrate isolation of circular mRNA by HPLC.
Figure 2B:
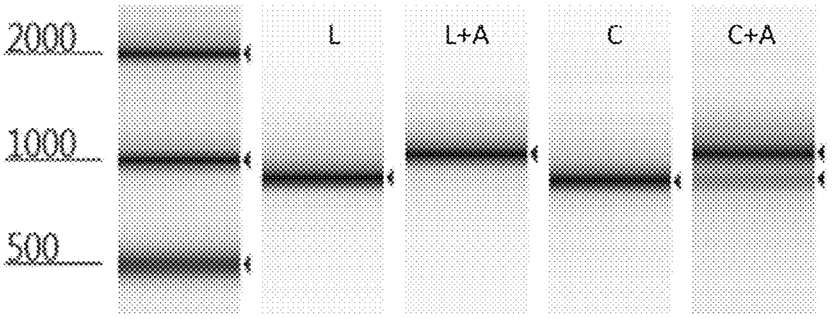
Figure 2C:
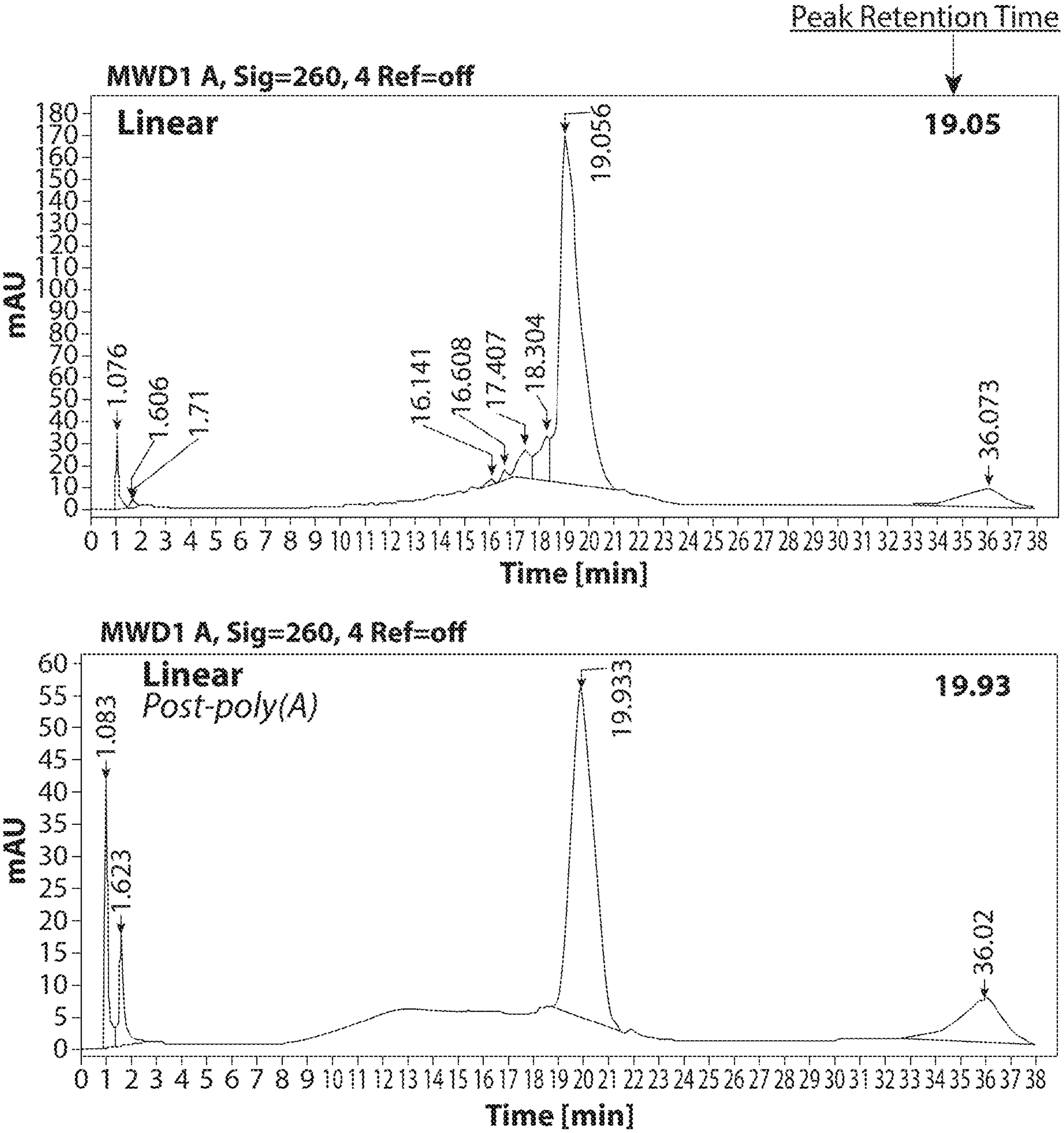
Figure 2C:
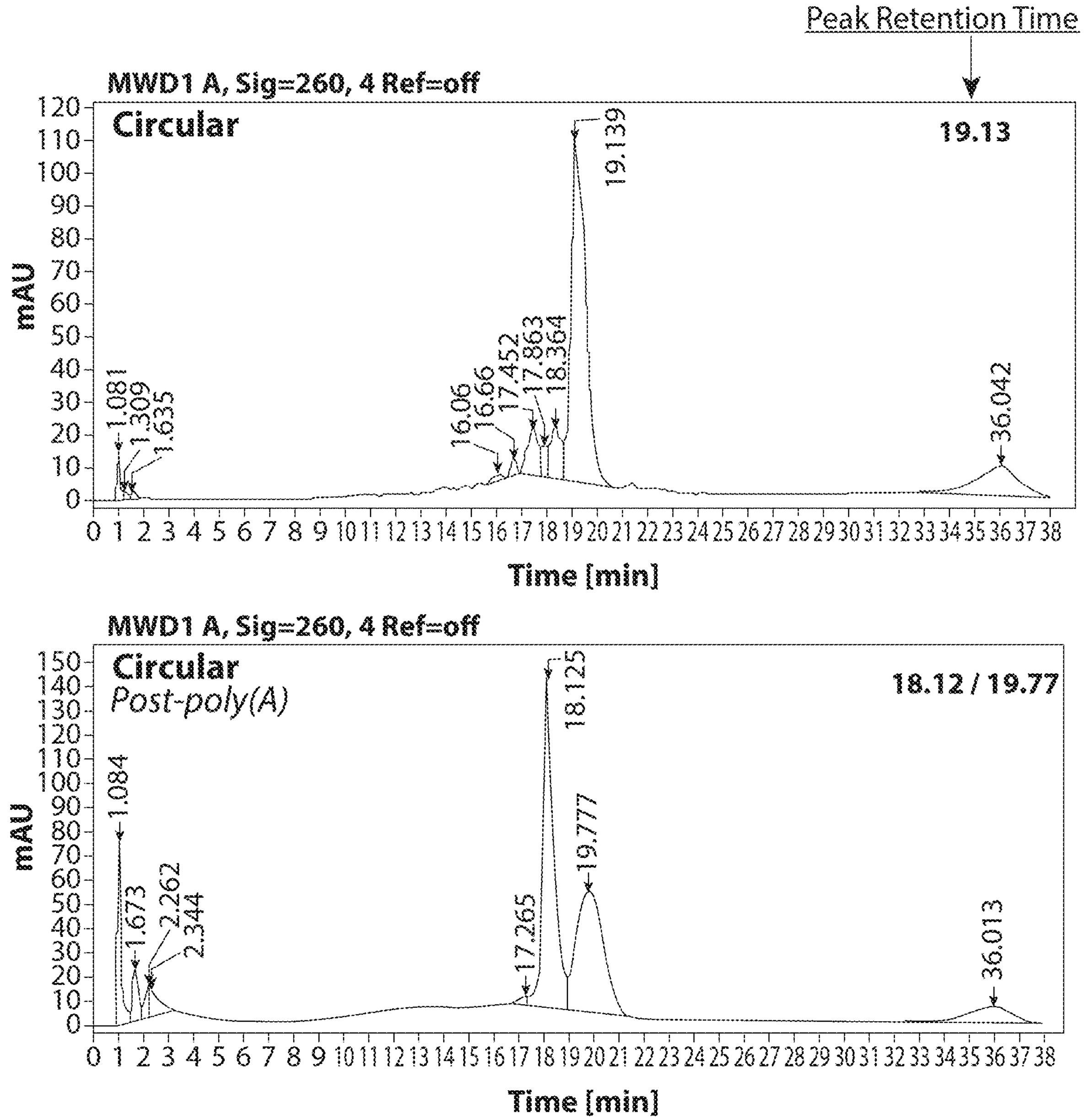
Figure 2D:
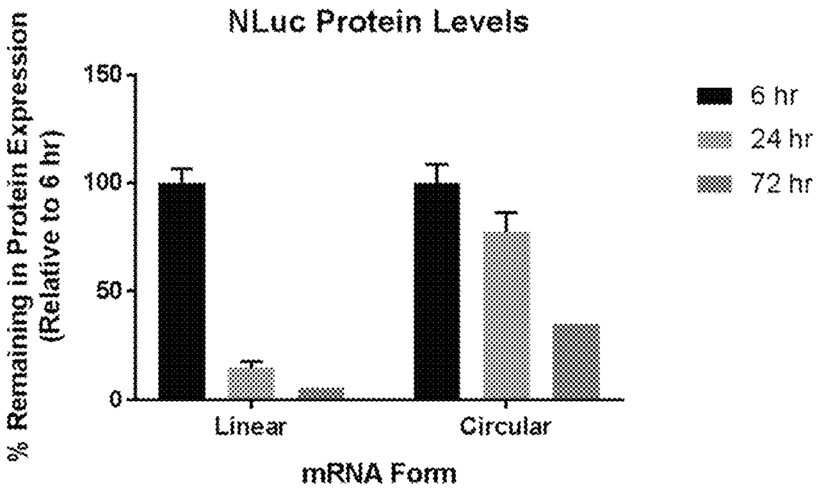
Figure 2E:
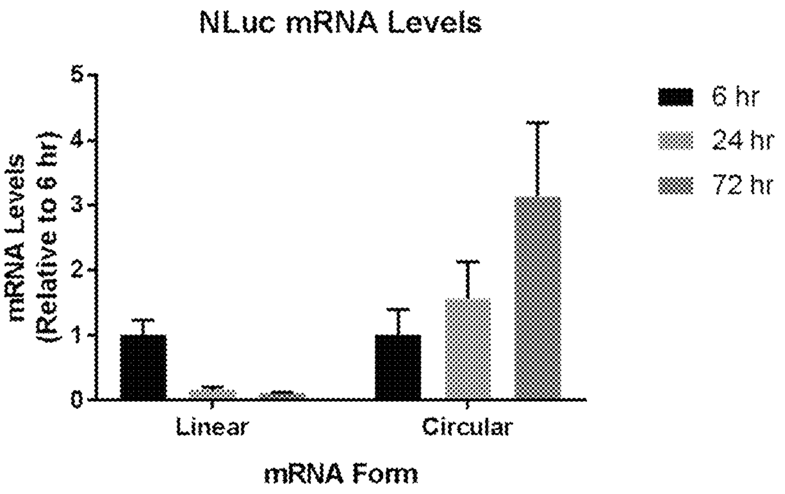
Figure 3A:
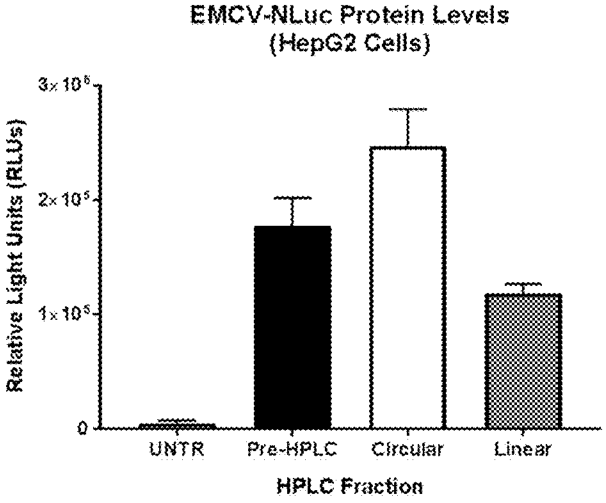
FIGS. 3A-3G depict an example comparative analysis of IRES elements, which indicates that EMCV, but not PPT19, exhibits high levels of IRES activity in pure circular mRNA. EMCV-NLuc (FIG. 3A) and PPT19-NLuc mRNA (FIG. 3B) were circularized and run on HPLC to isolate the circular and linear mRNA present in the samples (UNTR: Untransfected cells). The circular fraction, linear fraction, or pre-HPLC samples were transfected into HepG2 cells, and protein expression was measured 24 hours post-transfection. HPLC-purified linear or circular NLuc mRNA containing EMCV, PPT19, or the 5' UTR of insulin upstream of the coding sequence were transfected into H1299 cells, and protein expression was measured 24 h post-transfection (FIG. 3C). A panel of circular RNAs that differed only in the IRES incorporated into their 5' UTR was tested for variations in protein translation.
Figure 3B:
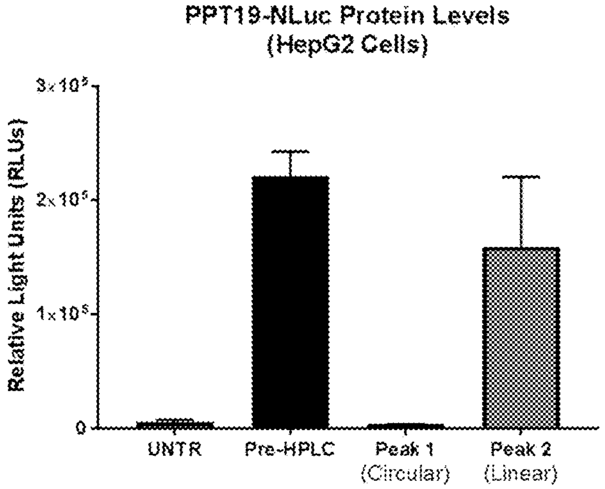
Figure 3C:
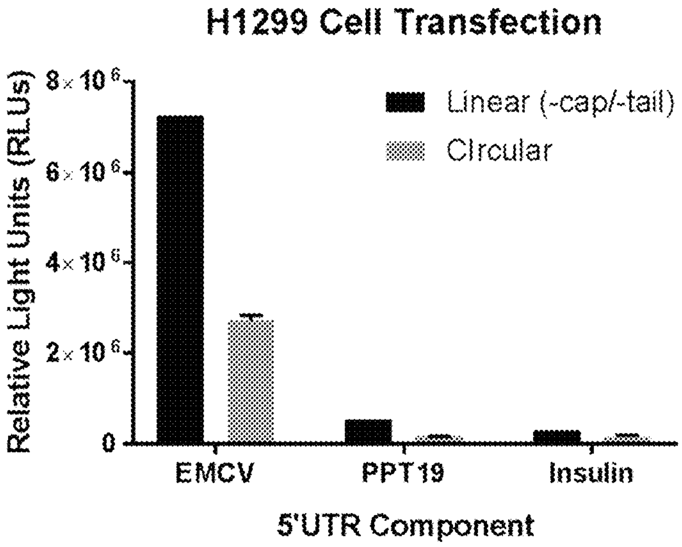
Figure 3D:
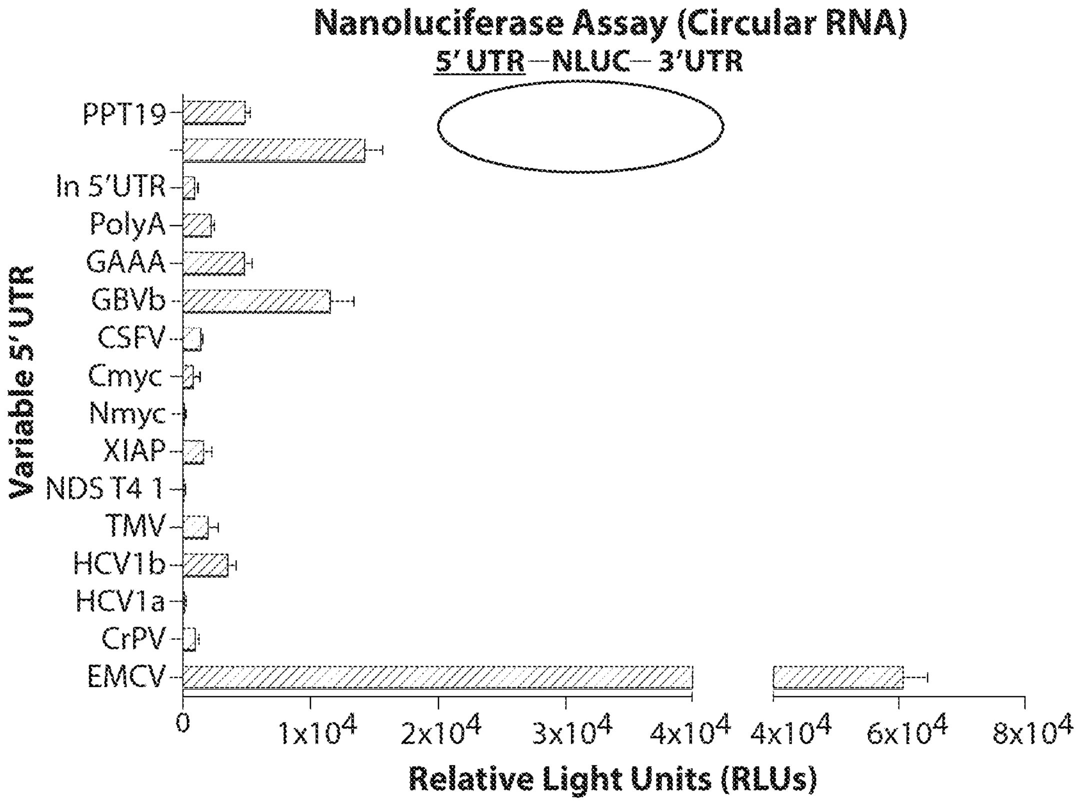
Figure 3E:
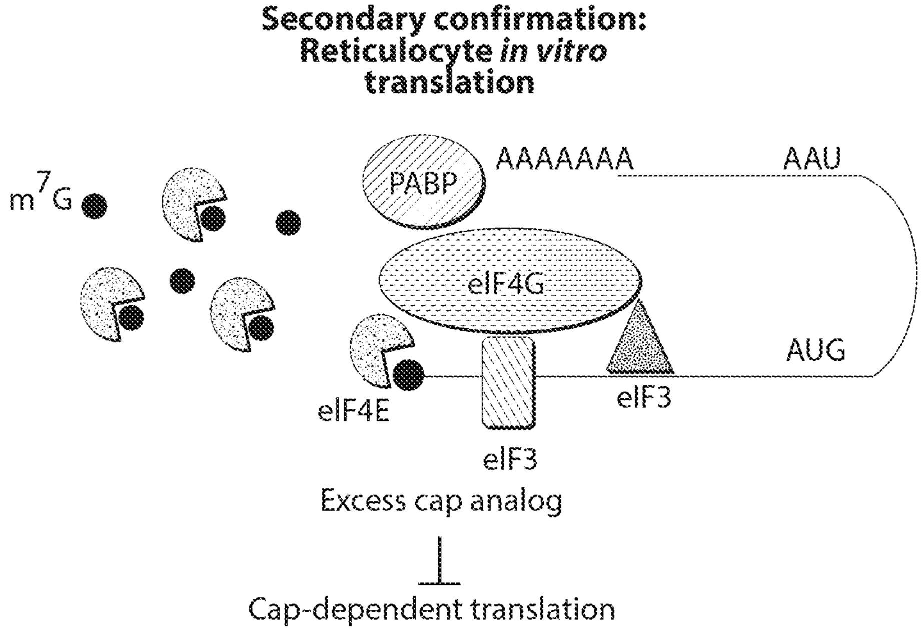
Figure 3F:
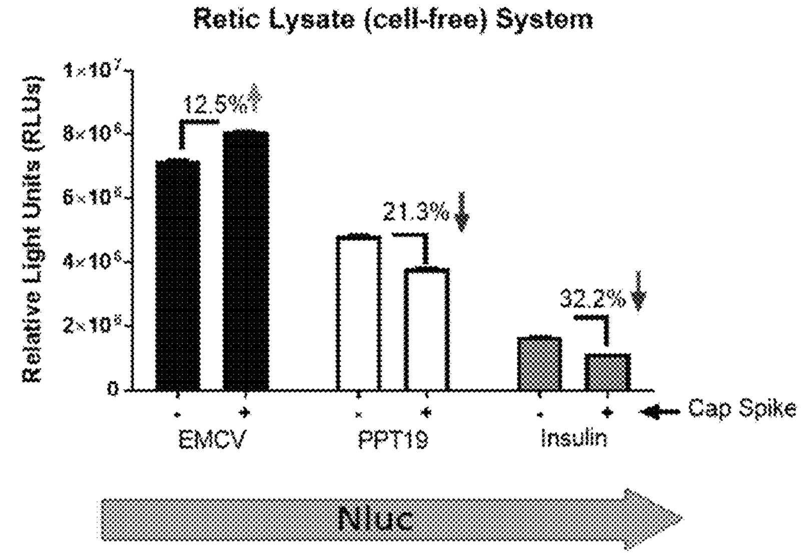
Figure 3G:
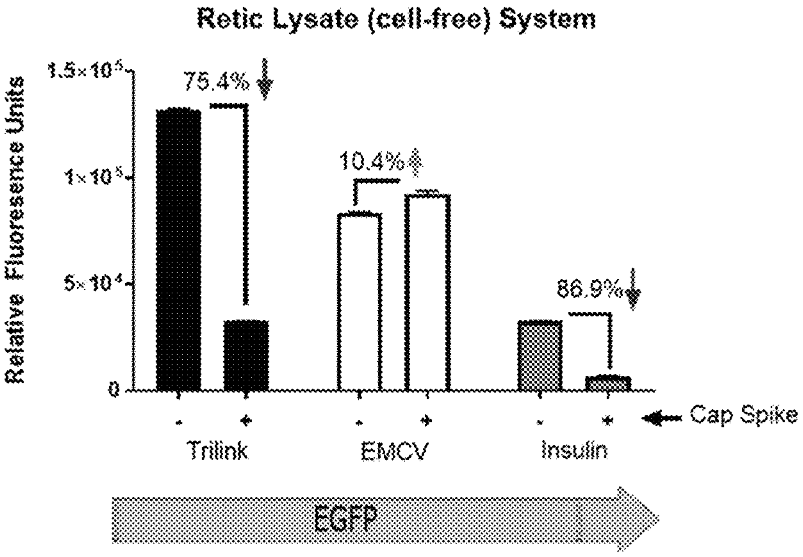

FIG. 1C illustrates a further example of a method of preparing a circular RNA. As shown, DNA template 121 containing a gene of interest (e.g., an open reading frame) is used in an in vitro transcription reaction to generate RNA product 122. Using a single-step enzymatic process (e.g., via the activity of RppH or apyrase), the 5'-triphosphate of RNA product 122 is converted to 5'-monophosphate RNA 123. Following an enzymatic ligation reaction, 5'-monophosphate RNA 123 is ligated to produce mixed population 124 comprising circular RNA and remnant linear RNA.

As shown, mixed population 124 is subjected to a poly(A) tailing reaction to produce tailed mixed population 125 comprising circular RNA and tailed remnant linear RNA. The activity of poly(A) polymerase requires a free 3' terminal end for polyadenylation to occur. In this example, circular RNA cannot be modified by polyadenylation because the enzymatic ligation is accomplished by 5' to 3' end ligation such that these ends are unavailable for modification by poly(A) polymerase.

In some embodiments, selective polyadenylation of remnant linear RNA increases the efficiency of its subsequent degradation in a mixed sample. For example, as shown, tailed mixed population 125 is subjected to an enzymatic digestion using an exonuclease (e.g., RNase R) that selectively degrades remnant linear RNA of tailed mixed population 125 to produce digested mixed population 126 comprising circular RNA and impurities (e.g., degradation products, exonuclease, remnant linear RNA).

As described elsewhere herein (see, e.g., Example 9 and FIG. 8C), in some embodiments, polyadenylation enhances exonuclease reaction kinetics such that a greater amount of linear RNA is degraded in a shorter period of time relative to the same or similar linear RNA that is not polyadenylated. In some embodiments, the enhanced exonuclease activity promotes peak separation in a subsequent purification. In this example, digested mixed population 126 is subjected to HPLC purification to obtain purified circular RNA 127.

While it is appreciated that steps of polyadenylation and RNase R digestion are used in the example process illustrated in FIG. 1C, the inventors have recognized an assortment of techniques which generally involve selectively modifying one or both of a circular or linear RNA in a mixed population to facilitate purification. By making such modifications, it permits easier enrichment, isolation, and/or separation of the desired circular portion in respect of the linear portion of the mixed population.

For example, a selective modification of a molecule can be made for the purpose of affecting its movement on a column relative to the unmodified molecule. Such modifications can include, by way of example and not limitation, size modifications and charge modifications which increase chromatographic separation of one RNA form relative to the other, and capture moiety modifications which permit selective capture of one form over the other.

Size modifications can be made to permit separation based on a difference in size between one RNA form relative to another, e.g., by size exclusion chromatography and other purification techniques which discriminate based on size. Examples of size modifications include selectively increasing the size of one RNA form relative to another. This can be accomplished by any number of means known to a practitioner, including selectively ligating one or more molecules to a linear RNA (e.g., through the action of a poly(A) polymerase), selectively ligating a nucleic acid to a linear RNA (e.g., through the action of a ligase), selectively coupling a protein element to either RNA form (e.g., by chemical coupling means), and selectively annealing a nucleic acid to either form (e.g., using an oligonucleotide that anneals across the splice junction of a circular form). Size modifications further include those which selectively decrease the size of one RNA form relative to another. Typically, such methods can involve some form of degradation and would therefore involve selective modification of the linear RNA form. For example, selective degradation can be accomplished by means which discriminate based on the available free ends of the linear form (e.g., enzymatic degradation via an exonuclease).

Charge modifications can be made to permit separation based on a difference in molecular charge of one form relative to another, e.g., by ion chromatography or by electrophoresis. This can be accomplished by selectively ligating or annealing a charged molecule to one RNA form. As one example, nucleic acids are generally negatively charged under neutral conditions. Therefore, selectively ligating or annealing a nucleic acid to one form of RNA would be expected to decrease the overall charge of that form. As should be appreciated, such modifications would invariably result in the modified form being more attracted to a positive charge, thereby providing a means of separation by charge.

Capture moiety modifications can be made to permit selective capture of one form over another. A process for selective capture can generally involve: (i) selectively modifying either circular or linear RNA of a mixed population with a capture moiety; and (ii) capturing the capture moiety-modified RNA by contacting the mixed population with a binding partner of the capture moiety. For example, in some embodiments, a capture moiety is annealed or ligated to one form of RNA in a mixed population, and a binding partner of the capture moiety is contacted to the mixed population.

The capture moiety can be in the form of a capture moiety-modified nucleotide, for example, which can be ligated to one or both terminal ends of a linear RNA (e.g., polyadenylating linear RNA in the presence of biotin-modified adenosine). Alternatively, a capture moiety-modified primer could be designed to preferably anneal to one RNA form under a particular set of conditions. By way of example and not limitation, a capture moiety-modified primer comprising a sequence that is complementary to a region bridging the splice junction of a circular RNA could be used to preferably anneal to—and capture—the circular RNA.

Additional capture moiety modifications include ligating one or more nucleotides to the linear form, and capturing the linear form using an oligonucleotide probe that selectively anneals to the one or more nucleotides ligated thereon. For example, polyadenylation of a linear form produces a poly (A) tail, which functions as a capture sequence for binding to a poly(T) nucleic acid probe.

A capture moiety and/or binding partner can comprise, for example, biotin, avidin, streptavidin, digoxigenin, inosine, avidin, GST sequences, modified GST sequences, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

Capture can be performed using any of a variety of techniques known in the art. For example, a capture moiety comprising an affinity purification tag could permit capture via passage through an affinity column. and preferably bound by the solid phase. Alternatively, a capture moiety comprising a charged moiety could permit capture by electrophoretic means or column chromatography. As an additional example, a capture moiety comprising a paramagnetic bead could permit capture by applying a magnetic field to the sample.

The nucleic acid comprising the RNA sequence to be circularized can be produced by methods known in the art.

For example, primers can be designed to generate PCR templates suitable for in vitro transcription (IVT), for example by T7, T3, or S6 RNA polymerase. Preferably, the primers are designed with the following motifs:

Forward primer: {RNA polymerase promoter sequence-5'-(random nucleotides, e.g., of a tail sequence)-(5' iCRC sequence)-(desired 5' UTR)-($1^{st}$ 20 nucleotides of desired RNA CDS)-3'}

Reverse primer: {5'-(random nucleotides, e.g., of a tail sequence)-(3'iCRC sequence)-(reverse complement of desired 3' UTR)-(reverse complement of last 20 nucleotides of desired RNA CDS)-3'}

Circularized RNA is produced by transcription of the PCR products generated with the above primers, or another set of primers, to produce RNA. Circularized RNA may also be produced by transcription of a plasmid or a fragment thereof to produce RNA. The synthesized RNA is then treated to produce a 5' monophosphate RNA. For example, 5' monophosphate RNA is produced by treating the RNA with RNA 5' pyrophosphohydrolase (RppH) or an ATP diphosphohydrolase.

The 5' monophosphate RNA is then enzymatically circularized for example with an RNA ligase such as T4 RNA ligase.

A nucleic acid of the present invention, which is non-circularized, may be circularized by ligating its 5' terminus to its 3' terminus. Ligating may be enzymatic, e.g., by a ligase. Preferably, the ligase is T4 RNA ligase.

Prior to ligation, a non-circularized nucleic acid is contacted with a phosphatase, e.g., RNA 5' pyrophosphohydrolase (RppH) or an ATP diphosphohydrolase, to produce a 5' monophosphate RNA. Alternately, a non-circularized nucleic acid is contacted with a phosphatase, e.g., Antarctic Phosphatase, Shrimp Alkaline Phosphatase, and Calf Intestinal Phosphatase, and then contacted with a kinase, e.g., Polynucleotide Kinase.

A nucleic acid may undergo multiple (e.g., two, three, four, five, or more) rounds of ligation, thereby ensuring that the majority of nucleic acids, in a sample, is circularized, e.g., about 100%, about 90%, about 80%, about 70%, about 60%, about 51%, or any amount therebetween.

Optionally, non-circularized (i.e., linear) RNA is removed using an exonuclease to digest the linear RNA, e.g., RNase R, Exonuclease T, λ Exonuclease, Exonuclease I, Exonuclease VII, T7 Exonuclease, or XRN-1. Preferably, the exonuclease is RNase R and/or XRN-1.

Methods for Purifying Circularized RNA

The established method for isolating circular mRNA (Beaudry, *Nucleic Acids Research,* 1995; 23(15):3064-66.) is limited in terms of yield and the size of RNA that can be isolated. Most significantly, the mRNA isolated from a denaturing PAGE gel is not suitable for translation.

Accordingly, another aspect of the invention provides a novel method of isolating pure circular mRNA. The unpurified circular mRNA sample is exposed to poly(A) polymerase, followed by HPLC. Exonuclease-mediated degradation of residual linear mRNA may be performed prior to HPLC. This method (e.g., HPLC) has the added benefit of removing impurities present in in vitro transcribed mRNA samples.

Specifically, prior to HPLC, the unpurified circular mRNA sample is treated with a polyadenylase that adds a ~100-200 nucleotide poly(A) tail to linear mRNA only, as circular mRNA does not have a free 3' end to which the enzyme could make additions. This method allows efficient separation of the circular and linear forms of mRNA when the samples are run on an RNAsep HPLC column.

Alternatively, another aspect of the invention provides a second novel method of isolating pure circular mRNA. The unpurified circular mRNA sample is exposed to a second nucleic acid of different length along with a splint and a ligase, followed by HPLC.

Specifically, prior to HPLC, the unpurified circular mRNA sample is treated with a ligase in the presence of a nucleic acid that is considerably longer or shorter than the sequence that was circularized. The second sequence may be DNA or RNA. The splint across the first and second sequence may be DNA or RNA. The ligase may be a T4 RNA ligase. The second sequence may have a length that is at least 100 nucleotides different than the first sequence. The second sequence may have a length that is between about 100 and 5000 nucleotides different than the first sequence. For example, the second sequence may have a length that is between 200 and 4000, between 300 and 3000, between 400 and 2500, between 500 and 2000, between 600 and 2500, between 700 and 2000, between 800 and 1500, between 900 and 1000 nucleotides different than the first sequence. The second sequence may have a length that is 100, 200, 300, 400, 500, 600, 700, 800, 900, 1000, 1500, 2000, 2500, 3000, 4000, or 5000 nucleotides different than the first sequence. The ligase will ligate the second sequence to linear mRNA only, as circular mRNA does not have free 5' or 3' ends to which the enzyme could make additions. While the splint should enrich for ligation between the first and second sequences over ligation between two or more molecules of the second sequence, use of a second sequence that contains a 5' hydroxyl will render it incompetent to ligation such that the second sequence will have to be ligated via its 3' end to a 5' monophosphate on the residual linear molecules of the first sequence. Performance of an additional round of ligation with ligase may even increase the yield of circular RNA. The splint may have a length of 20, 30, 40, 50, 60, 70, 80, 90, 100, 120, 140, 160, 180, or 200 nucleotides. This method allows efficient separation of the circular and linear forms of mRNA when the samples are run on an RNAsep HPLC column.

Methods of Using Circularized RNA

The circularized RNA produced according to the methods of the invention are useful in gene therapy. In particular, the circularized RNA is useful for protein replacement therapy or in the production of RNA-based vaccines for an array of antigens. For example, the circularized RNA (e.g., mRNA) can encode tumor-associated antigens useful as cancer vaccines. In another aspect, the circularized RNA (e.g., mRNA) can encode a bacterial or viral antigen to prevent or alleviate a symptom of a bacterial or viral infection, e.g., as a vaccine. Additional embodiments include use of circularized RNA for use in cancer immunotherapies, infectious disease vaccines, genome engineering, genetic reprogramming, and protein-replacement/supplementation therapies.

Alternatively, the circularized RNA (e.g., mRNA) can encode a chimeric antigen receptor and be used to create a chimeric antigen receptor T cell useful in immunotherapy. Chimeric antigen receptors (CARs) comprise binding domains derived from natural ligands or antibodies specific for cell-surface antigens, genetically fused to effector molecules such as the TCR alpha and beta chains, or components of the TCR-associated CD3 complex. Upon antigen binding, such chimeric antigen receptors link to endogenous signaling pathways in the effector cell and generate activating signals similar to those initiated by the TCR complex. A CAR typically has an intracellular signaling domain, a transmembrane domain, and an extracellular domain.

The transmembrane and/or intracellular domain may include signaling domains from CD8, CD4, CD28, 4-1BB, OX40, ICOS, and/or CD3-zeta. The transmembrane domain can be derived either from a natural or from a synthetic source. The transmembrane domain can be derived from any membrane-bound or transmembrane protein.

The transmembrane domain may further include a stalk region positioned between the extracellular domain (e.g., extracellular ligand-binding domain) and the transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively, the stalk region may be a synthetic sequence that corresponds to a naturally occurring stalk sequence, or may be an entirely synthetic stalk sequence. In a preferred embodiment said stalk region is a part of human CD8 alpha chain.

The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCR zeta, FcR gamma, FcR beta, FcR epsilon, CD3 gamma, CD3 delta, CD3 epsilon, CDS, CD22, CD79a, CD79b and CD66d. In a preferred embodiment, the signaling transducing domain of the CAR can comprise the CD3 zeta signaling domain, or the intracytoplasmic domain of the Fc epsilon RI beta or gamma chains.

The CAR may further include one or more additional costimulatory molecules positioned between the transmembrane domain and the intracellular signaling domain, to further augment potency. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. In some embodiments the intracellular signaling domain contains 2, 3, 4, or more costimulatory molecules in tandem.

The extracellular domain may include an antibody such as a Fab, a scFV, or a single-domain antibody (sdAb also known as a nanobody) and/or may include another polypeptide described herein. In a preferred embodiment, said extracellular ligand-binding domain is a single chain antibody fragment (scFv) comprising the light (VL) and the heavy (VH) variable fragment of a target antigen specific monoclonal antibody joined by a flexible linker. Other binding domain than scFv can also be used for predefined targeting of lymphocytes, such as camelid single-domain antibody fragments (which are examples of an sdAb) or receptor ligands, antibody binding domains, antibody hypervariable loops or CDRs as non-limiting examples.

As non-limiting examples, the antigen of the CAR can be a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostate specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelia, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers.

A circularized nucleic acid of the present invention may encode a CAR and may be transfected or infected into a T-cell using any technique known in the art. A T cell that expresses the CAR is referred to as a chimeric T cell receptor cell (CART). The CART will express and bear on the cell surface membrane the chimeric antigen receptor encoded by the RNA sequence of a circularized nucleic acid of the present invention.

The present invention includes a nucleic acid encoding a CAR, methods for preparing a nucleic acid encoding a CAR, compositions comprising a nucleic acid encoding a CAR, methods for producing a CART, methods for treating a diseases using a CART, an isolated CART, and non-human mammals comprising a CART.

Any of the herein-described aspects or embodiments can be combined with any other aspect or embodiment described herein.

Definitions

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, and uracil, xanthine, inosine, and qucuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group. Preferably, the modified base is 5-methylcytidine (5mC).

Further, the term nucleotide also includes those species that have a detectable label, such as for example a radioactive or fluorescent moiety, or mass label attached to the nucleotide.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively).

The terms "ribonucleic acid" and "RNA" as used herein mean a polymer composed of ribonucleotides.

As used herein, the terms "mRNA" and "RNA" may be synonyms.

The terms "deoxyribonucleic acid" and "DNA" as used herein mean a polymer composed of deoxyribonucleotides. "Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions, that is having one or more nucleotide mismatches.

As defined herein, "RNA ligase" means an enzyme or composition of enzyme that is capable of catalyzing the joining or ligating of an RNA acceptor oligonucleotide, which has an hydroxyl group on its 3' end, to an RNA donor, which has a 5' phosphate group on its 5' end. The invention is not limited with respect to the RNA ligase, and any RNA ligase from any source can be used in an embodiment of the methods and kits of the present invention. For example, in some embodiments, the RNA ligase is a polypeptide (gp63) encoded by bacteriophage T4 gene 63; this enzyme, which is commonly referred to simply as "T4 RNA ligase," is more correctly now called "T4 RNA ligase 1" since Ho, C K and Shuman, S (Proc. Natl. Acad. Sci. USA 99: 12709-12714, 2002) described a second RNA ligase (gp24.1) that is encoded by bacteriophage T4 gene 24.1, which is now called "T4 RNA ligase 2." Unless otherwise stated, when "T4 RNA ligase" is used in the present specification, is meant "T4 RNA ligase 1". For example, in some other embodiments, the RNA ligase is a polypeptide derived from or encoded by an RNA ligase gene from bacteriophage TS2126, which infects Thermus scotoductus, as disclosed in U.S. Pat. No. 7,303,901 (i.e., bacteriophage TS2126 RNA ligase).

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus "Transcription" means the formation or synthesis of an RNA molecule by an RNA polymerase using a DNA molecule as a template. The invention is not limited with respect to the RNA polymerase that is used for transcription. For example, a T7-type RNA polymerase can be used.

"Translation" means the formation of a polypeptide molecule by a ribosome based upon an RNA template.

"Melting temperature" ($T_m$) is defined as the temperature at which half of the DNA strands are in the random coil or single-stranded (ssRNA) state.

"Annealing temperature" ($T_a$) is defined as the temperature in which single-stranded nucleic acids associate such that double-stranded molecules are formed, often by heating and cooling.

It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about", is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

A "subject" in the context of the present invention is preferably a mammal. The mammal can be a human, non-human primate, mouse, rat, dog, cat, horse, or cow, but are not limited to these examples.

As used herein, the term "encode" refers broadly to any process whereby the information in a polymeric macromolecule is used to direct the production of a second molecule that is different from the first. The second molecule may have a chemical structure that is different from the chemical nature of the first molecule.

For example, in some aspects, the term "encode" describes the process of semi-conservative DNA replication, where one strand of a double-stranded DNA molecule is used as a template to encode a newly synthesized complementary sister strand by a DNA-dependent DNA polymerase. In other aspects, a DNA molecule can encode an RNA molecule (e.g., by the process of transcription that uses a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

The invention will be further illustrated in the following non-limiting examples.

EXAMPLES

Example 1: Circularized RNA Synthesis

RNA was synthesized using the HiScribe T7 High Yield RNA Synthesis Kit (NEB, #E2040S) according to manufacturer's instructions. 500-1000 ng of PCR product encoding the desired RNA sequence was used as template in these in vitro transcription (IVT) reactions. Synthesized RNA was then treated with RNA 5' Pyrophosphohydrolase, or RppH, (NEB, #M0356S) to provide the 5' monophosphate end necessary for enzymatic circularization. RppH-treated RNA was enzymatically circularized in reactions containing final concentrations of: 10% DMSO, 200 μM ATP, 1× NEB Buffer 4, 40 U RNaseOUT (Life Technologies, #10777-019), and 30 U of T4 RNA Ligase 1 (NEB, #M0204L) for 2 hours at 37° C. Remaining linear RNA in the circularization reactions is removed by HPLC (described in Example 4). After each step, reactions were purified using the GeneJet RNA Purification Kit (Thermo Scientific, #K4082). Circularization of RNA less than 1000 nucleotides was confirmed by running 500 ng of RNA product on a 6% polyacrylamide gel in 7 M Urea-TBE (Life Technologies, #EC6865) for 3 hours at 180 V, 4° C. Circularized product characteristically migrates slower than linear RNA, so a slower migrating band indicated circularized product when run alongside control non-circularized RNA. Additional confirmation was carried out using outward-oriented PCR (OOPCR), where primers are oriented outward from one other with respect to the linear template (as opposed to traditional PCR in which primers are oriented towards each other). cDNA was synthesized (Life Technologies, #4402954) from RNA samples and used as template in the OOPCR reactions. cDNA derived from non-circularized, linear RNA was used a negative control. An amplicon is generated solely from the circularized construct, as the polymerase can extend through the ligated ends.

Example 2: Generating CRC, 5' and 3' UTR Constructs

CRC sequences and experimental 5'/3' UTRs were appended to RNA coding sequence (CDS) by generating PCR templates for IVT that had been amplified with primers of the following design:

```
Forward primer:
                                        (SEQ ID NO: 79)
5'-(TAATACGACTCACTATAGGG)-(ttatgataac)-(tggctgcacga

attgcacaa)-(desired 5' UTR)-(varied based on RNA

CDS)-3'
```

{5'-(RNA polymerase promoter sequence)-(random nucleotides, e.g., of a tail sequence)-(5'CRC sequence)-(desired 5' UTR)-(1$^{st}$ 20 nucleotides of desired RNA CDS)-3'}.

```
Reverse primer:
                                          (SEQ ID NO: 80)
5'-(agcgacttcg)-(ttgtgcaattcgtgcagcca)-(desired 3'

UTR)-(varied based on RNA CDS)-3'
```

{5'-(random nucleotides, e.g., of a tail sequence)-(3'CRC sequence)-(reverse complement of desired 3' UTR)-(reverse complement of last 20 nucleotides of desired RNA CDS)-3'}

PCR templates generated with the above primers were used to generate circularized product in accordance with the procedures described in the below Examples.

Example 3: Measuring Translation Efficiency and RNA Stability

RNA constructs encoding nanoluciferase and complexed with Lipofectamine® 2000 (Life Technologies, #11668) were transfected into Hep3B cells (human hepatocyte cell line) seeded at 10,000 cells/well in a 96-well plate. Protein expression kinetics were measured using the Nano-Glo Luciferase Assay System (Promega, #N1110) using samples taken at 24, 48, and 72 hours post-transfection.

To measure RNA stability, qPCR was carried out using samples derived from cells that had been transfected as described above. cDNA was synthesized at each time point using the Power SYBR® Green Cells-to-Ct Kit (Life Technologies, #4402954) according to the manufacturer's instruction. The housekeeping gene β-actin was used to normalize the results.

Example 4: HPLC Purification of Circular mRNA

The established method for isolating circular mRNA (Beaudry, *Nucleic Acids Research,* 1995; 23(15):3064-66.) is limited in terms of yield and the size of RNA that can be isolated. Most significantly, the mRNA isolated from the denaturing PAGE gel is not suitable for translation. Alternative methods that have been attempted to optimize are not sufficiently effective, either; exonuclease treatment to degrade residual linear mRNA produces fragments of linear byproducts that are recognized by innate immune receptors, while oligo (dT)-mediated column separation of poly (A)-tailed linear mRNA leaves high levels of residual linear mRNA in the sample. An efficient method has been developed for isolating pure circular mRNA by exposing samples to poly (A) polymerase, followed by HPLC. This method has the added benefit of removing impurities present in in vitro transcribed mRNA samples. Prior to HPLC, circular mRNA samples are treated with a polyadenylase that adds a ~100-200 nucleotide poly (A) tail to linear mRNA only, as circular mRNA does not have a free 3' end to which the enzyme could make additions. This treatment allows efficient separation of the circular and linear forms of mRNA when the samples are run on an RNAsep HPLC column. In the absence of polyadenylation, the circular and linear forms cannot be separated by HPLC, as they elute at the same time owing to their identical lengths.

Example 5: Confirmation of IRES Activity in Circular mRNA

Characterization studies of pure circular mRNA have provided evidence that the putative IRES "PPT19" has little to no IRES activity, suggesting that previous translation from samples that included the PPT19 sequence was attributable to residual linear mRNA in those samples. The poly(A)+HPLC method has been used to isolate pure circular mRNA that contains: an EMCV IRES, a putative PPT19 IRES, or a non-IRES derived from the 5' UTR of insulin to evaluate the IRES activity of the 5' UTR motifs that have been used most commonly. The translation capacity of the pure circular mRNA was tested in H1299 and HepG2 cells and in a cell-free rabbit reticulocyte lysate translation system. In the latter, IRES activity was enriched for by adding excess cap analog, which sequesters the initiation components required for cap-dependent translation to occur. Using these assays, the IRES activity of EMCV in circular mRNA was confirmed, while little to no activity was observed with the PPT19 IRES.

Example 6: Evaluation of Methods for Preparing 5'-Monophosphate Ends

Figure 5B:
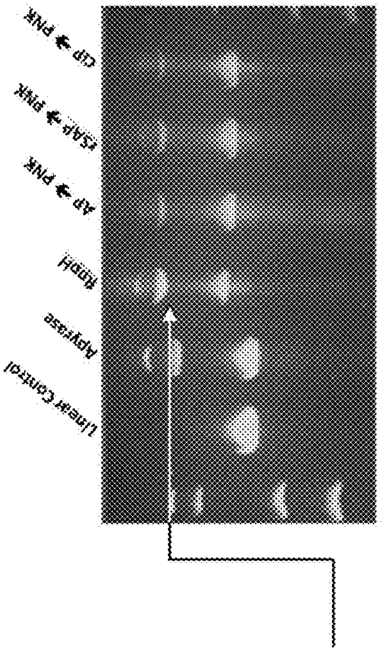
FIGS. 5A-5B depict a set of experiments evaluating different methods for 5'-monophosphate end preparation.
Figure 5A:
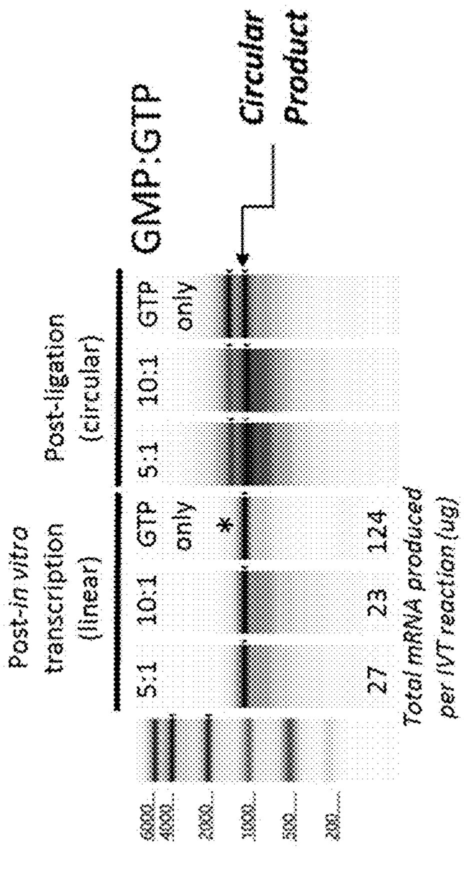

Different methods of 5'-monophosphate end preparation were evaluated, and the results are depicted in FIGS. 5A-5B. Based on the experimental data, RppH treatment was identified as a superior method for generating RNA with a 5' monophosphate end following in vitro transcription, leading to the greatest amount of circular product following ligation.

In FIG. 5A, lanes 1-3 of Agilent TapeStation are linear RNAs generated with 5-fold, 10-fold, or no GMP relative to GTP during in vitro transcription. The total amount of RNA generated under these conditions is listed at the bottom of each lane. As shown, there was a reduction in RNA produced per reaction when GMP was included. Lanes 4-6 contain the corresponding circular product, post-poly(A) polymerase treatment. As shown here, high levels of degradation were observed in the samples that used GMP during in vitro transcription.

In FIG. 5B, 500 ng of circular RNA generated by varied methods of 5'-monophosphate end preparation were run on a 5% polyacrylamide gel (7 M urea). Prior to ligation, RNA was treated with the indicated single enzyme (Apyrase, RppH) or two sequential enzymes (AP→PNK, rSAP→PNK, CIP→PNK) to produce the desired 5'-monophosphate ends. Lane 1 is the linear control not treated with any enzymes after in vitro transcription. Lanes 2-3 are samples that were modified using a single-step enzyme. Lanes 4-6 are samples that were modified using the two-step process for generating the 5'-monophosphate end. As shown, RppH consistently produced the highest level of circular product per reaction.

Example 7: HPLC Purification Following RNase R Digestion

Figure 6A:
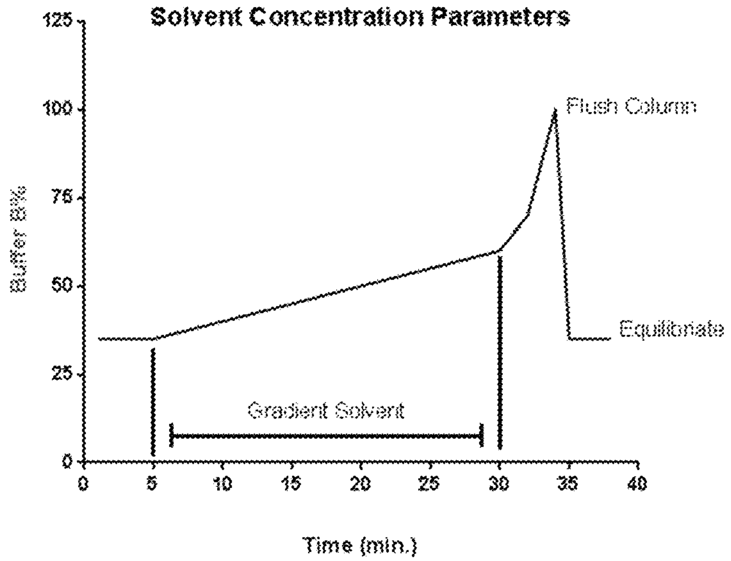
FIGS. 6A-6G depict an example HPLC purification and analysis of mRNA-induced immune response.
Figure 6B:
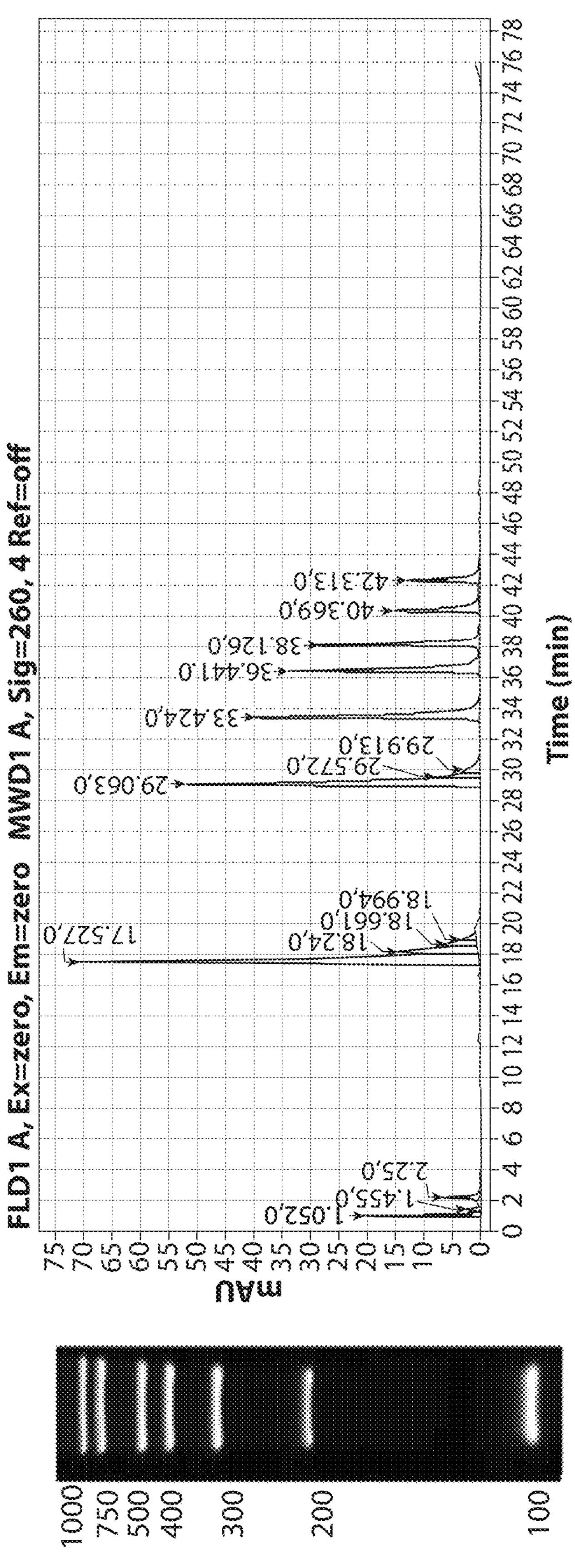
Figure 6C:
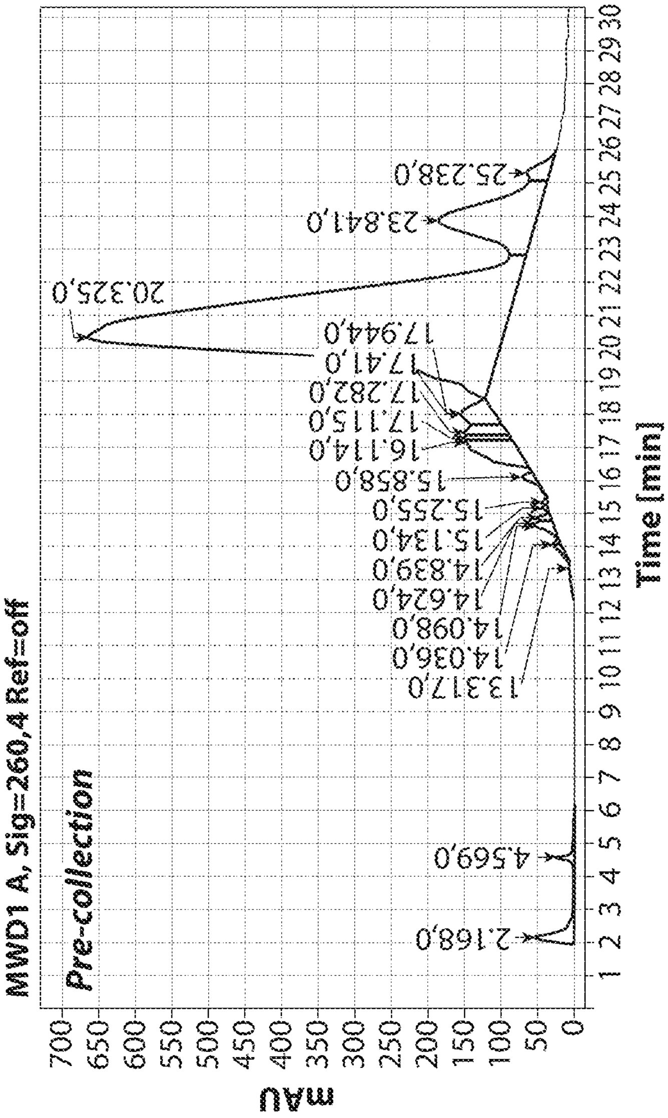
Figure 6D:
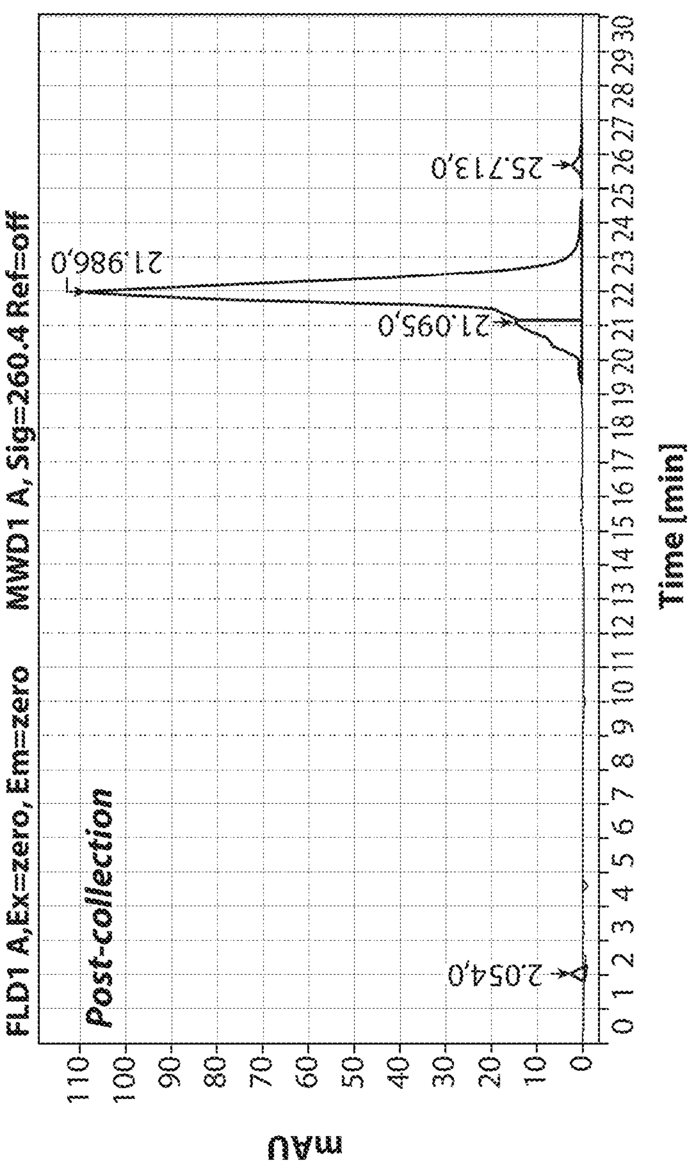
Figure 6E:
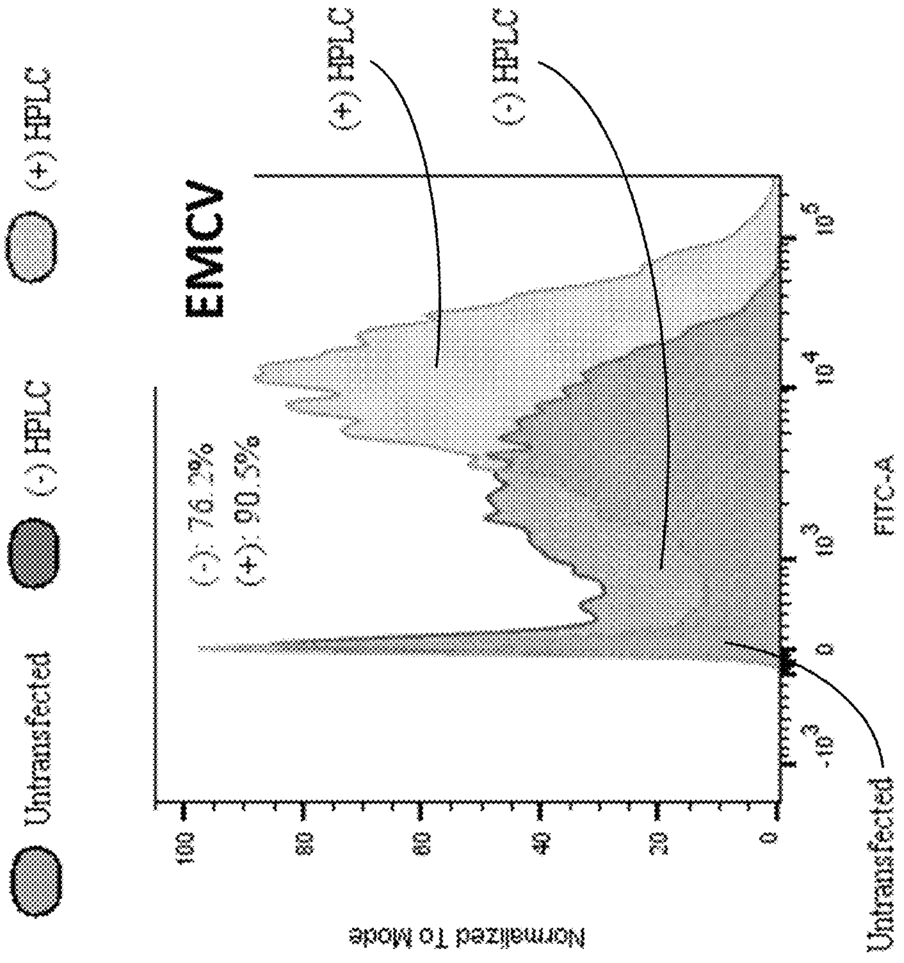
Figures 6F, 6G:
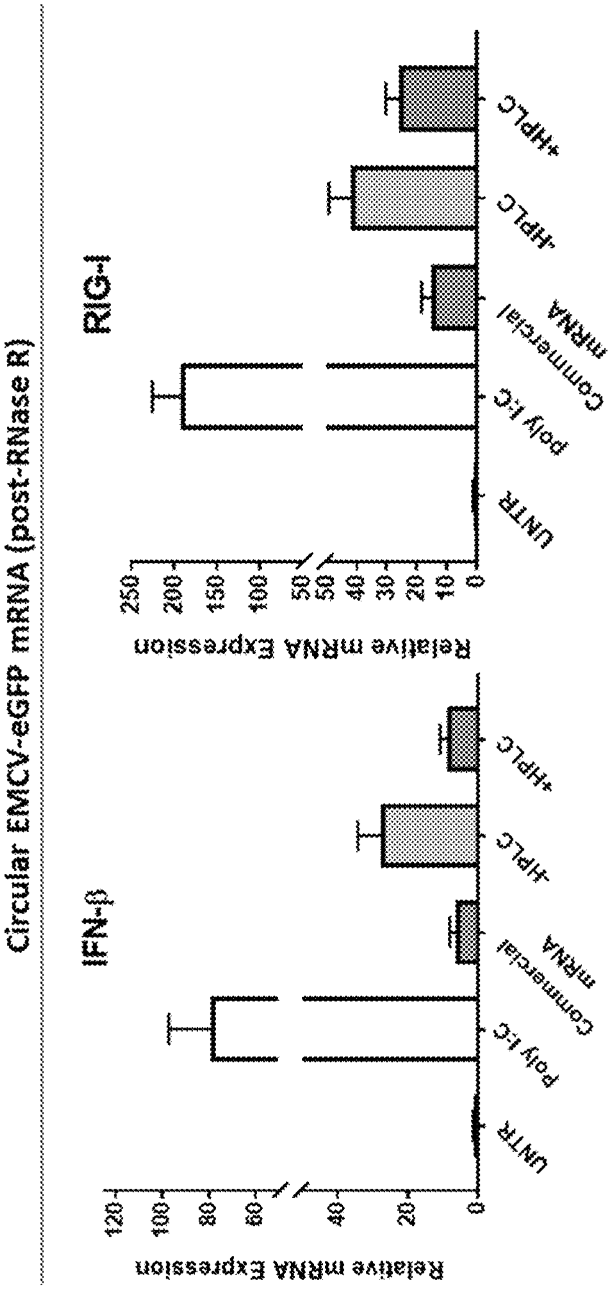

It was found that HPLC purification is necessary for removing immuno-stimulatory byproducts following RNase R digestion. In FIG. 6A, an example set of conditions for HPLC purification is shown in the boxed area with an optimized solvent gradient for separating RNAs shown at bottom (Solvent A: 0.1 M TEAA, Solvent B: 0.1 M TEAA+25% Acetonitrile). In FIG. 6B, accurate separation was confirmed by running RNA Century ladder (Life Technologies). FIG. 6C depicts chromatograms of RNase R-treated RNA upon initial runs on the HPLC column. Fractions were collected from minutes 19 through 22, purified, and re-run on the HPLC column again to confirm efficient removal of non-specific RNA (FIG. 6D). Following purification, 100 ng of circular eGFP mRNA, pre- and post-HPLC purification, was transfected into HEK293T cells (20,000 cells/well in a 96-well plate and complexed with lipofectamine 2000 transfection reagent), and translation was measured by flow cytometry 24 hours post-transfection (FIG. 6E). To evaluate mRNA-induced immune response, induction of IFN-β (FIG. 6F) and RIG-I (FIG. 6G) was tested and measured by qPCR.

Example 8: Confirmatory Methods for Verifying Circularization and Purity

Circular RNA was exposed to RNase R to remove residual linear RNA from the sample. In parallel, equal levels of the linear form of a given RNA as well as a commercial mRNA (Cleancap eGFP, Trilink) were digested alongside the circular samples to provide positive controls that are expected to be completely degraded upon exposure to RNase R.

Figure 7A:
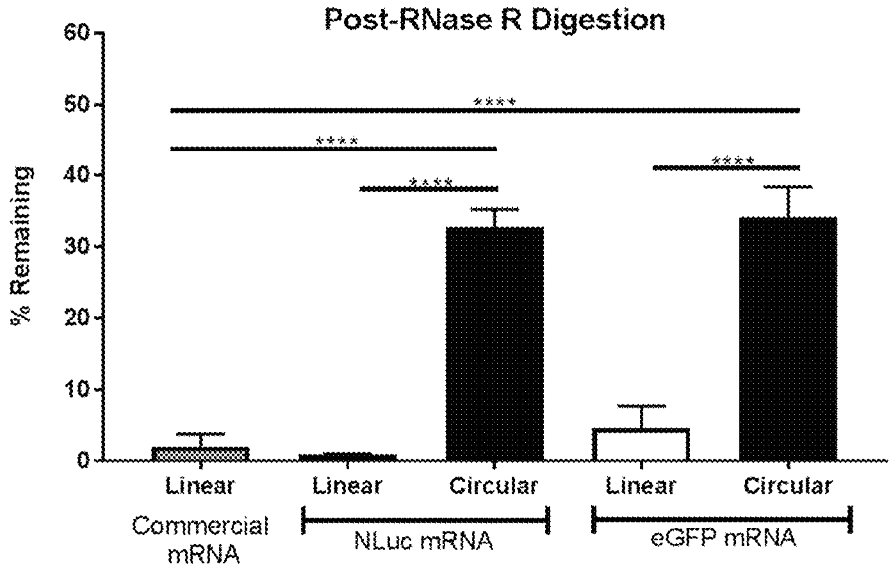
FIGS. 7A-7D depict confirmatory methods for verifying circularization and purity.
Figure 7B:
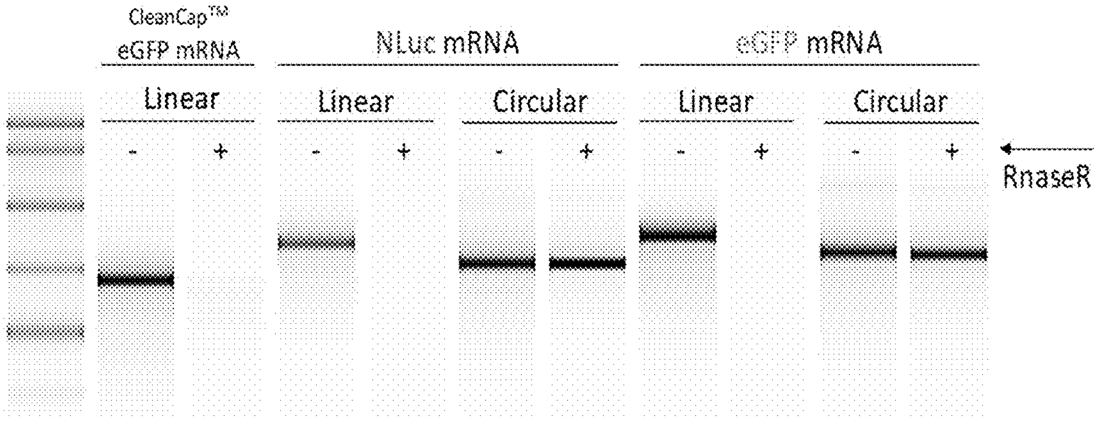

In FIG. 7A, 5 μg of linear and circular forms of an Nluc or eGFP mRNA (or Trilink's Cleancap) was exposed to 5 units of RNase R for 45 minutes at 37° C. The remaining RNA was recovered by ethanol precipitation, and the amount recovered was used to calculate circularization efficiency. These experiments were repeated 3 times in triplicate. As shown, the linear forms are completely degraded, as no RNA was recovered post-digestion. However, the circular samples have significant levels of RNA remaining post-digestion, which represents the circular RNA product. To confirm that this remaining product was indeed circular RNA, the samples were run on a Tapestation (Agilent) to confirm that the linear control RNA was completely degraded and that the recovered circular RNA was the intact target (FIG. 7B).

Figure 7C:
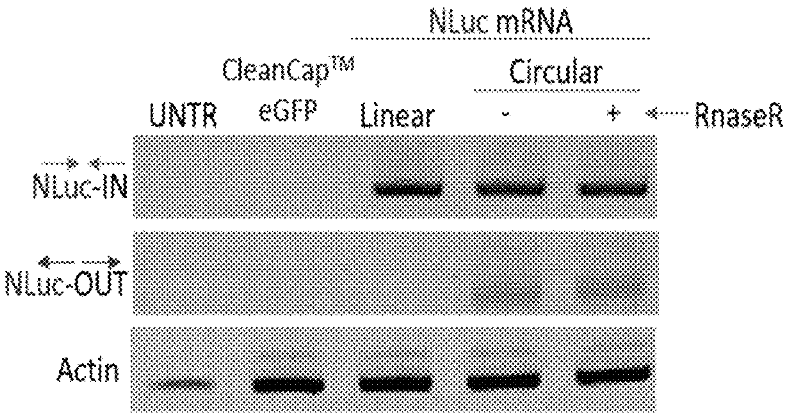
Figure 7C:
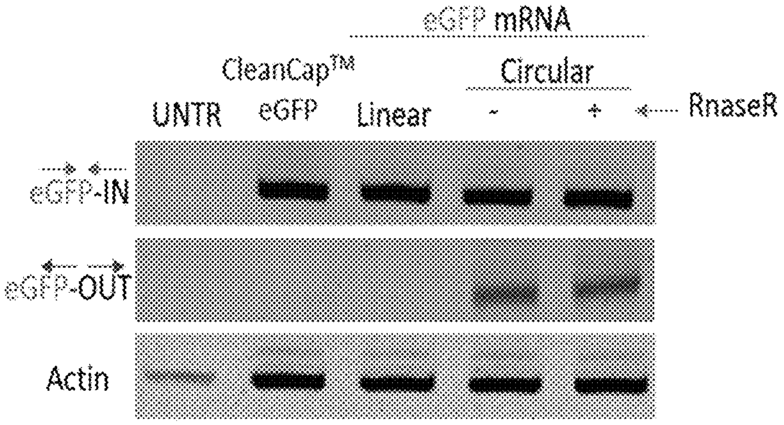
Figure 7D:
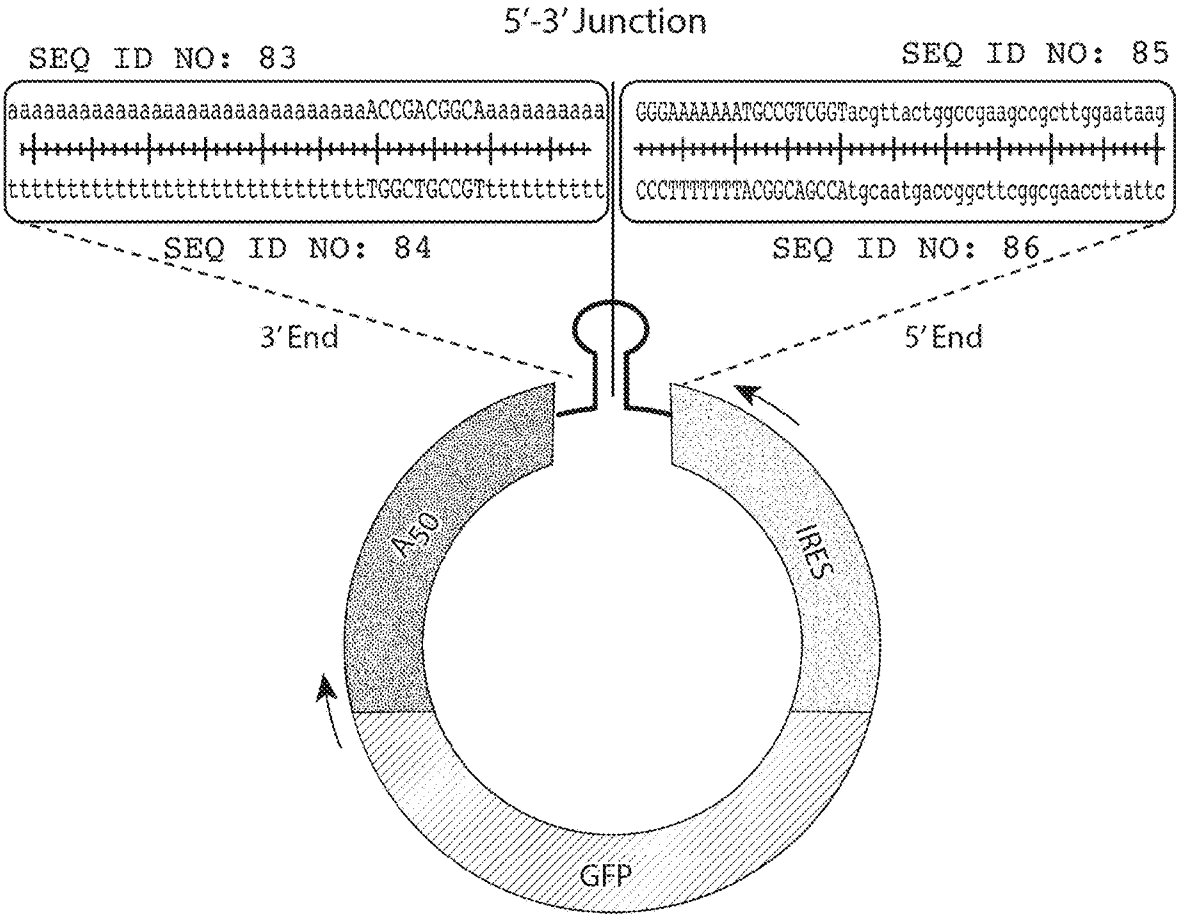

To verify ligation, the circular RNAs (and the indicated controls) were transfected into HEK293T cells, total RNA was isolated after 24 hours, and RT-PCR was performed using divergent primers (with respect to the linear construct) that amplify the region containing the 5'-3' junction. As expected, only the circular samples produce amplicon using divergent primers (FIG. 7C). As a final confirmation, the PCR products generated from the divergent primers were sequenced to confirm accurate ligation across the junction (FIG. 7D).

Example 9: Poly(A) Tailing to Promote Digestion of Linear mRNA

It was found that poly(A) tailing allows for complete RNase R digestion of residual linear mRNA in circularization reactions.

Figure 8A:
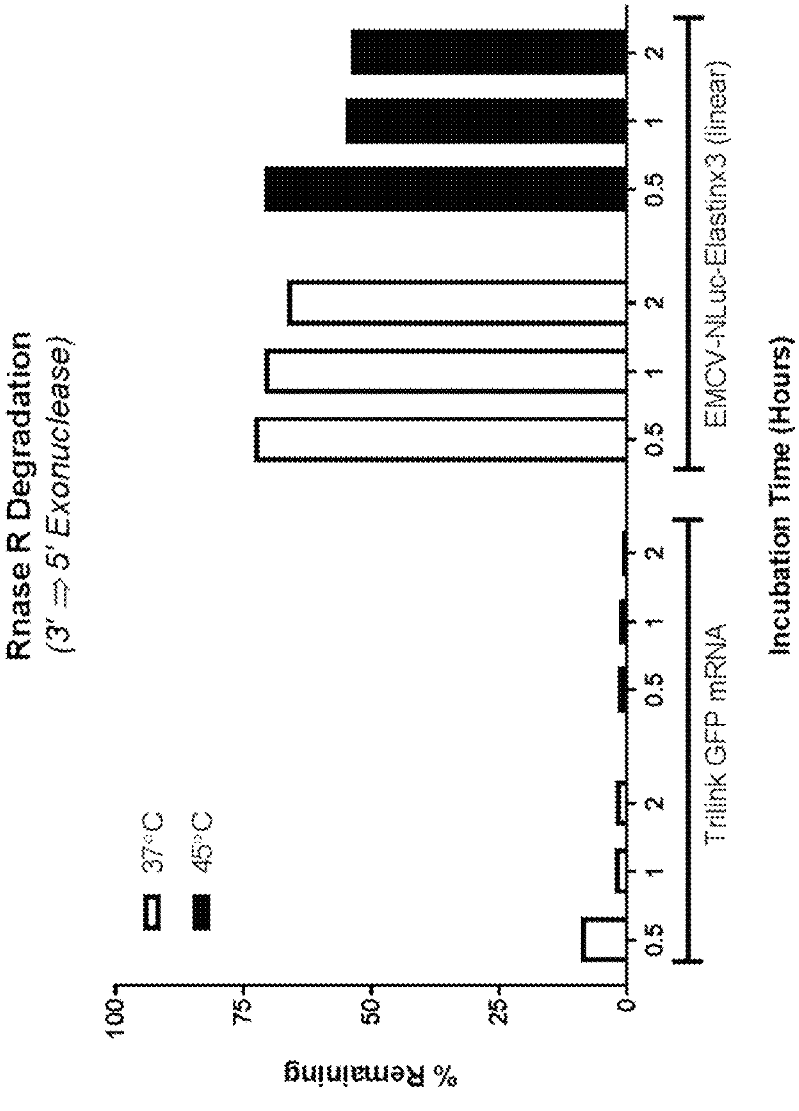
FIGS. 8A-8C depict a set of experiments evaluating the effects of poly(A) tailing on RNase R digestion of residual linear mRNA in circularization reactions.

To optimize RNase R reaction conditions, linear forms of commercial linear mRNA (Trilink) and the final constructs were exposed to the temperatures and incubation times indicated in FIG. 8A. Even in linear form, the RNA was resistant to RNase R digestion.

Figure 8B:
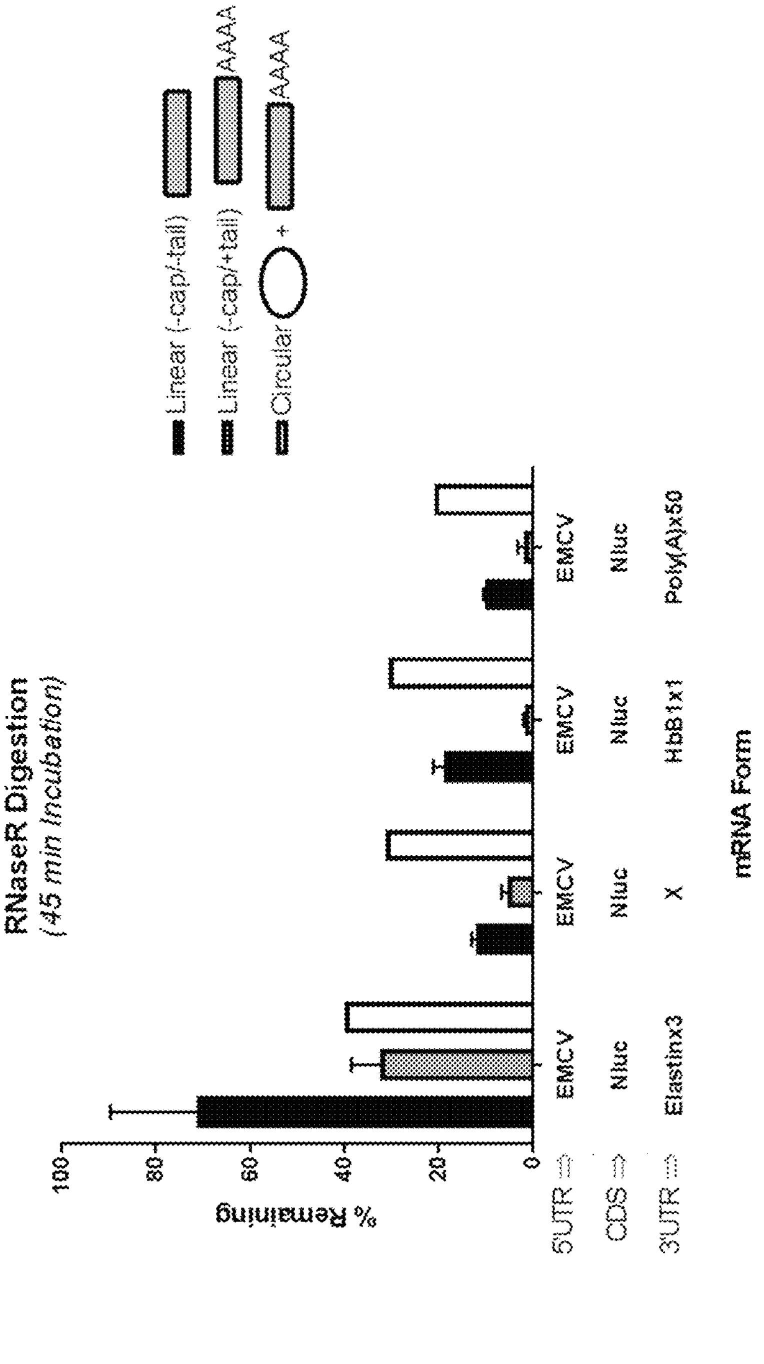

To determine if this resistance was due to the G content in the elastinx3 3' UTR of the constructs, constructs with varying 3' UTRs among 3 different forms of RNA were generated (without cap and tail, with cap and tail, and in circular form). Results for RNase R digestion of these constructs is shown in FIG. 8B.

Figure 8C:
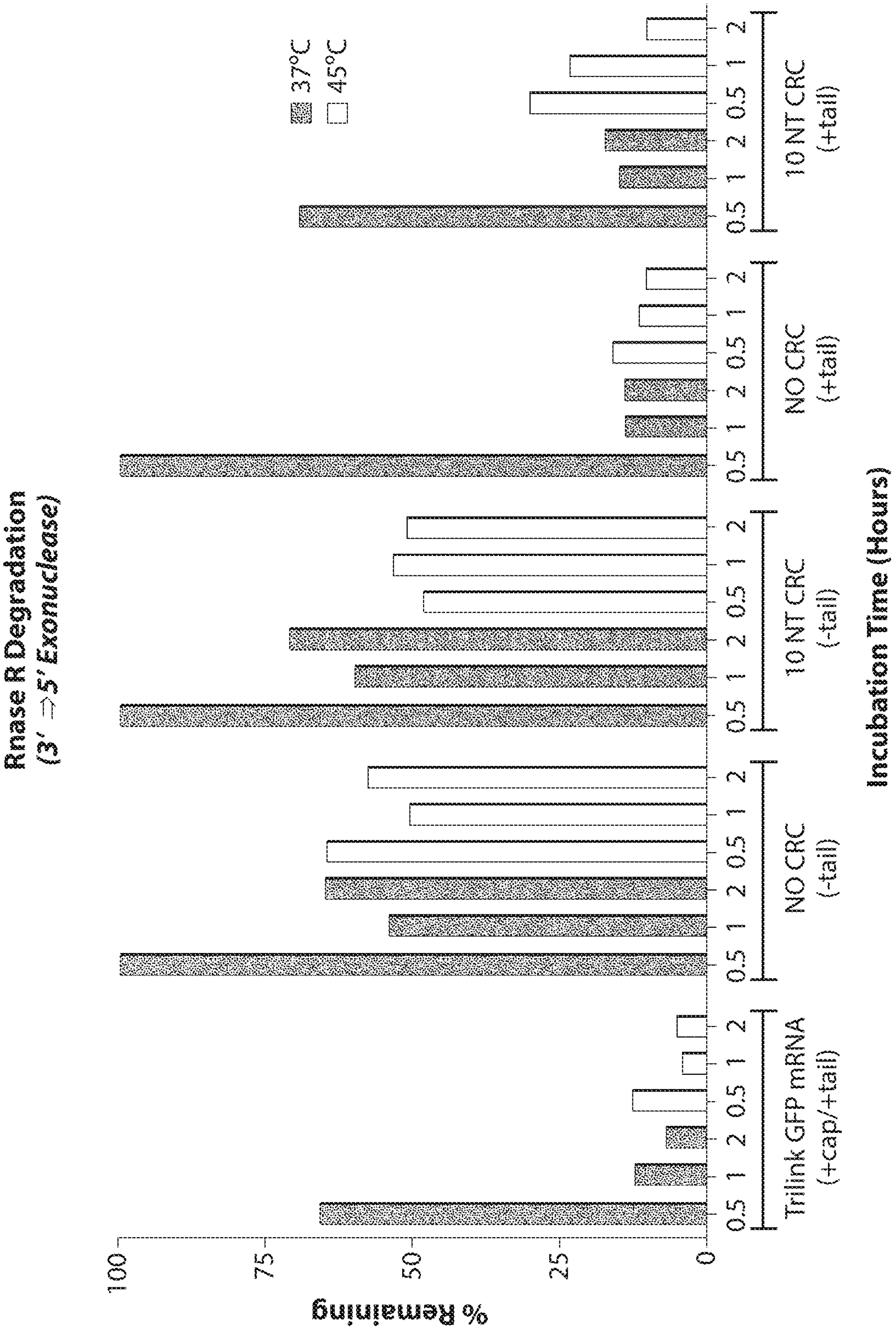

To confirm that the addition of a poly(A) stretch at the 3' end of the RNA is sufficient to allow for robust (>80%) RNase R-mediated degradation of linear RNA, linear RNA (+/−poly(A) tail and/or +/−CRC) was incubated to show that the poly(A) allowed RNAs to be sufficiently resensitized to RNase R degradation (FIG. 8C).

Figure 9A:
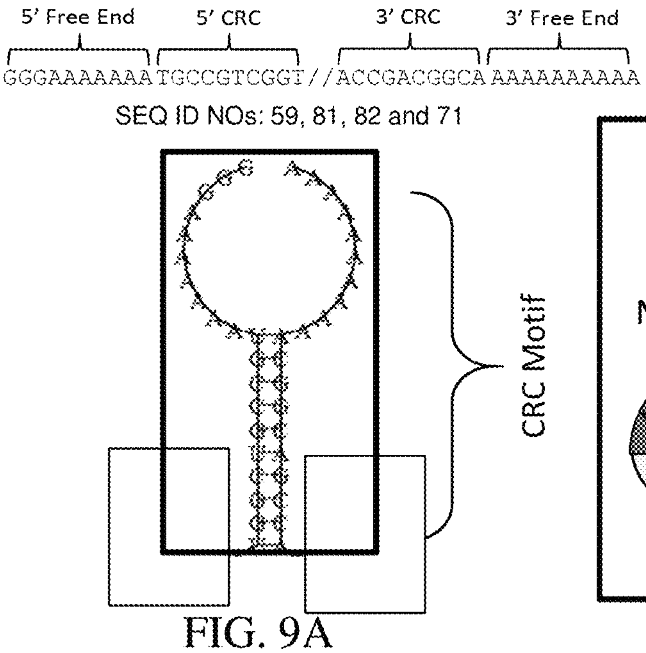
FIGS. 9A-9F depict a set of experiments showing that an optimized 10-nucleotide (NT) CRC motif significantly enhances circularization efficiency but does not hinder translation or induce an interferon response.
Figure 9B:
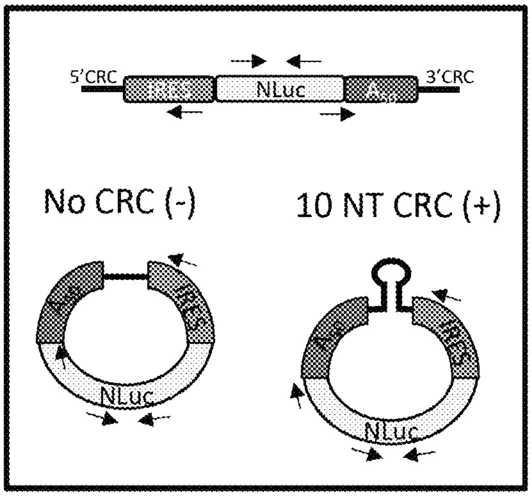
Figure 9C:
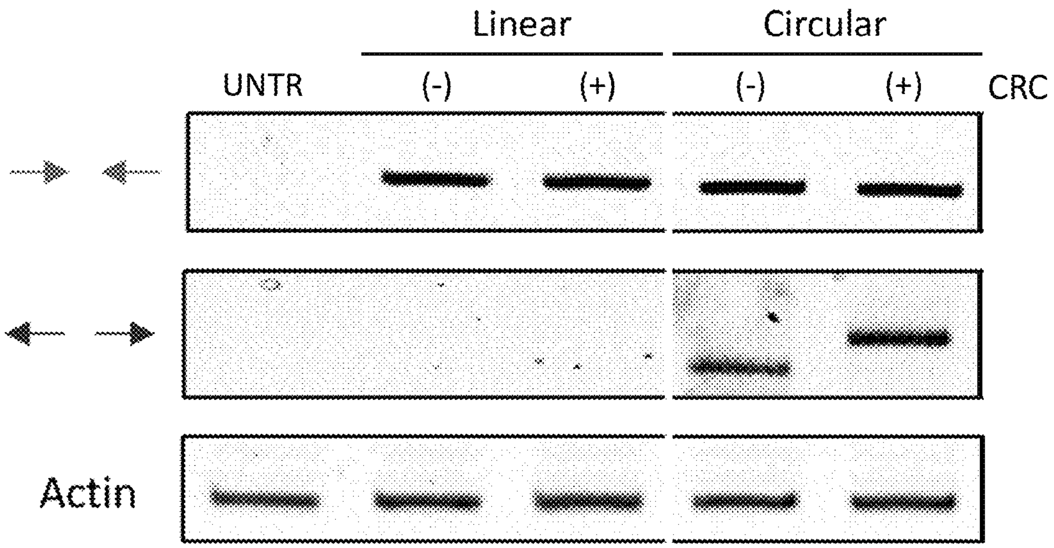

Example 10: A CRC Motif Enhances Circularization Efficiency without Hindering Translation or Inducing an Interferon Response FIG. 9A is a diagram of the predicted secondary structure of the 5' and 3' ends of an example RNA construct when the CRC is included. A set of constructs were designed to be used to characterize the effect that CRCs have on circularization efficiency, translation efficiency, and cytokine induction (FIG. 9B). FIG. 9C depicts confirmation that the indicated constructs were generated correctly and that circular RNA was produced.

Figure 9D:
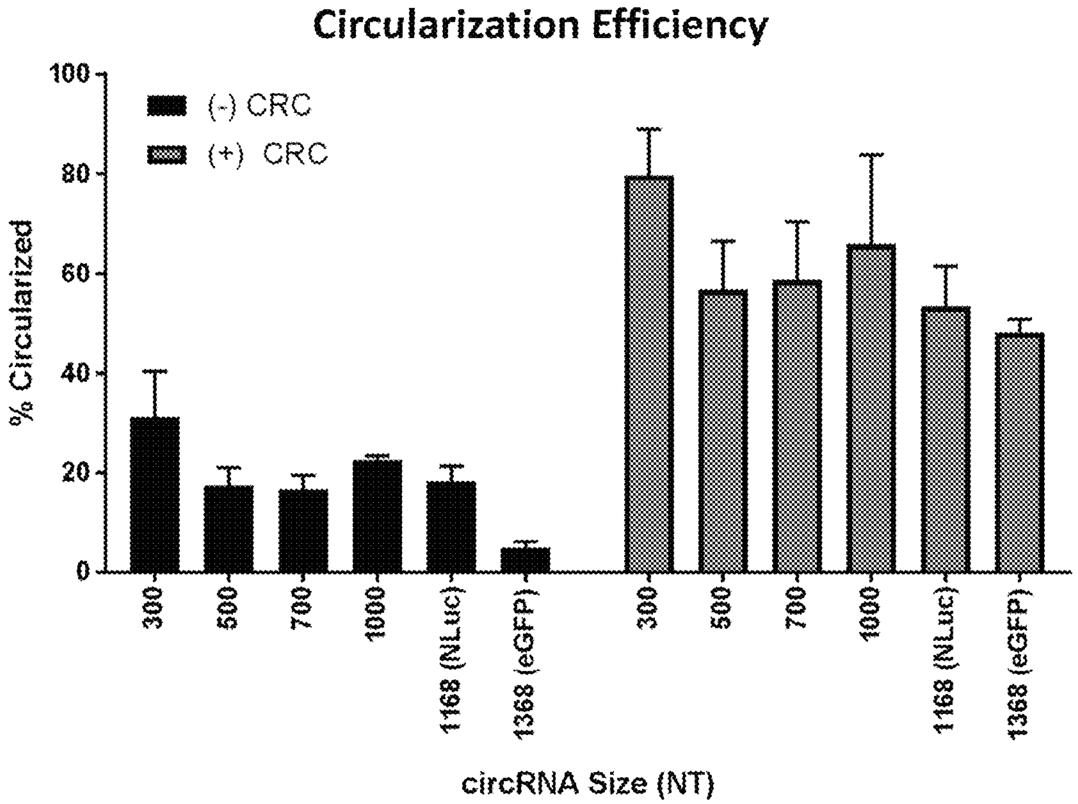

To evaluate circularization efficiency, a panel of constructs varying in their size and the presence of CRC were circularized and digested with RNase R. The presence of a CRC at the ends of these constructs greatly enhanced the amount of circular RNA produced (FIG. 9D).

Figure 9E:
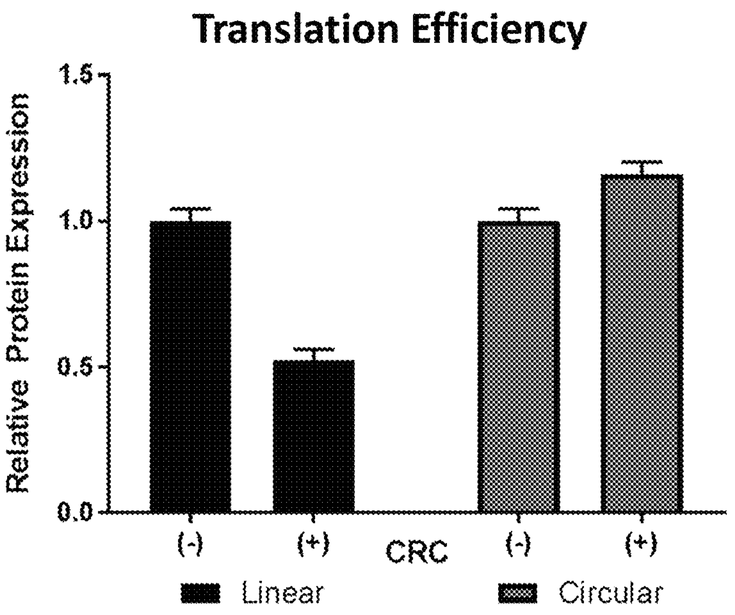
Figure 9F:
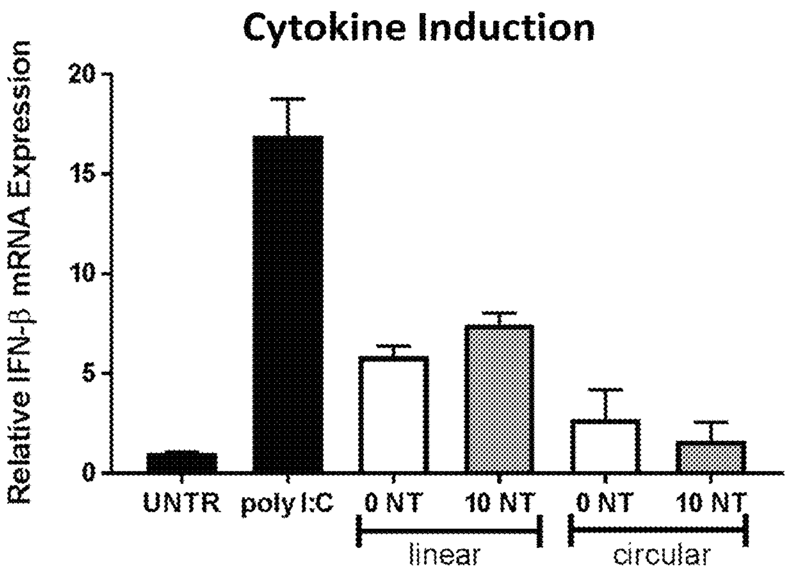

To evaluate translation efficiency, a Nanoluciferase (Nluc)-encoding RNA construct was transfected into HEK293T cells, and the variations in protein expression (as measured by luciferase activity) were compared (FIG. 9E). As shown, there was no change in protein expression when a 10-nucleotide CRC was added to circular RNA.

To evaluate cytokine response, IFNβ induction was measured, and it was confirmed that the addition of this 10-nucleotide CRC motif did not significantly induce a type I interferon response.

Figure 10A:
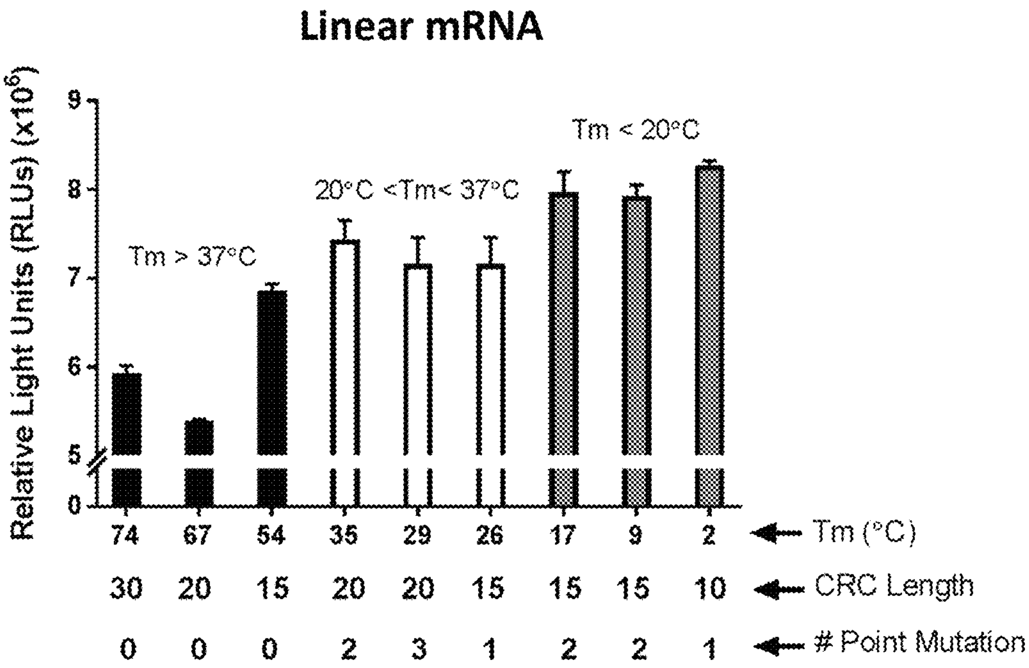
FIGS. 10A-10B depict an evaluation of the effects of CRC melting temperature on translational capacity of linear RNA (FIG. 10A) and circular RNA (FIG. 10B).
Figure 10B:
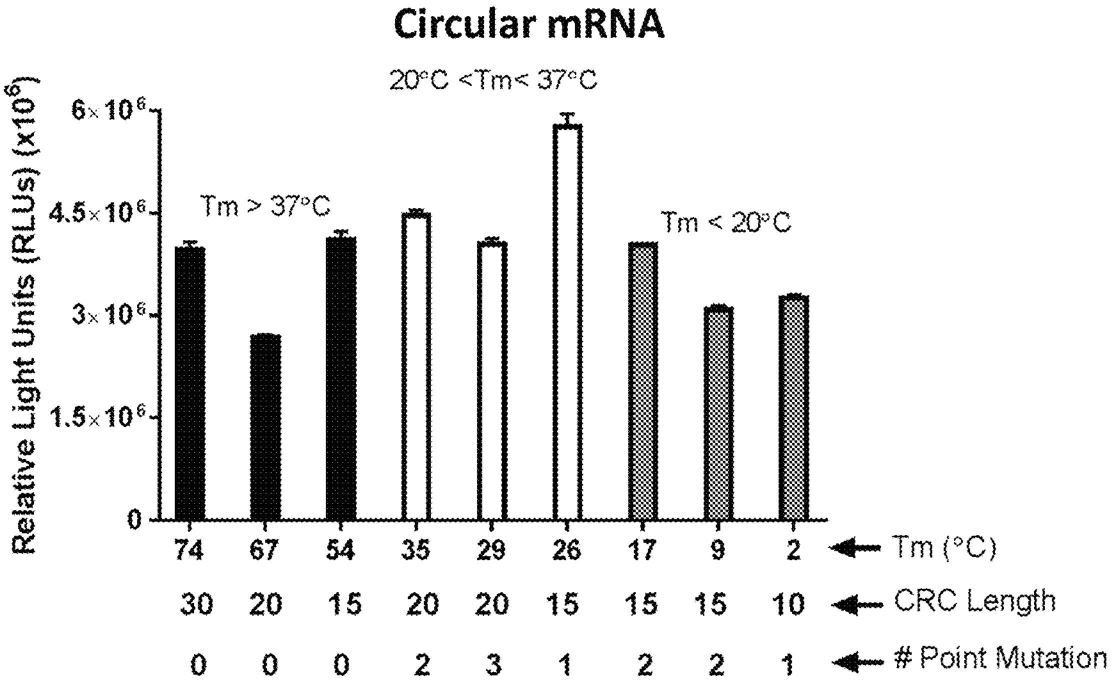

Example 11: Effects of CRC Melting Temperature on Translational Capacity of Linear and Circular RNA Each construct listed in FIG. 4A was generated in linear or circular form and purified by HPLC. The resulting purified products were used as templates in a reticulocyte lysate cell-free translation system (400 ng of mRNA per reaction). The linear mRNA showed increased protein levels as the CRC's $T_m$ decreased (FIG. 10A). In contrast, the circular mRNA showed no such trend (FIG. 10B).

Example 12: Persistence of Circular mRNA is Observed in Vitro and in Vivo

Figure 11A:
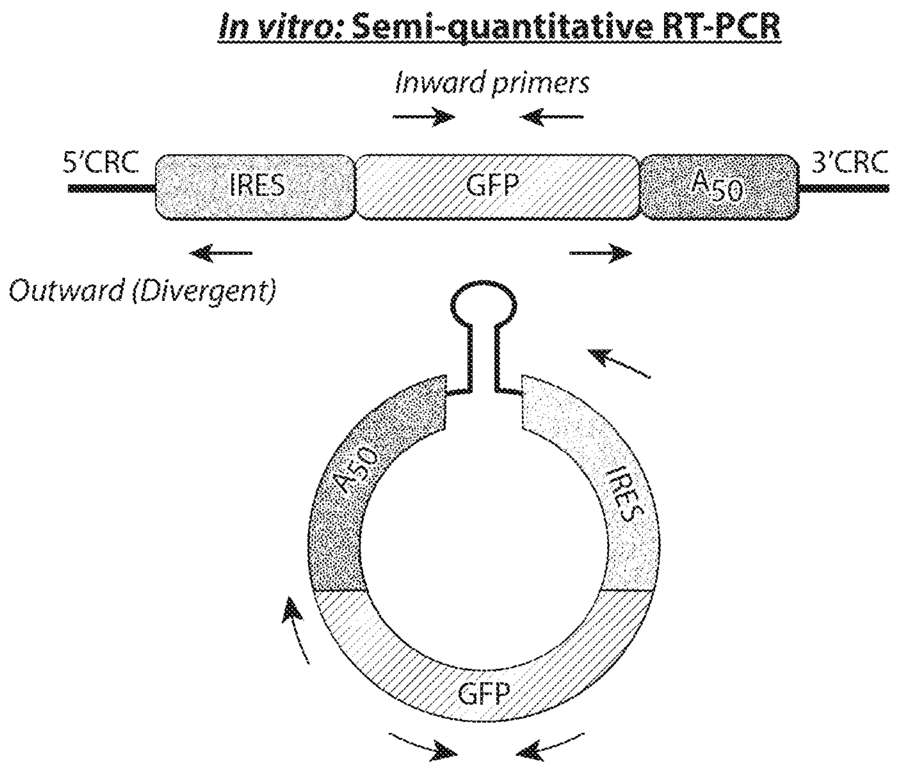
FIGS. 11A-11E depict a set of experiments evaluating persistence of mRNA in vitro and in vivo.
Figure 11B:
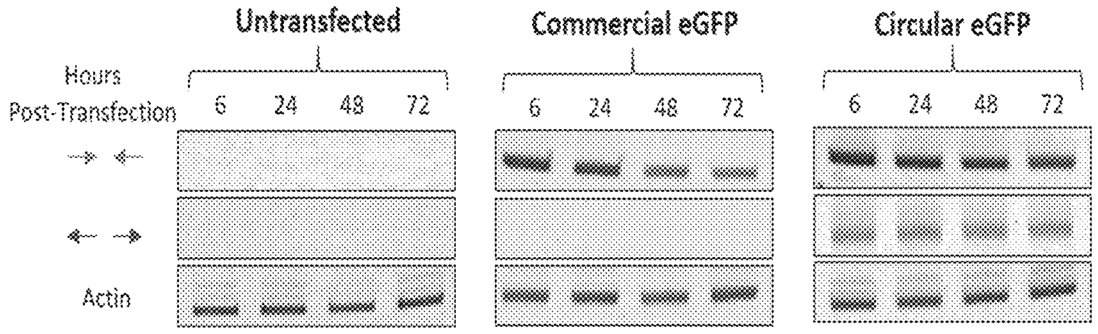

A diagram of a target mRNA and its corresponding amplicons when using inward- and outward-oriented primers in semi-quantitative RT-PCR is shown in FIG. 11A. HepG2 cells were transfected with commercial eGFP (5mC/PseudoU+HPLC purification) or circular mRNA (unmodified NTs, +HPLC purification), and total mRNA was isolated 6, 24, 48, or 72 hours post-transfection. cDNA was generated from total mRNA, and RT-PCR was carried out using the primer pairs outlined in FIG. 11A to monitor mRNA stability over the indicated time course.

Figure 11C:
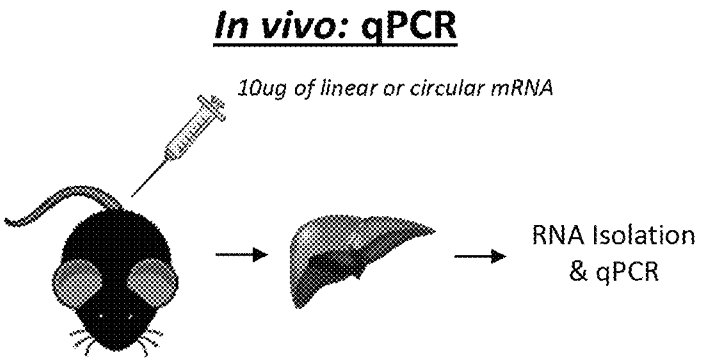
Figure 11D:
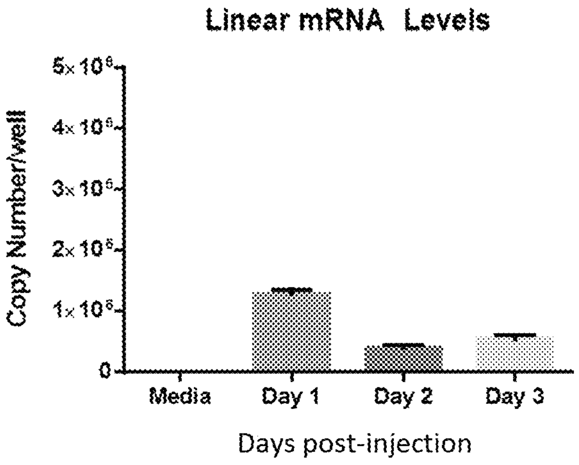
Figure 11E:
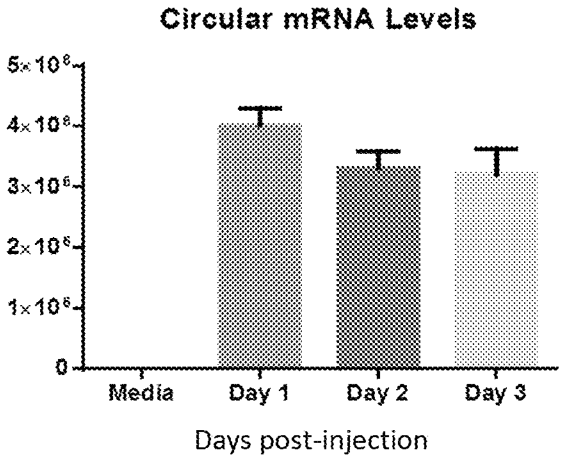

BALB/c mice were injected intravenously (FIG. 11C) with 10 μg of linear (+cap/+tail) (FIG. 11D) or circular (FIG. 11E) mRNA complexed to TransIT, or TransIT alone. Total mRNA was isolated from liver homogenates 24, 48, or 72 hours post injection, and absolute values of mRNA were determined by qPCR.

Figure 12A:
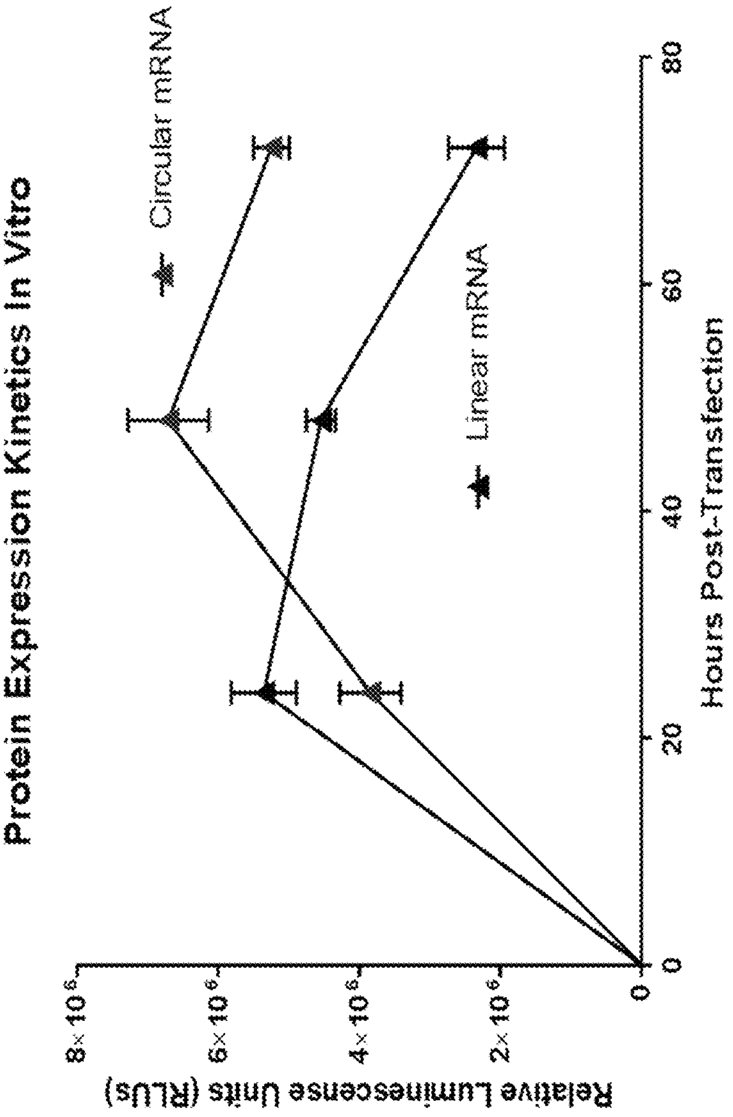
FIGS. 12A-12C depict a set of experiments evaluating persistence of EMCV-IRES-mediated protein translation in circular mRNA.
Figure 12B:
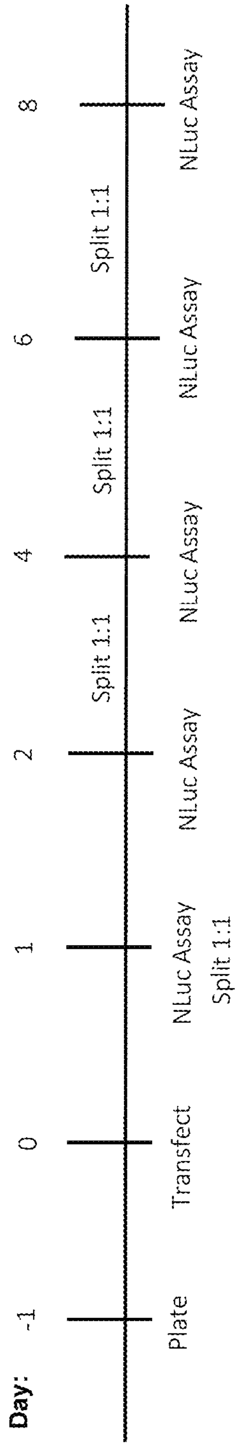
Figure 12C:
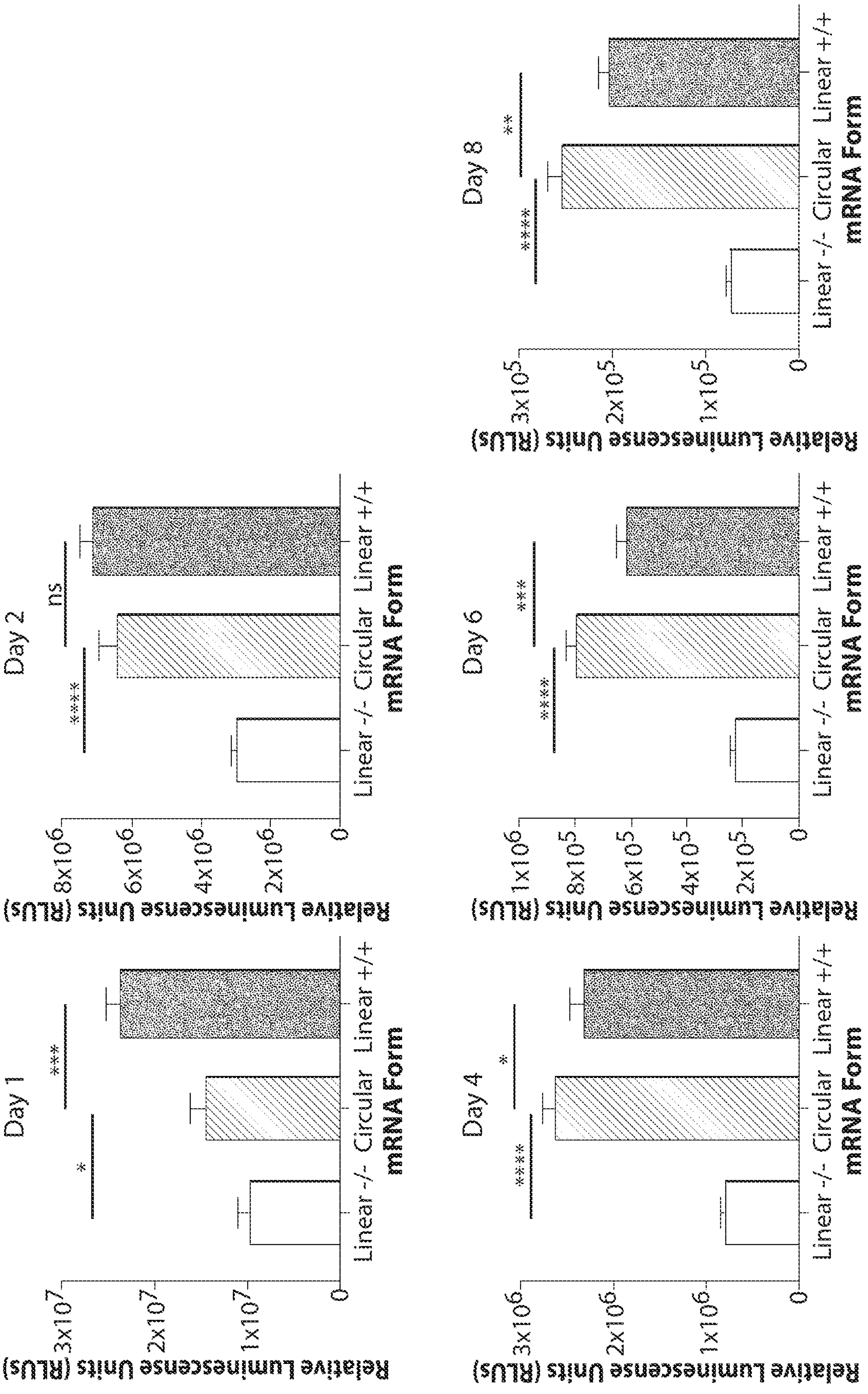

Example 13: EMCV-IRES-Mediated Protein Translation in Circular mRNA Persists Longer than that Derived from Canonical Linear mRNA Protein expression kinetics from circular mRNA versus linear mRNA (both encoding Nluc) was tracked over a 3-day time course in HepG2 cells (FIG. 12A). To characterize protein expression in HEK293T cells past 3 days, cells were sequentially split and assayed every other day as outlined in FIG. 12B. As shown in FIG. 12C, protein levels of circular mRNA continued to rise and surpass linear +/+ levels by Day 2 and continued this trend until Day 8.

Figures 13A, 13B:
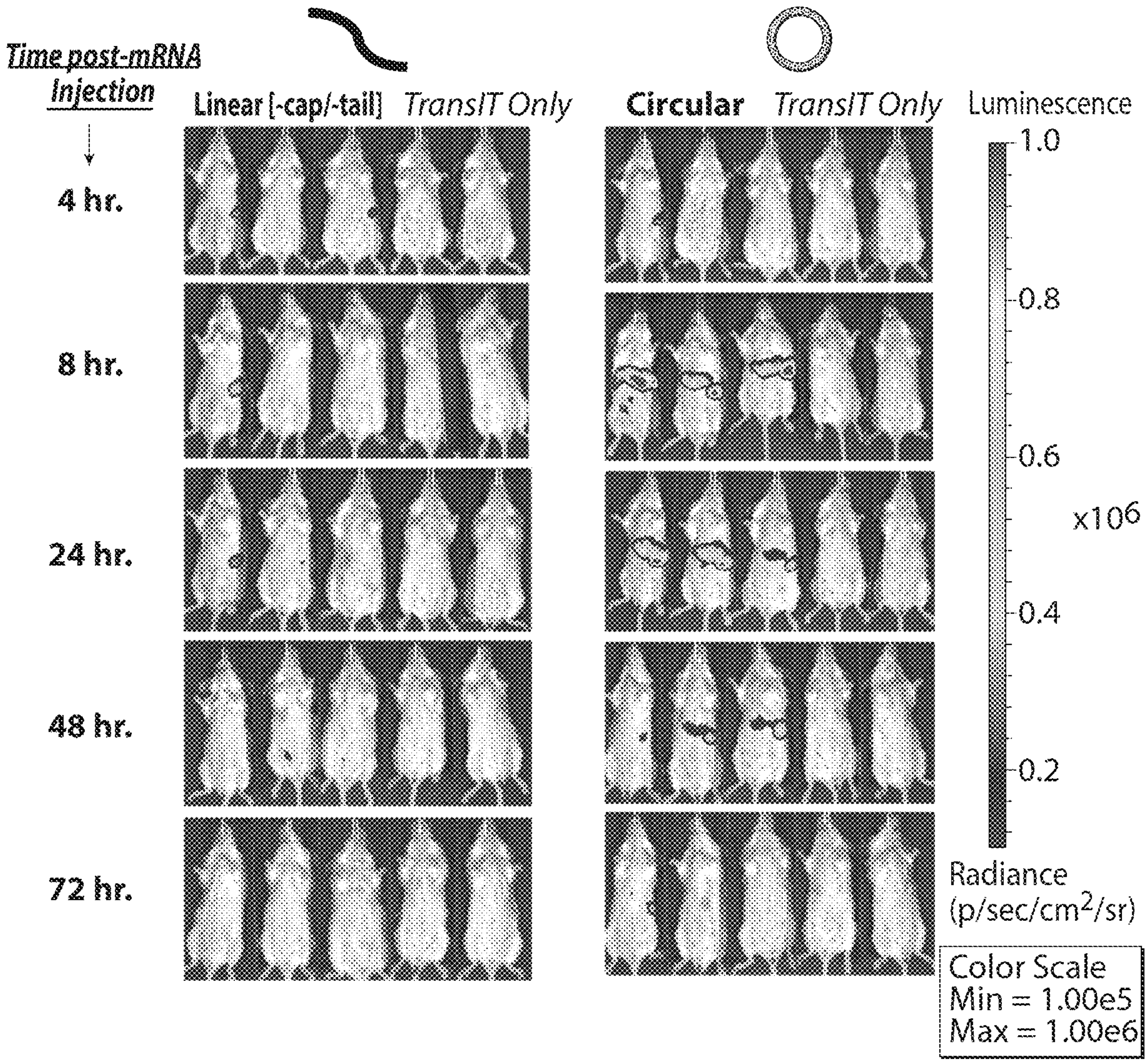
FIGS. 13A-13B depict live bioluminescence imaging of mice injected with linear (FIG. 13A) or circular (FIG. 13B) RNA.

Example 14: Circular mRNA can be Robustly Expressed in Vivo Following Intravenous Injection 10 μg of Nluc-encoding linear (FIG. 13A) or circular (FIG. 13B) RNA complexed to TransIT was injected intravenously into BALB/c mice. Expression was measured by IVIS at 4, 8, 24, 48, and 72 hours post-injection. The two different forms of RNA are identical in sequence and vary only in the status of their 3' and 5' end; the linear form has ends that are accessible for exonuclease-mediated degradation, while the circular form's 5' and 3' ends have been covalently ligated. The lack of free ends in the latter construct results in significantly greater levels of protein expression of this extended time course.

Example 15: Erythropoietin (Epo) Construct Design and Confirmation

Figure 14A:
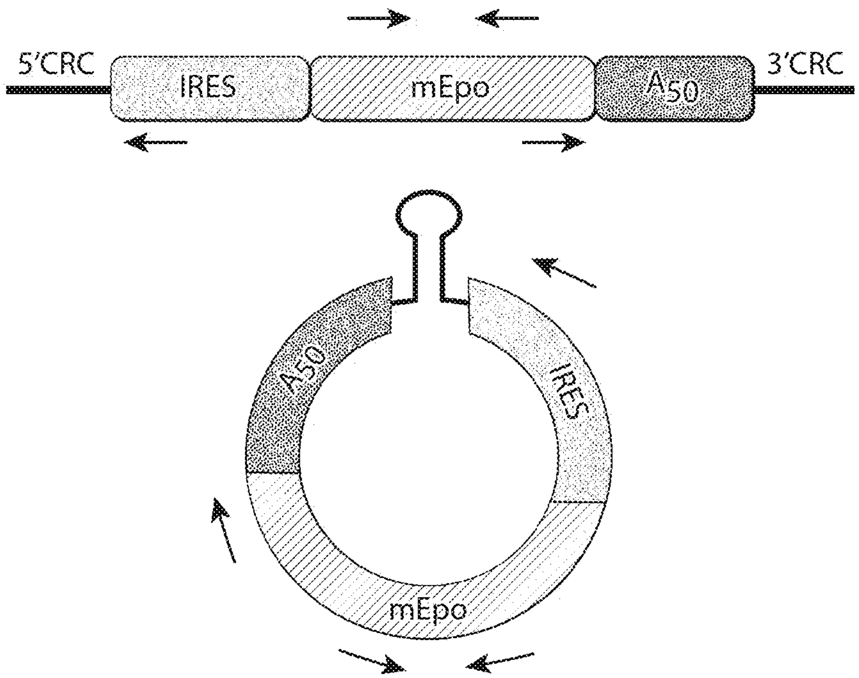
FIGS. 14A-14E depict erythropoietin (EPO) construct design and confirmation.
Figure 14B:
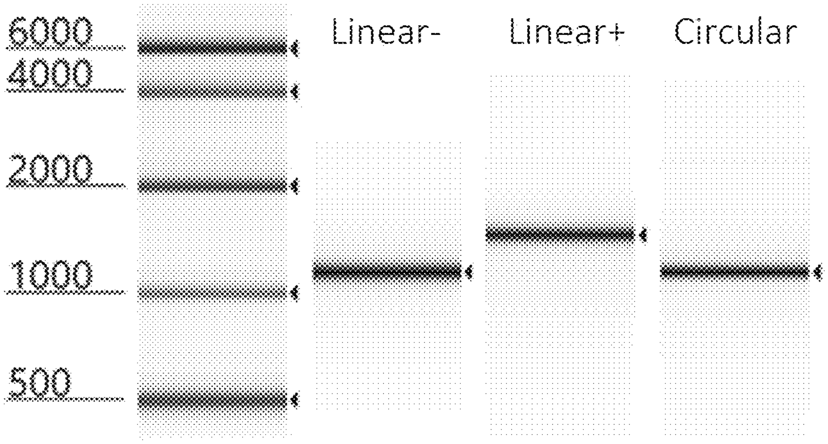
Figure 14C:
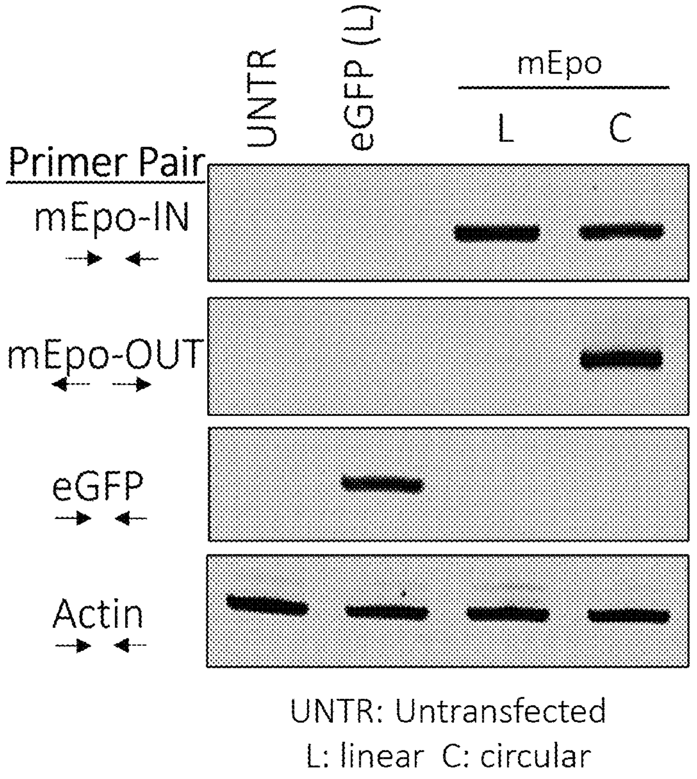
Figure 14D:
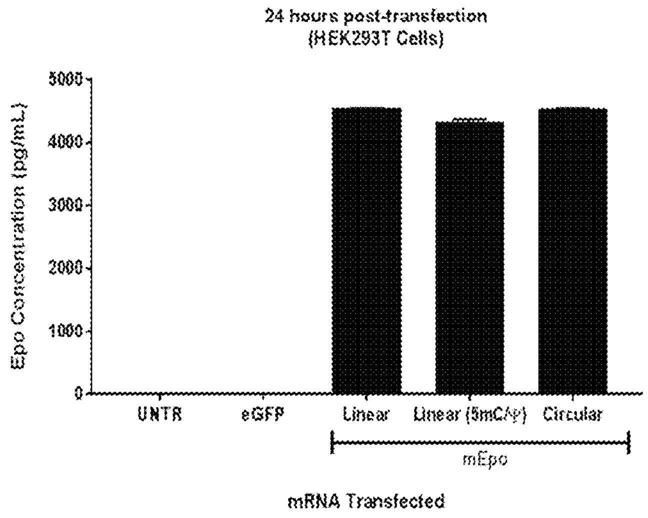
Figure 14E:
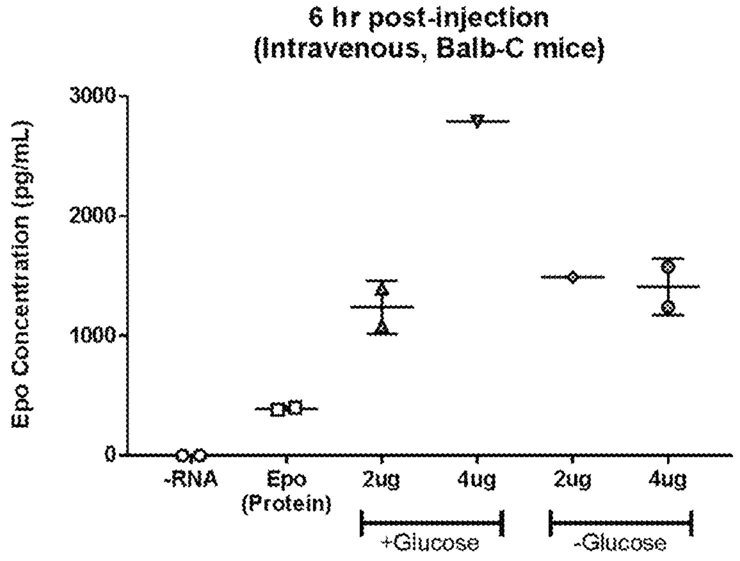

A codon-optimized mouse erythropoietin mRNA was generated with an EMCV 5' UTR and a poly(A)x50 in its 3' UTR (FIG. 14A), and the size and purity of the RNA was confirmed by TapeStation (Agilent) (FIG. 14B). Successful ligation was confirmed using RT-PCR and sequence-specific divergent primers (FIG. 14C). Final products were initially tested in immortalized cells (HEK293T cells) to confirm translation of the generated mRNA (FIG. 14D). Epo protein secretion was measured by ELISA. FIG. 14E depicts optimization of Epo mRNA injected intravenously into BALB/c mice.

Figure 15A:
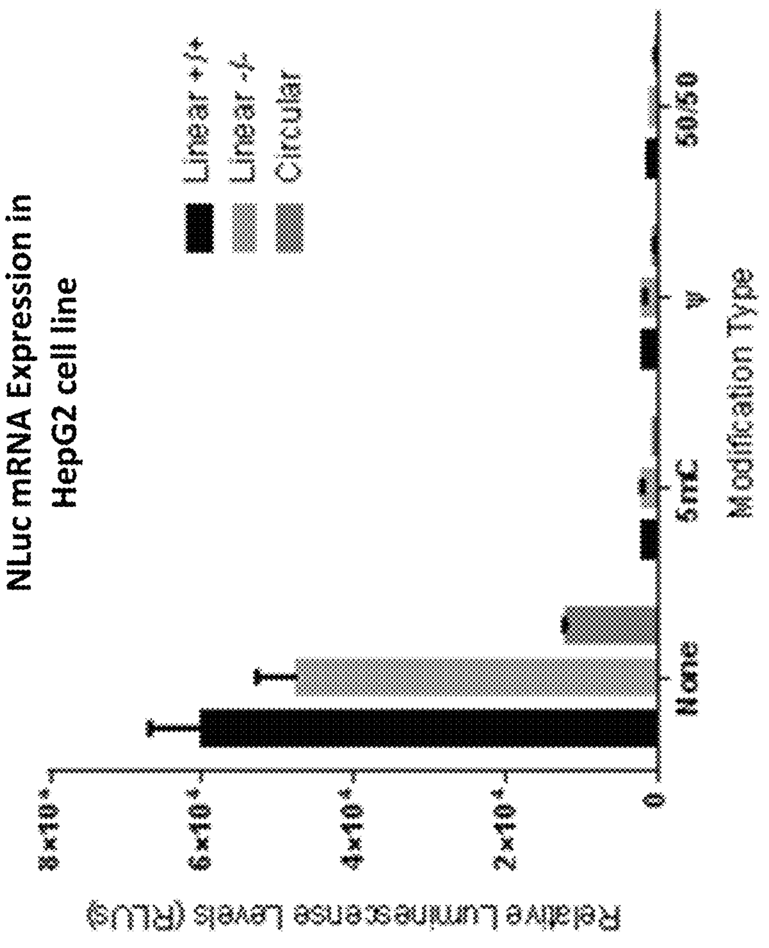
FIGS. 15A-15E depict a set of experiments evaluating EMCV-mediated translation of RNA having modified nucleotides.
Figure 15B:
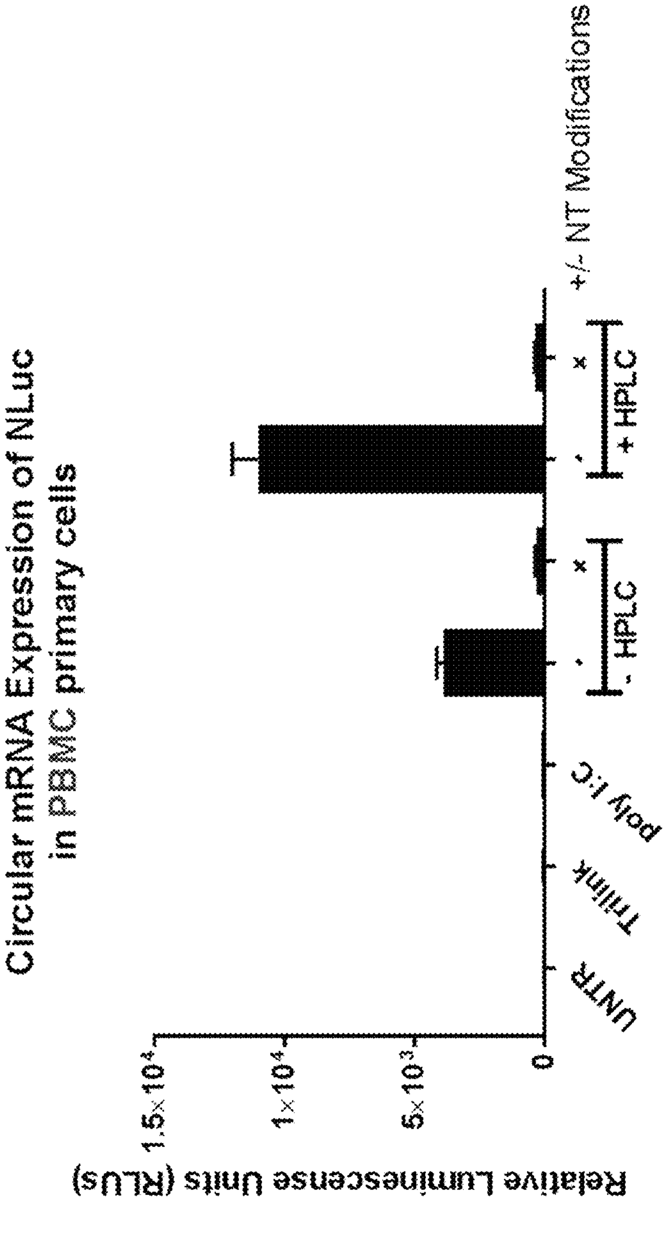

Example 16: EMCV-Mediated Protein Translation is Inhibited in Immortalized Cell Lines and Primary Cells when Modified Nucleotides are Incorporated into the mRNA but Maintains Its Functionality in Vivo As shown in FIGS. 15A-15B, mRNAs containing modified nucleotides in their sequences are not able to translate protein if translation is dependent on the EMCV IRES. Protein expression is undetectable in HepG2 cells (FIG. 15A) and PBMCs (FIG. 15B), both 24 hours post-transfection.

Figure 15C:
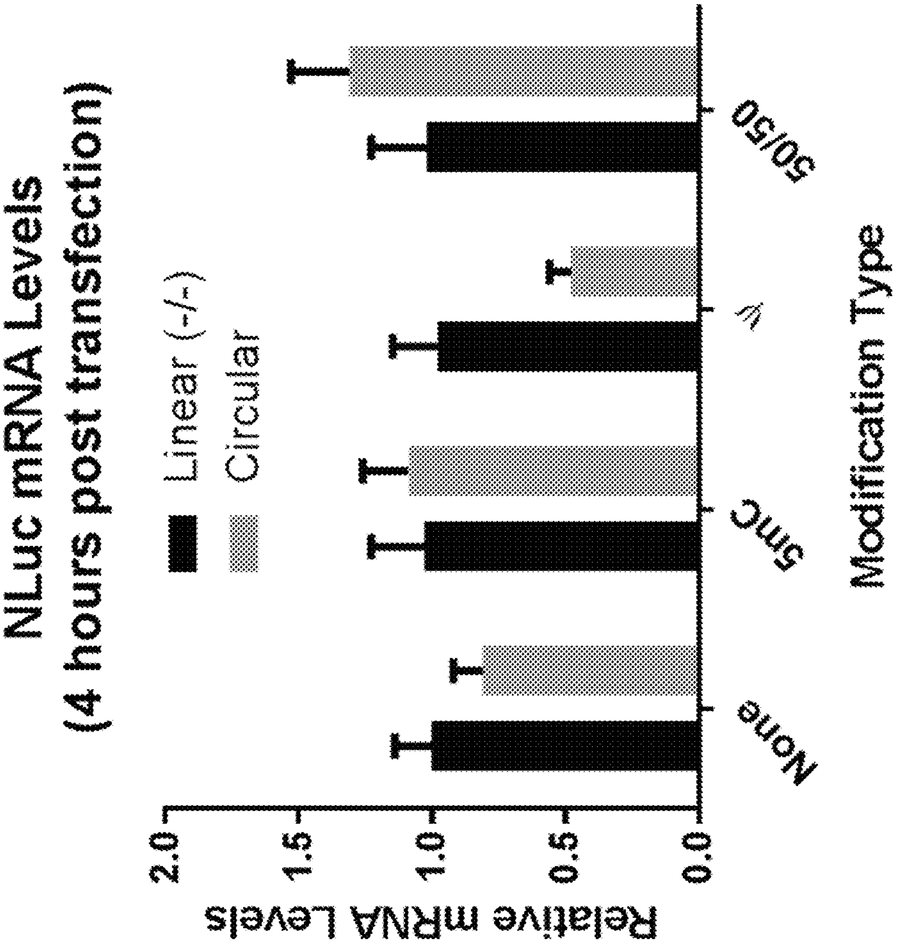
Figure 15D:
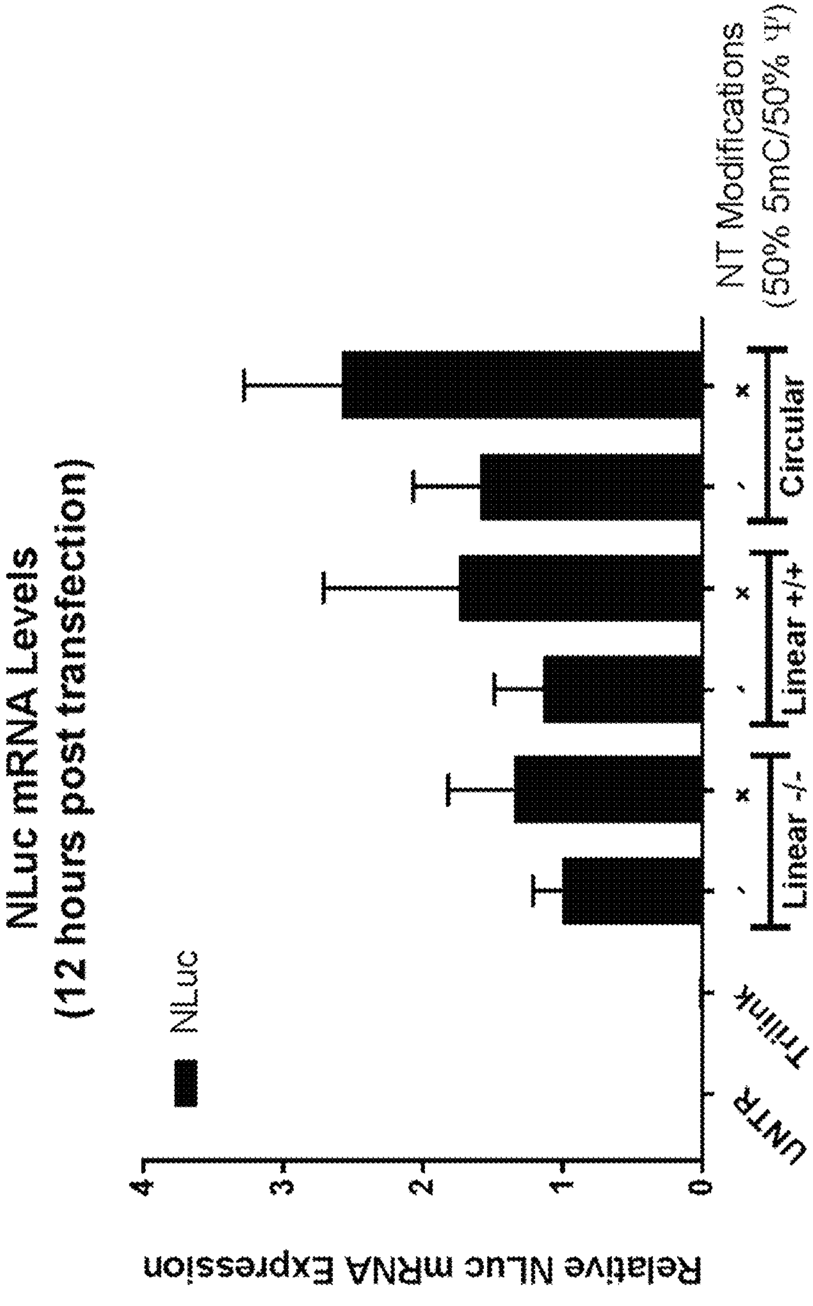

The lack of protein expression is not due to disparate levels of RNA present within the cell, as roughly equal levels of RNA are detected within the cell at early time points: 4 hours post-transfection in HepG2 cells (FIG. 15C) and 12 hours post-transfection in PBMCs (FIG. 15D).

Figure 15E:
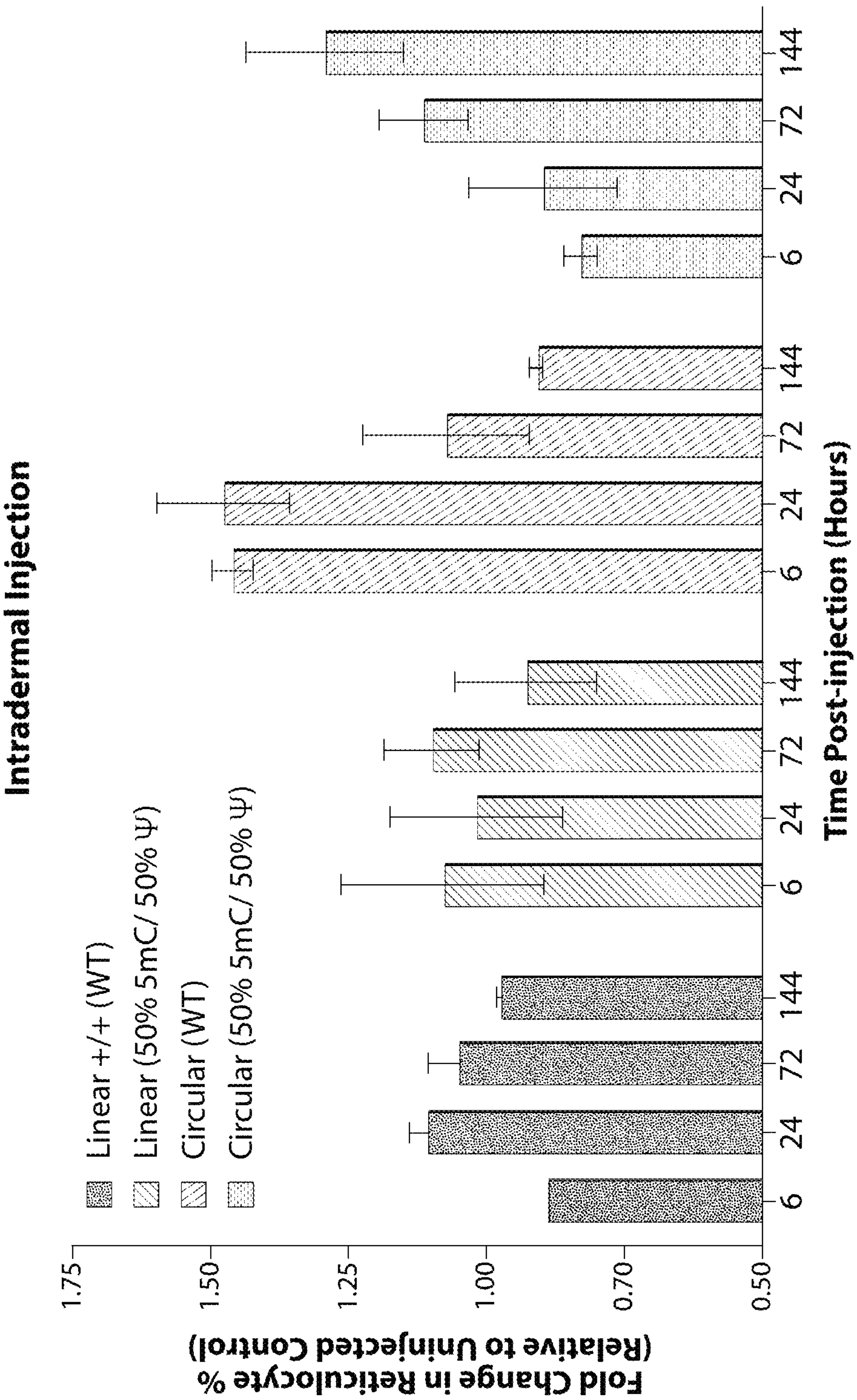

2 μg of mEpo mRNA in linear or circular form (+/− nucleotide modifications) was injected into mice intradermally. As a functional readout for mEpo protein production, reticulocyte counts in whole blood were measured at 6, 24, 72, and 144 hours post-injection using a flow-based assay (BD Bioscience, Retic-Counter). As shown in FIG. 15E, circular RNA containing nucleotide modifications is the only construct that induces an increase in reticulocyte % at each consecutive time point, suggesting that this mRNA is producing functional amounts of protein sufficient to induce a physiological response.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method for purifying circularized RNA relative to linear RNA, wherein the circularized RNA encodes a chimeric antigen receptor (CAR), and wherein the method comprises the steps of:

a. providing a sample comprising a mixed population of circularized RNA and linear RNA, b. separating the circularized RNA and linear RNA by subjecting the sample to gel or column chromatography, and c. obtaining a composition of circularized RNA that is substantially free of linear RNA.

2. The method of claim 1, wherein the composition of step c comprises up to about 15% linear RNA.

3. The method of claim 2, wherein the composition comprises between about 0.1% and 10% linear RNA.

4. The method of claim 2, wherein the composition comprises between about 0.5% and 5% linear RNA.

5. The method of claim 2, wherein the composition comprises between about 0.5% and 1% linear RNA.

6. The method of claim 2, wherein the composition comprises between about 1% and 5% linear RNA.

7. The method of claim 2, wherein the composition comprises between about 0.1% and 1% linear RNA.

8. The method of claim 2, wherein the composition comprises between about 0.1% and 0.5% linear RNA.

9. The method of claim 2, wherein the composition comprises between about 0.01% and 0.1% linear RNA.

10. The method of claim 2, wherein the composition comprises between about 0.05% and 0.1% linear RNA.

11. The method of claim 1, wherein the circularized RNA and linear RNA of the sample are separated by gel chromatography.

12. The method of claim 1, wherein the circularized RNA and linear RNA of the sample are separated by column chromatography.

13. The method of claim 12, wherein the column chromatography comprises a high-performance liquid chromatography (HPLC) technique.

14. The method of claim 13, wherein the HPLC technique is ion-pair reversed-phase HPLC.

15. The method of claim 12, wherein said column chromatography comprises:

a. providing the sample to a purification column;

b. eluting the circularized nucleic acid by passing a liquid through the purification column, wherein the liquid comprises a solvent gradient; and c. collecting an eluate comprising the circularized nucleic acid.

16. The method of claim 15, wherein the purification column comprises a stationary phase comprising a plurality of microspheres.

17. The method of claim 16, wherein the plurality of microspheres comprises a polystyrene-divinylbenzene copolymer.

18. The method of claim 1 further comprising, following (a) and prior to (b), contacting the sample with an exonuclease under digestion conditions to degrade the linear RNA.

19. The method of claim 18, wherein the linear RNA comprises a polyadenylation sequence.

20. The method of claim 18, wherein the exonuclease comprises a poly(A) polymerase, the sample is subjected to column chromatography, and the column chromatography comprises a HPLC column.

21. The method of claim 18, wherein the sample is subjected to a polyadenylation tailing reaction.

22. The method of claim 12, wherein the column chromatography comprises affinity chromatography.

23. The method of claim 12, wherein the column chromatography comprises ion-exchange chromatography.

24. A method of claim 1, wherein the circularized RNA comprises chemically modified nucleotide analogs selected from the group consisting of N6-methyladenosine, 5-methylcytidine, pseudouridine, 2-thiouridine, N1-methylpseudouridine, and thienoguanosine.

* * * * *

SEQUENCE LISTING

```
Sequence total quantity: 95
SEQ ID NO: 1            moltype = DNA  length = 30
FEATURE                 Location/Qualifiers
source                  1..30
                        mol_type = other DNA
                        organism = synthetic construct
SEQUENCE: 1
gcacgaattg cacaatcggt acgttcgagt                                  30

SEQ ID NO: 2            moltype = DNA  length = 30
FEATURE                 Location/Qualifiers
source                  1..30
                        mol_type = other DNA
                        organism = synthetic construct
SEQUENCE: 2
gttacgtacc aacacgttat tgccgtcggt                                  30

SEQ ID NO: 3            moltype = DNA  length = 20
FEATURE                 Location/Qualifiers
source                  1..20
                        mol_type = other DNA
                        organism = synthetic construct
SEQUENCE: 3
gcacgaattg cacaatcggt                                             20

SEQ ID NO: 4            moltype = DNA  length = 20
FEATURE                 Location/Qualifiers
source                  1..20
                        mol_type = other DNA
                        organism = synthetic construct
SEQUENCE: 4
tggctgcacg aattgcacaa                                             20
```

```
SEQ ID NO: 5            moltype = DNA  length = 20
FEATURE                 Location/Qualifiers
source                  1..20
                        mol_type = other DNA
                        organism = synthetic construct
SEQUENCE: 5
gtacgtggct gcacgaattg                                             20

SEQ ID NO: 6            moltype = DNA  length = 15
FEATURE                 Location/Qualifiers
source                  1..15
                        mol_type = other DNA
                        organism = synthetic construct
SEQUENCE: 6
gcacgaattg cacaa                                                  15

SEQ ID NO: 7            moltype = DNA  length = 15
FEATURE                 Location/Qualifiers
source                  1..15
                        mol_type = other DNA
                        organism = synthetic construct
SEQUENCE: 7
tggctgcacg aattg                                                  15

SEQ ID NO: 8            moltype = DNA  length = 30
FEATURE                 Location/Qualifiers
source                  1..30
                        mol_type = other DNA
                        organism = synthetic construct
SEQUENCE: 8
actcgaaaga acagaatgta caaatcgtgc                                  30

SEQ ID NO: 9            moltype = DNA  length = 30
FEATURE                 Location/Qualifiers
source                  1..30
                        mol_type = other DNA
                        organism = synthetic construct
SEQUENCE: 9
accgaaggca ttaaagtgat ggaacataac                                  30

SEQ ID NO: 10           moltype = DNA  length = 30
FEATURE                 Location/Qualifiers
source                  1..30
                        mol_type = other DNA
                        organism = synthetic construct
SEQUENCE: 10
accgtcggaa atgacgtatt gattcgtaac                                  30

SEQ ID NO: 11           moltype = DNA  length = 30
FEATURE                 Location/Qualifiers
source                  1..30
                        mol_type = other DNA
                        organism = synthetic construct
SEQUENCE: 11
accgtcggaa atgacgtatt gataggtaac                                  30

SEQ ID NO: 12           moltype = DNA  length = 30
FEATURE                 Location/Qualifiers
source                  1..30
                        mol_type = other DNA
                        organism = synthetic construct
SEQUENCE: 12
actcaaaagt aacgaatgtg aaattagtgc                                  30

SEQ ID NO: 13           moltype = DNA  length = 30
FEATURE                 Location/Qualifiers
source                  1..30
                        mol_type = other DNA
                        organism = synthetic construct
SEQUENCE: 13
accgacagca acaacctgct ggtacataac                                  30

SEQ ID NO: 14           moltype = DNA  length = 30
FEATURE                 Location/Qualifiers
source                  1..30
                        mol_type = other DNA
                        organism = synthetic construct
SEQUENCE: 14
actcaagcgt actgagtgtg gaactagtgc                                  30
```

```
SEQ ID NO: 15          moltype = DNA  length = 30
FEATURE                Location/Qualifiers
source                 1..30
                       mol_type = other DNA
                       organism = synthetic construct
SEQUENCE: 15
accgccggaa atgacgtatt gataggtaac                                   30

SEQ ID NO: 16          moltype = DNA  length = 30
FEATURE                Location/Qualifiers
source                 1..30
                       mol_type = other DNA
                       organism = synthetic construct
SEQUENCE: 16
accgtcggaa attaagtatt gatacgtaac                                   30

SEQ ID NO: 17          moltype = DNA  length = 30
FEATURE                Location/Qualifiers
source                 1..30
                       mol_type = other DNA
                       organism = synthetic construct
SEQUENCE: 17
actcaaacat aacgatagtg caaatagtgc                                   30

SEQ ID NO: 18          moltype = DNA  length = 30
FEATURE                Location/Qualifiers
source                 1..30
                       mol_type = other DNA
                       organism = synthetic construct
SEQUENCE: 18
actcaagcgt acggaatgtg gaaatggtgc                                   30

SEQ ID NO: 19          moltype = DNA  length = 30
FEATURE                Location/Qualifiers
source                 1..30
                       mol_type = other DNA
                       organism = synthetic construct
SEQUENCE: 19
actccaacat acagatagtg caaatagtgc                                   30

SEQ ID NO: 20          moltype = DNA  length = 30
FEATURE                Location/Qualifiers
source                 1..30
                       mol_type = other DNA
                       organism = synthetic construct
SEQUENCE: 20
accgccggaa atcacgtatt gataggtaac                                   30

SEQ ID NO: 21          moltype = DNA  length = 30
FEATURE                Location/Qualifiers
source                 1..30
                       mol_type = other DNA
                       organism = synthetic construct
SEQUENCE: 21
actcaaacat acagatagtg caaatagtgc                                   30

SEQ ID NO: 22          moltype = DNA  length = 30
FEATURE                Location/Qualifiers
source                 1..30
                       mol_type = other DNA
                       organism = synthetic construct
SEQUENCE: 22
accgacagca acaacttgct gctatgtaac                                   30

SEQ ID NO: 23          moltype = DNA  length = 30
FEATURE                Location/Qualifiers
source                 1..30
                       mol_type = other DNA
                       organism = synthetic construct
SEQUENCE: 23
actcaaaagt aacgaatgtg aaaatagtgc                                   30

SEQ ID NO: 24          moltype = DNA  length = 30
FEATURE                Location/Qualifiers
source                 1..30
                       mol_type = other DNA
                       organism = synthetic construct
SEQUENCE: 24
```

```
accgacagca acaacctgct gctatgtaac                                30

SEQ ID NO: 25          moltype = DNA  length = 20
FEATURE                Location/Qualifiers
source                 1..20
                       mol_type = other DNA
                       organism = synthetic construct
SEQUENCE: 25
accgattgag ctatacgtgc                                           20

SEQ ID NO: 26          moltype = DNA  length = 20
FEATURE                Location/Qualifiers
source                 1..20
                       mol_type = other DNA
                       organism = synthetic construct
SEQUENCE: 26
ttgtacaatt catgcagcca                                           20

SEQ ID NO: 27          moltype = DNA  length = 20
FEATURE                Location/Qualifiers
source                 1..20
                       mol_type = other DNA
                       organism = synthetic construct
SEQUENCE: 27
accgattgtc caatccgtgc                                           20

SEQ ID NO: 28          moltype = DNA  length = 20
FEATURE                Location/Qualifiers
source                 1..20
                       mol_type = other DNA
                       organism = synthetic construct
SEQUENCE: 28
ttgtggaatc cgtggagcca                                           20

SEQ ID NO: 29          moltype = DNA  length = 20
FEATURE                Location/Qualifiers
source                 1..20
                       mol_type = other DNA
                       organism = synthetic construct
SEQUENCE: 29
caatacgtgc cgccaggtac                                           20

SEQ ID NO: 30          moltype = DNA  length = 20
FEATURE                Location/Qualifiers
source                 1..20
                       mol_type = other DNA
                       organism = synthetic construct
SEQUENCE: 30
accggttgtg aaattggtgc                                           20

SEQ ID NO: 31          moltype = DNA  length = 20
FEATURE                Location/Qualifiers
source                 1..20
                       mol_type = other DNA
                       organism = synthetic construct
SEQUENCE: 31
ttgtccaatt cctgcagcca                                           20

SEQ ID NO: 32          moltype = DNA  length = 20
FEATURE                Location/Qualifiers
source                 1..20
                       mol_type = other DNA
                       organism = synthetic construct
SEQUENCE: 32
accgcttatg cagttcgtgc                                           20

SEQ ID NO: 33          moltype = DNA  length = 20
FEATURE                Location/Qualifiers
source                 1..20
                       mol_type = other DNA
                       organism = synthetic construct
SEQUENCE: 33
caattagtga agcctcgtac                                           20

SEQ ID NO: 34          moltype = DNA  length = 20
FEATURE                Location/Qualifiers
source                 1..20
                       mol_type = other DNA
                       organism = synthetic construct
```

```
SEQUENCE: 34
accgactgtg ccattggtgc                                        20

SEQ ID NO: 35          moltype = DNA  length = 20
FEATURE                Location/Qualifiers
source                 1..20
                       mol_type = other DNA
                       organism = synthetic construct
SEQUENCE: 35
accgtttgtt caatttgtgc                                        20

SEQ ID NO: 36          moltype = DNA  length = 20
FEATURE                Location/Qualifiers
source                 1..20
                       mol_type = other DNA
                       organism = synthetic construct
SEQUENCE: 36
accggttgta caatccgtgc                                        20

SEQ ID NO: 37          moltype = DNA  length = 20
FEATURE                Location/Qualifiers
source                 1..20
                       mol_type = other DNA
                       organism = synthetic construct
SEQUENCE: 37
accggttgtc caatccgtgc                                        20

SEQ ID NO: 38          moltype = DNA  length = 20
FEATURE                Location/Qualifiers
source                 1..20
                       mol_type = other DNA
                       organism = synthetic construct
SEQUENCE: 38
accgaatgag ctatacgtgc                                        20

SEQ ID NO: 39          moltype = DNA  length = 20
FEATURE                Location/Qualifiers
source                 1..20
                       mol_type = other DNA
                       organism = synthetic construct
SEQUENCE: 39
caattcatgc atccaggtac                                        20

SEQ ID NO: 40          moltype = DNA  length = 20
FEATURE                Location/Qualifiers
source                 1..20
                       mol_type = other DNA
                       organism = synthetic construct
SEQUENCE: 40
ttgtacactt catgcagcca                                        20

SEQ ID NO: 41          moltype = DNA  length = 20
FEATURE                Location/Qualifiers
source                 1..20
                       mol_type = other DNA
                       organism = synthetic construct
SEQUENCE: 41
caatacgtgg agacaagtac                                        20

SEQ ID NO: 42          moltype = DNA  length = 15
FEATURE                Location/Qualifiers
source                 1..15
                       mol_type = other DNA
                       organism = synthetic construct
SEQUENCE: 42
ttgtccaatt cgtgc                                             15

SEQ ID NO: 43          moltype = DNA  length = 15
FEATURE                Location/Qualifiers
source                 1..15
                       mol_type = other DNA
                       organism = synthetic construct
SEQUENCE: 43
caatacgtgc agcca                                             15

SEQ ID NO: 44          moltype = DNA  length = 15
FEATURE                Location/Qualifiers
source                 1..15
                       mol_type = other DNA
```

```
                        organism = synthetic construct
SEQUENCE: 44
ttgtgcaatg cgtgc                                                     15

SEQ ID NO: 45           moltype = DNA  length = 15
FEATURE                 Location/Qualifiers
source                  1..15
                        mol_type = other DNA
                        organism = synthetic construct
SEQUENCE: 45
caattcgagc agcca                                                     15

SEQ ID NO: 46           moltype = DNA  length = 15
FEATURE                 Location/Qualifiers
source                  1..15
                        mol_type = other DNA
                        organism = synthetic construct
SEQUENCE: 46
ttgtggaatt cgtgc                                                     15

SEQ ID NO: 47           moltype = DNA  length = 15
FEATURE                 Location/Qualifiers
source                  1..15
                        mol_type = other DNA
                        organism = synthetic construct
SEQUENCE: 47
ttgtgcaata cgtgc                                                     15

SEQ ID NO: 48           moltype = DNA  length = 15
FEATURE                 Location/Qualifiers
source                  1..15
                        mol_type = other DNA
                        organism = synthetic construct
SEQUENCE: 48
ttgtgcaaat cgtgc                                                     15

SEQ ID NO: 49           moltype = DNA  length = 15
FEATURE                 Location/Qualifiers
source                  1..15
                        mol_type = other DNA
                        organism = synthetic construct
SEQUENCE: 49
caattagtgc agcca                                                     15

SEQ ID NO: 50           moltype = DNA  length = 15
FEATURE                 Location/Qualifiers
source                  1..15
                        mol_type = other DNA
                        organism = synthetic construct
SEQUENCE: 50
caattcgtga agcca                                                     15

SEQ ID NO: 51           moltype = DNA  length = 15
FEATURE                 Location/Qualifiers
source                  1..15
                        mol_type = other DNA
                        organism = synthetic construct
SEQUENCE: 51
caatccgtgc agcca                                                     15

SEQ ID NO: 52           moltype = DNA  length = 15
FEATURE                 Location/Qualifiers
source                  1..15
                        mol_type = other DNA
                        organism = synthetic construct
SEQUENCE: 52
ttgtgcaatt agtgc                                                     15

SEQ ID NO: 53           moltype = DNA  length = 15
FEATURE                 Location/Qualifiers
source                  1..15
                        mol_type = other DNA
                        organism = synthetic construct
SEQUENCE: 53
ttgtgcgagt cgtgc                                                     15

SEQ ID NO: 54           moltype = DNA  length = 15
FEATURE                 Location/Qualifiers
source                  1..15
```

```
                           mol_type = other DNA
                           organism = synthetic construct
SEQUENCE: 54
caattcgtac agcca                                                   15

SEQ ID NO: 55              moltype = DNA  length = 15
FEATURE                    Location/Qualifiers
source                     1..15
                           mol_type = other DNA
                           organism = synthetic construct
SEQUENCE: 55
ttgtgctagt cgtgc                                                   15

SEQ ID NO: 56              moltype = DNA  length = 15
FEATURE                    Location/Qualifiers
source                     1..15
                           mol_type = other DNA
                           organism = synthetic construct
SEQUENCE: 56
caattcgagc tgcca                                                   15

SEQ ID NO: 57              moltype = DNA  length = 15
FEATURE                    Location/Qualifiers
source                     1..15
                           mol_type = other DNA
                           organism = synthetic construct
SEQUENCE: 57
caattcgcgc tgcca                                                   15

SEQ ID NO: 58              moltype = DNA  length = 10
FEATURE                    Location/Qualifiers
source                     1..10
                           mol_type = other DNA
                           organism = synthetic construct
SEQUENCE: 58
gggaatcgac                                                         10

SEQ ID NO: 59              moltype = DNA  length = 10
FEATURE                    Location/Qualifiers
source                     1..10
                           mol_type = other DNA
                           organism = synthetic construct
SEQUENCE: 59
gggaaaaaaa                                                         10

SEQ ID NO: 60              moltype = DNA  length = 10
FEATURE                    Location/Qualifiers
source                     1..10
                           mol_type = other DNA
                           organism = synthetic construct
SEQUENCE: 60
ggaaaaaaaa                                                         10

SEQ ID NO: 61              moltype = DNA  length = 10
FEATURE                    Location/Qualifiers
source                     1..10
                           mol_type = other DNA
                           organism = synthetic construct
SEQUENCE: 61
gaaaaaaaaa                                                         10

SEQ ID NO: 62              moltype = DNA  length = 10
FEATURE                    Location/Qualifiers
source                     1..10
                           mol_type = other DNA
                           organism = synthetic construct
SEQUENCE: 62
gccccccccc                                                         10

SEQ ID NO: 63              moltype = DNA  length = 15
FEATURE                    Location/Qualifiers
source                     1..15
                           mol_type = other DNA
                           organism = synthetic construct
SEQUENCE: 63
gggaatcgac tacag                                                   15

SEQ ID NO: 64              moltype = DNA  length = 15
FEATURE                    Location/Qualifiers
```

```
source                  1..15
                        mol_type = other DNA
                        organism = synthetic construct
SEQUENCE: 64
gggaaaaaaa aaaaa                                                        15

SEQ ID NO: 65           moltype = DNA  length = 15
FEATURE                 Location/Qualifiers
source                  1..15
                        mol_type = other DNA
                        organism = synthetic construct
SEQUENCE: 65
ggaaaaaaaa aaaaa                                                        15

SEQ ID NO: 66           moltype = DNA  length = 15
FEATURE                 Location/Qualifiers
source                  1..15
                        mol_type = other DNA
                        organism = synthetic construct
SEQUENCE: 66
gaaaaaaaaa aaaaa                                                        15

SEQ ID NO: 67           moltype = DNA  length = 15
FEATURE                 Location/Qualifiers
source                  1..15
                        mol_type = other DNA
                        organism = synthetic construct
SEQUENCE: 67
gccccccccc ccccc                                                        15

SEQ ID NO: 68           moltype = DNA  length = 20
FEATURE                 Location/Qualifiers
source                  1..20
                        mol_type = other DNA
                        organism = synthetic construct
SEQUENCE: 68
gggaatcgac tacaggagga                                                   20

SEQ ID NO: 69           moltype = DNA  length = 20
FEATURE                 Location/Qualifiers
source                  1..20
                        mol_type = other DNA
                        organism = synthetic construct
SEQUENCE: 69
gggaaaaaaa aaaaaaaaaa                                                   20

SEQ ID NO: 70           moltype = DNA  length = 10
FEATURE                 Location/Qualifiers
source                  1..10
                        mol_type = other DNA
                        organism = synthetic construct
SEQUENCE: 70
cggaatatag                                                              10

SEQ ID NO: 71           moltype = DNA  length = 10
FEATURE                 Location/Qualifiers
source                  1..10
                        mol_type = other DNA
                        organism = synthetic construct
SEQUENCE: 71
aaaaaaaaaa                                                              10

SEQ ID NO: 72           moltype = DNA  length = 10
FEATURE                 Location/Qualifiers
source                  1..10
                        mol_type = other DNA
                        organism = synthetic construct
SEQUENCE: 72
cccccccccc                                                              10

SEQ ID NO: 73           moltype = DNA  length = 15
FEATURE                 Location/Qualifiers
source                  1..15
                        mol_type = other DNA
                        organism = synthetic construct
SEQUENCE: 73
cggaatatag aagca                                                        15

SEQ ID NO: 74           moltype = DNA  length = 15
```

```
FEATURE                Location/Qualifiers
source                 1..15
                       mol_type = other DNA
                       organism = synthetic construct
SEQUENCE: 74
aaaaaaaaaa aaaaa                                                  15

SEQ ID NO: 75          moltype = DNA  length = 15
FEATURE                Location/Qualifiers
source                 1..15
                       mol_type = other DNA
                       organism = synthetic construct
SEQUENCE: 75
cccccccccc ccccc                                                  15

SEQ ID NO: 76          moltype = DNA  length = 20
FEATURE                Location/Qualifiers
source                 1..20
                       mol_type = other DNA
                       organism = synthetic construct
SEQUENCE: 76
cggaatatag aagcataaga                                             20

SEQ ID NO: 77          moltype = DNA  length = 20
FEATURE                Location/Qualifiers
source                 1..20
                       mol_type = other DNA
                       organism = synthetic construct
SEQUENCE: 77
aaaaaaaaaa aaaaaaaaaa                                             20

SEQ ID NO: 78          moltype = DNA  length = 20
FEATURE                Location/Qualifiers
source                 1..20
                       mol_type = other DNA
                       organism = synthetic construct
SEQUENCE: 78
cccccccccc cccccccccc                                             20

SEQ ID NO: 79          moltype = DNA  length = 50
FEATURE                Location/Qualifiers
source                 1..50
                       mol_type = other DNA
                       organism = synthetic construct
SEQUENCE: 79
taatacgact cactataggg ttatgataac tggctgcacg aattgcacaa            50

SEQ ID NO: 80          moltype = DNA  length = 30
FEATURE                Location/Qualifiers
source                 1..30
                       mol_type = other DNA
                       organism = synthetic construct
SEQUENCE: 80
agcgacttcg ttgtgcaatt cgtgcagcca                                  30

SEQ ID NO: 81          moltype = DNA  length = 10
FEATURE                Location/Qualifiers
source                 1..10
                       mol_type = other DNA
                       organism = synthetic construct
SEQUENCE: 81
tgccgtcggt                                                        10

SEQ ID NO: 82          moltype = DNA  length = 10
FEATURE                Location/Qualifiers
source                 1..10
                       mol_type = other DNA
                       organism = synthetic construct
SEQUENCE: 82
accgacggca                                                        10

SEQ ID NO: 83          moltype = DNA  length = 50
FEATURE                Location/Qualifiers
source                 1..50
                       mol_type = other DNA
                       organism = synthetic construct
SEQUENCE: 83
aaaaaaaaaa aaaaaaaaaa aaaaaaaaaa accgacggca aaaaaaaaaa            50
```

```
SEQ ID NO: 84          moltype = DNA  length = 50
FEATURE                Location/Qualifiers
source                 1..50
                       mol_type = other DNA
                       organism = synthetic construct
SEQUENCE: 84
tttttttttt tgccgtcggt tttttttttt tttttttttt tttttttttt            50

SEQ ID NO: 85          moltype = DNA  length = 50
FEATURE                Location/Qualifiers
source                 1..50
                       mol_type = other DNA
                       organism = synthetic construct
SEQUENCE: 85
gggaaaaaaa tgccgtcggt acgttactgg ccgaagccgc ttggaataag            50

SEQ ID NO: 86          moltype = DNA  length = 50
FEATURE                Location/Qualifiers
source                 1..50
                       mol_type = other DNA
                       organism = synthetic construct
SEQUENCE: 86
cttattccaa gcggcttcgg ccagtaacgt accgacggca tttttttccc            50

SEQ ID NO: 87          moltype = DNA  length = 10
FEATURE                Location/Qualifiers
source                 1..10
                       mol_type = other DNA
                       organism = synthetic construct
SEQUENCE: 87
gcacgaattg                                                        10

SEQ ID NO: 88          moltype = DNA  length = 30
FEATURE                Location/Qualifiers
source                 1..30
                       mol_type = other DNA
                       organism = synthetic construct
SEQUENCE: 88
actcgaacgt accgattgtg caattcgtgc                                  30

SEQ ID NO: 89          moltype = DNA  length = 20
FEATURE                Location/Qualifiers
source                 1..20
                       mol_type = other DNA
                       organism = synthetic construct
SEQUENCE: 89
accgattgtg caattcgtgc                                             20

SEQ ID NO: 90          moltype = DNA  length = 15
FEATURE                Location/Qualifiers
source                 1..15
                       mol_type = other DNA
                       organism = synthetic construct
SEQUENCE: 90
ttgtgcaatt cgtgc                                                  15

SEQ ID NO: 91          moltype = DNA  length = 15
FEATURE                Location/Qualifiers
source                 1..15
                       mol_type = other DNA
                       organism = synthetic construct
SEQUENCE: 91
ttgtgaaatt ggtgc                                                  15

SEQ ID NO: 92          moltype = DNA  length = 15
FEATURE                Location/Qualifiers
source                 1..15
                       mol_type = other DNA
                       organism = synthetic construct
SEQUENCE: 92
ttgtccaatt agtgc                                                  15

SEQ ID NO: 93          moltype = DNA  length = 10
FEATURE                Location/Qualifiers
source                 1..10
                       mol_type = other DNA
                       organism = synthetic construct
SEQUENCE: 93
caatttgtgc                                                        10
```

-continued

```
SEQ ID NO: 94          moltype = RNA  length = 20
FEATURE                Location/Qualifiers
source                 1..20
                       mol_type = other RNA
                       organism = synthetic construct
SEQUENCE: 94
gggaaaaaaa tgccgtcggt                                             20

SEQ ID NO: 95          moltype = RNA  length = 20
FEATURE                Location/Qualifiers
source                 1..20
                       mol_type = other RNA
                       organism = synthetic construct
SEQUENCE: 95
accgacggca aaaaaaaaaa                                             20
```